(12) United States Patent
Makower et al.

(10) Patent No.: US 11,589,742 B2
(45) Date of Patent: Feb. 28, 2023

(54) METHODS AND APPARATUS FOR TREATING DISORDERS OF THE EAR NOSE AND THROAT

(71) Applicant: Acclarent, Inc., Irvine, CA (US)

(72) Inventors: Joshua Makower, Los Altos, CA (US); John Y. Chang, Los Altos, CA (US); Ketan P. Muni, San Jose, CA (US); John H. Morriss, Emerald Hills, CA (US); Hung V. Ha, San Jose, CA (US); Isaac J. Kim, San Jose, CA (US); Julia D. Vrany, Los Altos, CA (US)

(73) Assignee: Acclarent, Inc., Irvine, CA (US)

( * ) Notice: Subject to any disclaimer, the term of this patent is extended or adjusted under 35 U.S.C. 154(b) by 251 days.

(21) Appl. No.: 17/032,000

(22) Filed: Sep. 25, 2020

(65) Prior Publication Data

US 2021/0015352 A1    Jan. 21, 2021

Related U.S. Application Data

(63) Continuation of application No. 15/795,834, filed on Oct. 27, 2017, now Pat. No. 10,813,547, which is a
(Continued)

(51) Int. Cl.
*A61B 34/20* (2016.01)
*A61B 1/233* (2006.01)
(Continued)

(52) U.S. Cl.
CPC .......... *A61B 1/233* (2013.01); *A61B 1/00135* (2013.01); *A61B 1/018* (2013.01);
(Continued)

(58) Field of Classification Search
CPC ........ A61B 17/12104; A61B 17/12136; A61B 1/0661; A61B 2090/3945; A61B 8/12;
(Continued)

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CA | 2013323 | 9/1990 |
| CH | 668188 | 12/1988 |

(Continued)

OTHER PUBLICATIONS

Argon Medical. Maxxim Medical. Ad for Sniper EliteTM Hydrophilic Ni—Ti Alloy Guidewire (2001).
(Continued)

*Primary Examiner* — Deanna K Hall
(74) *Attorney, Agent, or Firm* — Frost Brown Todd LLP

(57) ABSTRACT

Methods and apparatus for treating disorders of the ear, nose, throat or paranasal sinuses, including methods and apparatus for dilating ostia, passageways and other anatomical structures, endoscopic methods and apparatus for endoscopic visualization of structures within the ear, nose, throat or paranasal sinuses, navigation devices for use in conjunction with image guidance or navigation system and hand held devices having pistol type grips and other handpieces.

20 Claims, 38 Drawing Sheets

Related U.S. Application Data continuation of application No. 11/929,667, filed on Oct. 30, 2007, now Pat. No. 9,814,379, which is a continuation of application No. 11/193,020, filed on Jul. 29, 2005, now abandoned, which is a continuation-in-part of application No. 11/116,118, filed on Apr. 26, 2005, now Pat. No. 7,720,521, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997.

(51) Int. Cl.
| | | |
|---|---|---|
| *A61B 90/50* | (2016.01) | |
| *A61B 1/00* | (2006.01) | |
| *A61B 1/018* | (2006.01) | |
| *A61B 1/267* | (2006.01) | |
| *A61B 17/24* | (2006.01) | |
| *A61B 17/28* | (2006.01) | |
| *A61B 17/34* | (2006.01) | |
| *A61M 29/02* | (2006.01) | |
| *A61B 90/00* | (2016.01) | |
| *A61B 1/005* | (2006.01) | |

(52) U.S. Cl.
CPC ............. *A61B 1/267* (2013.01); *A61B 17/24* (2013.01); *A61B 17/282* (2013.01); *A61B 17/2804* (2013.01); *A61B 17/3421* (2013.01); *A61B 34/20* (2016.02); *A61B 90/50* (2016.02); *A61M 29/02* (2013.01); *A61B 1/0051* (2013.01); *A61B 90/361* (2016.02); *A61B 2017/3445* (2013.01); *A61B 2017/3447* (2013.01); *A61B 2034/2051* (2016.02); *A61B 2034/2055* (2016.02); *A61B 2034/2065* (2016.02); *A61B 2090/063* (2016.02); *A61B 2090/0811* (2016.02); *A61B 2090/376* (2016.02); *A61B 2090/3941* (2016.02); *A61B 2090/3954* (2016.02); *A61M 2029/025* (2013.01); *A61M 2210/0681* (2013.01)

(58) Field of Classification Search
CPC ............ A61B 90/36; A61B 2034/2051; A61B 2034/2055; A61B 2034/2065; A61B 2090/0811; A61B 2090/376; A61B 2090/3941; A61B 2090/3954; A61B 34/20; A61B 90/361; A61B 2090/0805; A61M 25/0068; A61M 25/0074; A61M 25/10

See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,477,438 A | 11/1969 | Allen et al. |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,137 A | 6/1970 | Santomieri |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,726,284 A | 4/1973 | Parker |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,311,146 A | 1/1982 | Wonder |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,441,495 A | 4/1984 | Hicswa |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,517,979 A | 5/1985 | Pecenka |
| 4,554,929 A | 11/1985 | Samson et al. |
| 4,564,364 A | 1/1986 | Zaffaroni et al. |
| 4,571,239 A | 2/1986 | Heyman |

(56) References Cited

U.S. PATENT DOCUMENTS

| | | |
|---|---|---|
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,684,363 A | 8/1987 | Ari et al. |
| 4,686,965 A | 8/1987 | Bonnet et al. |
| 4,691,948 A | 9/1987 | Austin, Jr. et al. |
| 4,696,544 A | 9/1987 | Costella |
| 4,700,694 A | 10/1987 | Shishido |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,802,461 A | 2/1989 | Cho |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,926,858 A | 5/1990 | Gifford, III et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Yamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandoninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,161,534 A | 11/1992 | Berthiaume |
| 5,163,989 A | 11/1992 | Campbell et al. |
| 5,165,420 A | 11/1992 | Strickland |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,292,305 A | 3/1994 | Boudewijn et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |

(56) References Cited

U.S. PATENT DOCUMENTS

| | | |
|---|---|---|
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,318,008 A | 6/1994 | Bullard |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,370,640 A | 12/1994 | Koloff |
| 5,372,138 A | 12/1994 | Crowley et al. |
| 5,372,584 A | 12/1994 | Zink et al. |
| D355,031 S | 1/1995 | Yoshikawa |
| 5,378,234 A | 1/1995 | Hammerslag et al. |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,397,305 A | 3/1995 | Kawula et al. |
| 5,402,799 A | 4/1995 | Colon et al. |
| 5,409,444 A | 4/1995 | Kensey et al. |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,483 A | 8/1995 | Avitall |
| 5,441,494 A | 8/1995 | Ortiz |
| 5,441,497 A | 8/1995 | Narciso, Jr. |
| 5,441,515 A | 8/1995 | Khosravi et al. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,585 A | 2/1997 | Banik et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,621 A | 9/1997 | Lafontaine |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,749,920 A | 5/1998 | Quiachon et al. |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,823,961 A | 10/1998 | Fields et al. |
| 5,824,044 A | 10/1998 | Quiachon et al. |

(56) References Cited

U.S. PATENT DOCUMENTS

| | | |
|---|---|---|
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,147 A | 6/1999 | Boury |
| 5,916,193 A | 6/1999 | Stevens et al. |
| 5,916,213 A | 6/1999 | Haissaguerre et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| 5,941,849 A | 8/1999 | Amos, Jr. et al. |
| D413,629 S | 9/1999 | Wolff et al. |
| 5,947,988 A | 9/1999 | Smith |
| 5,947,991 A | 9/1999 | Cowan |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,989,025 A | 11/1999 | Conley |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,238,430 B1 | 5/2001 | Klumb et al. |
| 6,241,519 B1 | 6/2001 | Sedleemayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,264,087 B1 | 7/2001 | Whitman |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 9/2001 | Powell et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,296,638 B1 | 10/2001 | Davison et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |

(56) References Cited

U.S. PATENT DOCUMENTS

| | | |
|---|---|---|
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,351,659 B1 | 2/2002 | Vilsmeier |
| 6,352,503 B1 | 3/2002 | Matsui et al. |
| 6,355,032 B1 | 3/2002 | Hovda et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,569,191 B1 | 5/2003 | Hogan |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,633,773 B1 | 10/2003 | Reisfeld |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,645,223 B2 | 11/2003 | Boyle et al. |
| 6,650,927 B1 | 11/2003 | Keidar |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,740,191 B2 | 5/2004 | Clarke et al. |
| 6,741,884 B1 | 5/2004 | Freeman et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,866,669 B2 | 3/2005 | Buzzard et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,953,431 B2 | 10/2005 | Barthel |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |

(56) References Cited

U.S. PATENT DOCUMENTS

| | | | |
|---|---|---|---|
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,001,369 B2 | 2/2006 | Griffin et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,037,321 B2 | 5/2006 | Sachdeva |
| 7,043,961 B2 | 5/2006 | Pandey |
| 7,044,964 B2 | 5/2006 | Jang et al. |
| 7,048,711 B2 | 5/2006 | Rosemann et al. |
| 7,052,474 B2 | 5/2006 | Castell et al. |
| 7,056,284 B2 | 6/2006 | Martone et al. |
| 7,056,287 B2 | 6/2006 | Taylor et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,751,758 B2 | 7/2010 | Yahagi |
| 7,753,929 B2 | 7/2010 | Becker |
| 7,753,930 B2 | 7/2010 | Becker |
| 7,758,497 B2 | 7/2010 | Hern |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,075,478 B2 | 12/2011 | Campos |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |

(56) References Cited

U.S. PATENT DOCUMENTS

| | | |
|---|---|---|
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,475,360 B2 | 7/2013 | Brown |
| 8,521,259 B2 | 8/2013 | Mandrusov et al. |
| 8,529,439 B2 | 9/2013 | Ito et al. |
| 8,535,707 B2 | 9/2013 | Arensdorf et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,777,926 B2 | 7/2014 | Chang et al. |
| 8,802,131 B2 | 8/2014 | Arensdorf et al. |
| 8,828,041 B2 | 9/2014 | Chang et al. |
| 8,870,893 B2 | 10/2014 | Makower et al. |
| 8,894,614 B2 | 11/2014 | Muni et al. |
| 8,894,787 B2 | 11/2014 | Boe |
| 8,905,922 B2 | 12/2014 | Makower et al. |
| 8,932,276 B1 | 1/2015 | Morriss et al. |
| 8,945,088 B2 | 2/2015 | Chang et al. |
| 8,951,225 B2 | 2/2015 | Evard et al. |
| 8,961,398 B2 | 2/2015 | Makower et al. |
| 8,961,495 B2 | 2/2015 | Chang et al. |
| 9,039,657 B2 | 5/2015 | Makower et al. |
| 9,055,965 B2 | 6/2015 | Chang et al. |
| 9,089,258 B2 | 7/2015 | Goldfarb et al. |
| 9,101,574 B2 | 8/2015 | Chang et al. |
| 9,101,739 B2 | 8/2015 | Lesch, Jr. et al. |
| 9,107,574 B2 | 8/2015 | Goldfarb et al. |
| 9,167,961 B2 | 10/2015 | Makower et al. |
| 9,179,823 B2 | 11/2015 | Goldfarb et al. |
| 9,216,112 B2 | 12/2015 | Clifford et al. |
| 9,220,879 B2 | 12/2015 | Chang et al. |
| 9,241,834 B2 | 1/2016 | Chang et al. |
| 9,265,407 B2 | 2/2016 | Goldfarb et al. |
| 9,289,576 B2 | 3/2016 | Mann et al. |
| 9,308,361 B2 | 4/2016 | Muni et al. |
| 9,351,750 B2 | 5/2016 | Muni et al. |
| 9,370,649 B2 | 6/2016 | Chang et al. |
| 9,399,121 B2 | 7/2016 | Goldfarb et al. |
| 9,468,453 B2 | 10/2016 | Hart et al. |
| 9,554,691 B2 | 1/2017 | Goldfarb et al. |
| 9,603,506 B2 | 3/2017 | Goldfarb et al. |
| 9,610,428 B2 | 4/2017 | Muni et al. |
| 9,649,477 B2 | 5/2017 | Muni et al. |
| 9,713,700 B2 | 7/2017 | Chang et al. |
| 9,814,379 B2 | 11/2017 | Makower et al. |
| 10,098,652 B2 | 10/2018 | Goldfarb et al. |
| 10,124,154 B2 | 11/2018 | Evard et al. |
| 10,188,413 B1 | 1/2019 | Morriss et al. |
| 10,492,810 B2 | 12/2019 | Chang et al. |
| 10,500,380 B2 | 12/2019 | Chang et al. |
| 10,631,756 B2 | 4/2020 | Kim et al. |
| 10,695,080 B2 | 6/2020 | Chang et al. |
| 10,779,752 B2 | 9/2020 | Kim et al. |
| 10,813,547 B2 | 10/2020 | Makower et al. |
| 2001/0004644 A1 | 6/2001 | Levin |
| 2001/0005785 A1 | 6/2001 | Sachse |
| 2001/0021843 A1 | 9/2001 | Bosselmann et al. |
| 2001/0034530 A1 | 10/2001 | Malackowski et al. |
| 2001/0037084 A1 | 11/2001 | Nardeo |
| 2002/0006961 A1 | 1/2002 | Katz et al. |
| 2002/0013548 A1 | 1/2002 | Hinchliffe |
| 2002/0045924 A1 | 4/2002 | Fox |
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0090388 A1 | 7/2002 | Humes et al. |
| 2002/0161389 A1 | 10/2002 | Boyle et al. |
| 2003/0009095 A1 | 1/2003 | Skarda |
| 2003/0009190 A1 | 1/2003 | Kletschka et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0051733 A1 | 3/2003 | Kotmel et al. |
| 2003/0073900 A1 | 4/2003 | Senarith et al. |
| 2003/0074045 A1 | 4/2003 | Buzzard et al. |
| 2003/0083608 A1 | 5/2003 | Evans et al. |
| 2003/0114732 A1 | 6/2003 | Webler et al. |
| 2003/0114909 A1 | 6/2003 | Clerc et al. |
| 2003/0163154 A1 | 8/2003 | Miyata et al. |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0064150 A1 | 4/2004 | Becker |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco et al. |
| 2005/0059930 A1 | 3/2005 | Garrison et al. |
| 2005/0059931 A1 | 3/2005 | Garrison et al. |
| 2005/0089670 A1 | 4/2005 | Large et al. |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0137621 A1 | 6/2005 | Stahl et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0240120 A1 | 10/2005 | Modesitt |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |

(56) References Cited

U.S. PATENT DOCUMENTS

| | | |
|---|---|---|
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0245608 A1 | 9/2013 | Muni et al. |
| 2013/0261388 A1 | 10/2013 | Jenkins et al. |
| 2015/0088188 A1 | 3/2015 | Muni et al. |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0209055 A1 | 7/2015 | Chang et al. |
| 2015/0250992 A1 | 9/2015 | Morriss et al. |
| 2016/0192830 A1 | 7/2016 | Goldfarb et al. |
| 2016/0270863 A1 | 9/2016 | Makower |
| 2017/0007281 A1 | 1/2017 | Goldfarb et al. |
| 2017/0071625 A1 | 3/2017 | Chang et al. |
| 2020/0164188 A1 | 5/2020 | Chang et al. |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | S5-367935 | 6/1978 |
| JP | S61-16750 | 1/1986 |
| JP | H10-24098 | 1/1989 |
| JP | S6-434376 | 2/1989 |
| JP | H01-305965 | 12/1989 |
| JP | H03-503011 | 7/1991 |
| JP | H03-504935 | 10/1991 |
| JP | 4-221313 | 8/1992 |
| JP | 4-224766 | 8/1992 |
| JP | H05-503650 | 6/1993 |
| JP | 5-211985 | 8/1993 |
| JP | H05-506805 | 10/1993 |
| JP | 06-17751 | 3/1994 |
| JP | 6-277296 | 10/1994 |
| JP | 7-327916 | 12/1995 |
| JP | 8-317989 | 12/1996 |
| JP | H10-034376 | 2/1998 |
| JP | H10-501159 | 2/1998 |
| JP | H10-94543 | 4/1998 |
| JP | H11-507251 | 6/1999 |
| JP | 2000-501634 | 2/2000 |
| JP | 2000-126303 | 5/2000 |
| JP | 2001-025508 | 1/2001 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |

(56) References Cited

FOREIGN PATENT DOCUMENTS

| | | |
|---|---|---|
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/082800 | 11/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435, (1978).
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. www.inventors.about.com/library/inventors/blcatheter.htm?p=1, no date given.
Benninger et al.; Adult Chronic Rhinosinusitis: Definitions, Diagnosis, Epidemiology, and Pathophysilogy' Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillumination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: The University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63, no date given.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue 1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Definition of "bent" as accessed Sep. 10, 2015, http://dictionary.reference.com/browse/bent.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
"Durometer Made Easy Durometer Hardness Scales—General Reference Guide." Paramount Industries, Inc. 2008. Accessed online: http://www.paramountind.com/pdfs/paramount_durometer_scale_guide.pdf.
"Durometer Shore Hardness Scale." Smooth-On, Inc. 2016. Accessed online: https://www.smooth-on.com/page/durometer-shore-hardness-scale/.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.

(56) References Cited

OTHER PUBLICATIONS

Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus' OASIS—Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.
Hojo, M. et al, 'Electrophilic Substitutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Miniature Endoscopes in Otorhinolaryngologic Applications' Min Invas Ther & Allied Technol. (1998) vol. 7, No. 3 pp. 209-218.
Hosemann, W. et al. 'A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.

Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' The Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. 'Too Years of Frontal Sinus Surgery' Laryngoscope. vol. 107 (1997) pp. 1-36.
K-Splint Internal Nasal Splints; Jan. 25, 2007: www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium (1993) Jul. 21-24.
Large, G.C. 'Crystalline Tetracycline Hydrochloride in the Treatment of Acute and Chronic Maxillary Sinusitis' Canada. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Merriam-Webster definition of "lumen" as accessed Jun. 10, 2016, http://www.merriam-webster.com/dictionary/lumen.
Metson, R., et al., 'Endoscopic Treatment of Sphenoid Sinusitis' Otolaryngol. Head Neck Surg. (1996) vol. 114, No. 6 pp. 736-744.

(56) References Cited

OTHER PUBLICATIONS

Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron—Rich Olefins' J. Org. Chem. vol. 60, No. 11 (1995) pp. 3523.3528. American Chemical Society.
Nasal Surgery and Accessories. Jan. 25, 2007; www.technologyforlife.com.au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' TEXAS State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [dale of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems, no date given.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. 'Die Behandlung von Stenosen der oberen Luftwege mittels rontgenologisch gesteuerter Ballondilation (Sep. 25, 1999) pp. 1-4.
Strohm, et al 'Le Traitenment des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Endoscopy (UK) Ltd.' p. 4, no date given.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the Europass™: A new Ultra-Low-Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.

(56) References Cited

OTHER PUBLICATIONS

Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
Chinese Office Action, Decision of Rejection, dated 2014 for Application No. CN 200980152995.1.
Chinese Office Action, Third Office Action, dated Feb. 27, 2014 for Application No. CN 200980152995.1.
Chinese Office Action and Search Report dated Jan. 21, 2015 for Application No. CN 201310672731.6.
European Communication dated Sep. 4, 2008 for Application No. EP 05773189.
European Communication dated Jun. 19, 2009 for Application No. EP 05773189.
European Communication dated Sep. 27, 2011 for Application No. EP 06800540.4.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
European Communication dated Sep. 26, 2016 for Application No. EP 12162712.9.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.
Extended European Search Report dated Jan. 17, 2014 for Application No. EP 108426321.1.
Extended European Search Report dated Sep. 15, 2015 for Application No. EP 15163549.7.
Extended European Search Report dated Jun. 28, 2017 for Application No. EP 17159646.3.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Mar. 24, 2010 for Application No. EP 07836108.6.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 8, 2011 for Application No. EP 06800540.4.
Supplemental European Search Report dated Sep. 29, 2011 for Application No. EP 07750248.
Supplemental European Search Report dated Jan. 14, 2014 for Application No. EP 13184009.

(56) References Cited

OTHER PUBLICATIONS

Supplemental European Search Report dated Jan. 17, 2014 for Application No. EP 1084263.
Supplemental European Search Report dated Feb. 27, 2014 for Application No. EP 08746464.0.
Supplemental European Search Report dated Dec. 9, 2014 for Application No. EP 07839152.
Supplemental European Search Report dated Feb. 13, 2014 for Application No. EP 08746464.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
International Written Opinion dated Aug. 9, 2011 for Application No. PCT/US2011/038751.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
Japanese Office Action, Reasons for Refusal dated Mar. 29, 2016 for Application No. JP 2012-266049.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.

(56) References Cited

OTHER PUBLICATIONS

USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 10/829,917, filed Apr. 21, 2004.
U.S. Appl. No. 10/944,270, filed Sep. 17, 2004.
U.S. Appl. No. 11/116,118, filed Apr. 26, 2005.
U.S. Appl. No. 11/193,020, filed Jul. 29, 2005.
U.S. Appl. No. 11/789,705, filed Apr. 24, 2007.
U.S. Appl. No. 11/804,308, filed May 16, 2007.
U.S. Appl. No. 11/804,309, filed May 16, 2007.
U.S. Appl. No. 11/929,667, filed Oct. 30, 2007.
U.S. Appl. No. 14/221,550, filed Mar. 21, 2014.
U.S. Appl. No. 14/221,621, filed Mar. 21, 2014.
U.S. Appl. No. 14/221,714, filed Mar. 21, 2014.
U.S. Appl. No. 14/265,888, filed Apr. 30, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.
U.S. Appl. No. 14/993,444, filed Jan. 12, 2016.
U.S. Appl. No. 15/083,826, filed Mar. 29, 2016.
U.S. Appl. No. 15/187,938, filed Jun. 21, 2016.
U.S. Appl. No. 15/624,111, filed Jun. 15, 2017.
U.S. Appl. No. 15/651,101, filed Jul. 17, 2017.
U.S. Appl. No. 15/795,834, filed Oct. 27, 2017.
U.S. Appl. No. 16/106,653.
U.S. Appl. No. 16/156,112.
U.S. Appl. No. 16/212,864.
U.S. Appl. No. 16/424,728.
U.S. Appl. No. 16/424,735.
U.S. Appl. No. 16/532,678.
U.S. Appl. No. 16/532,681.
U.S. Appl. No. 16/672,702.
U.S. Appl. No. 16/747,592.
U.S. Appl. No. 16/808,452.
U.S. Appl. No. 16/912,760.
Canadian Office Action dated Jun. 20, 2016 for Application No. CA 2,617,054.
European Communication dated May 12, 2017 for Application No. EP 09792627.3.
European Communication dated Jul. 14, 2017 for Application No. EP 06784759.0.
European Communication dated Aug. 2, 2017 for Application No. EP 12173295.2.

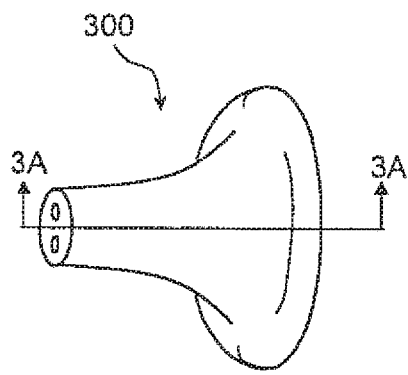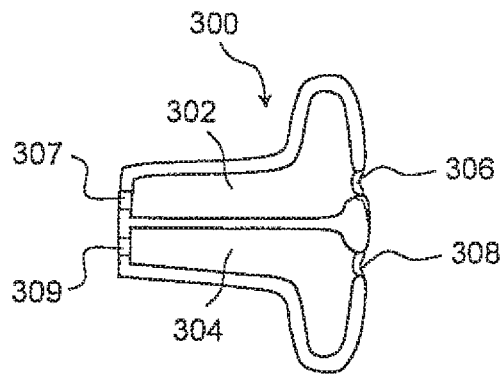
Fig. 3  Fig. 3A
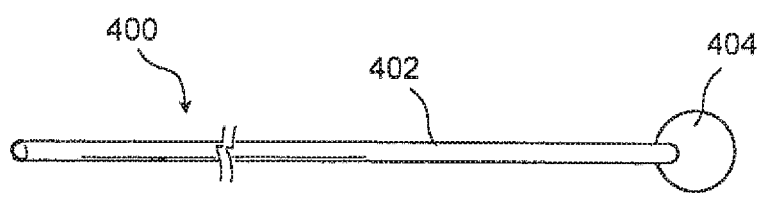
Fig. 4A
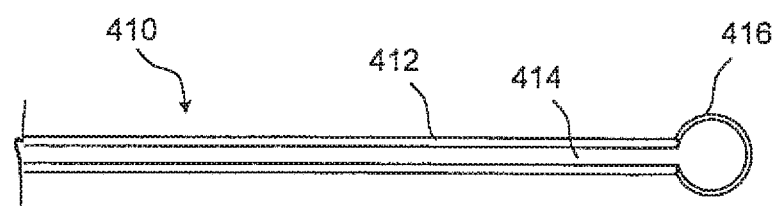
Fig. 4B

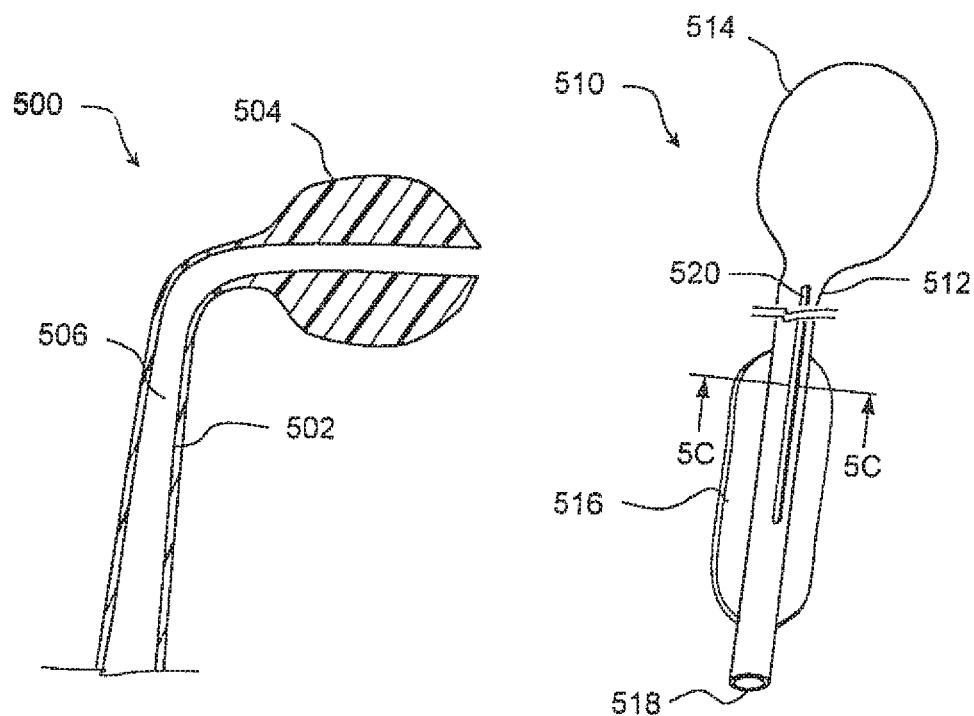
Fig. 5A
Fig. 5B
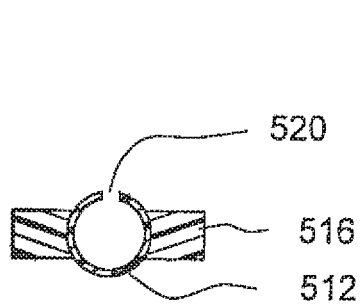
Fig. 5C
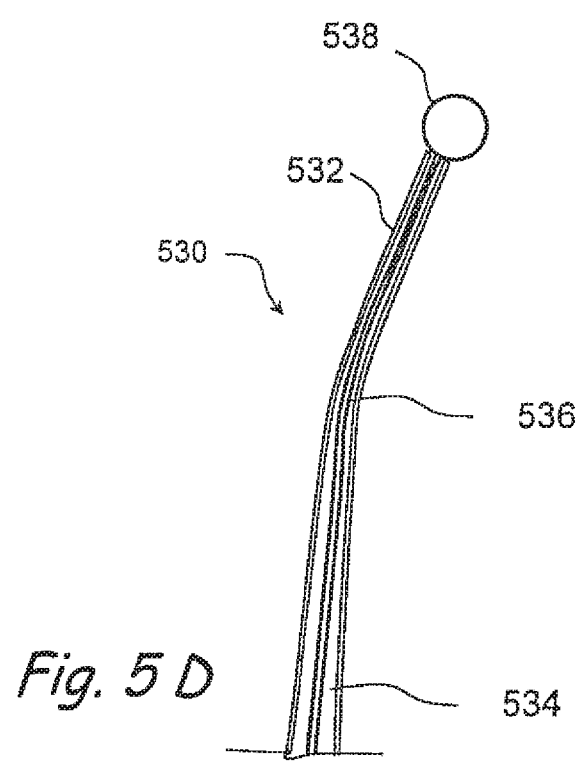
Fig. 5D

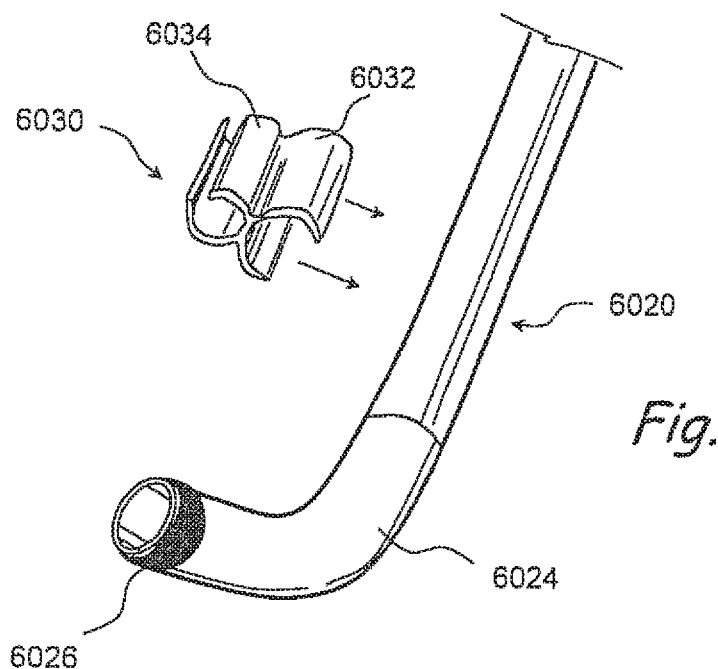
Fig. 6J
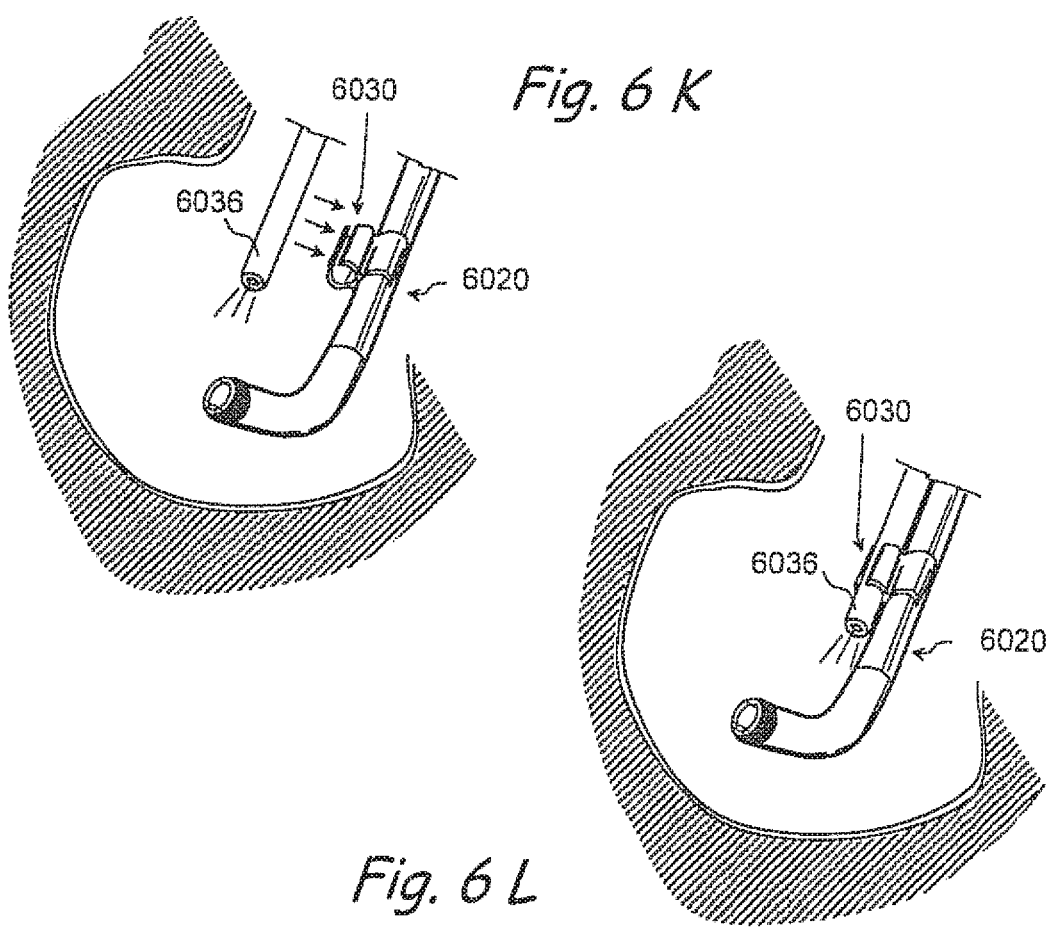
Fig. 6K
Fig. 6L

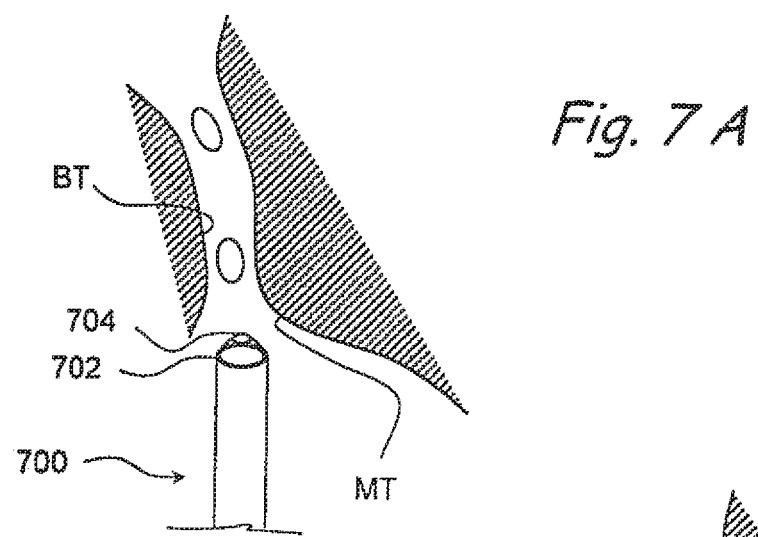
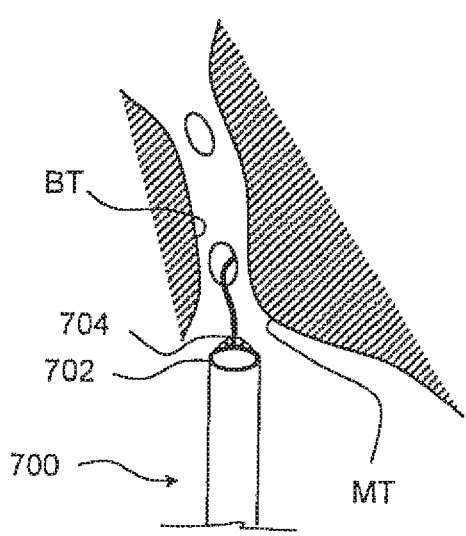
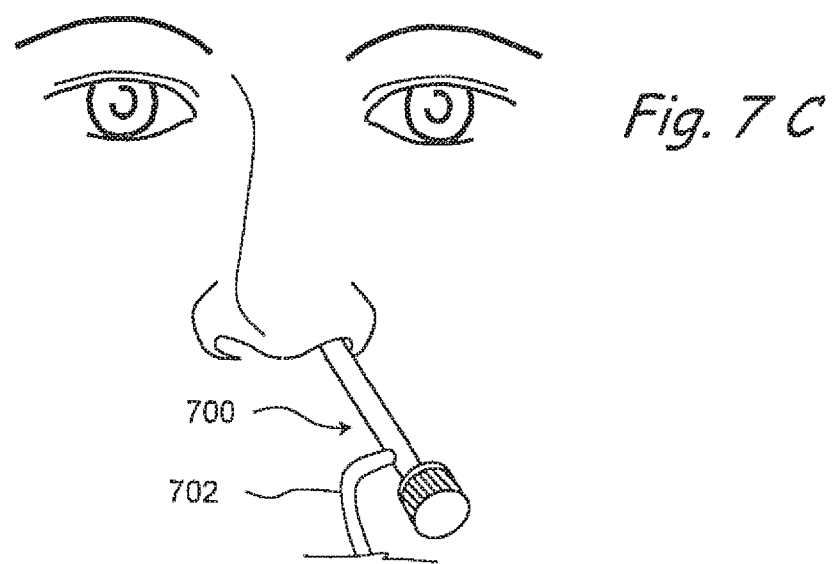

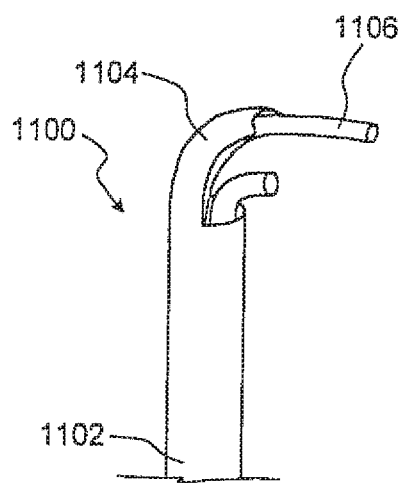
Fig. 11
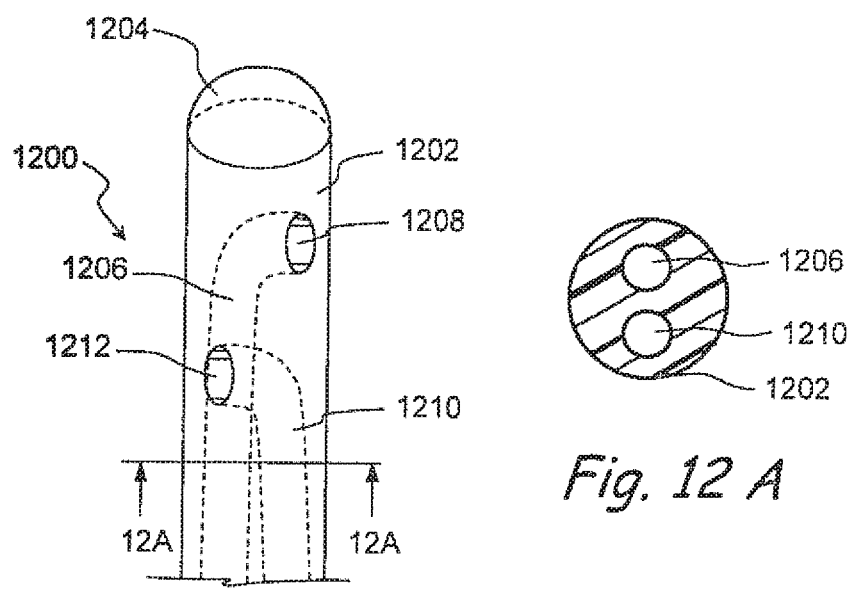
Fig. 12
Fig. 12 A

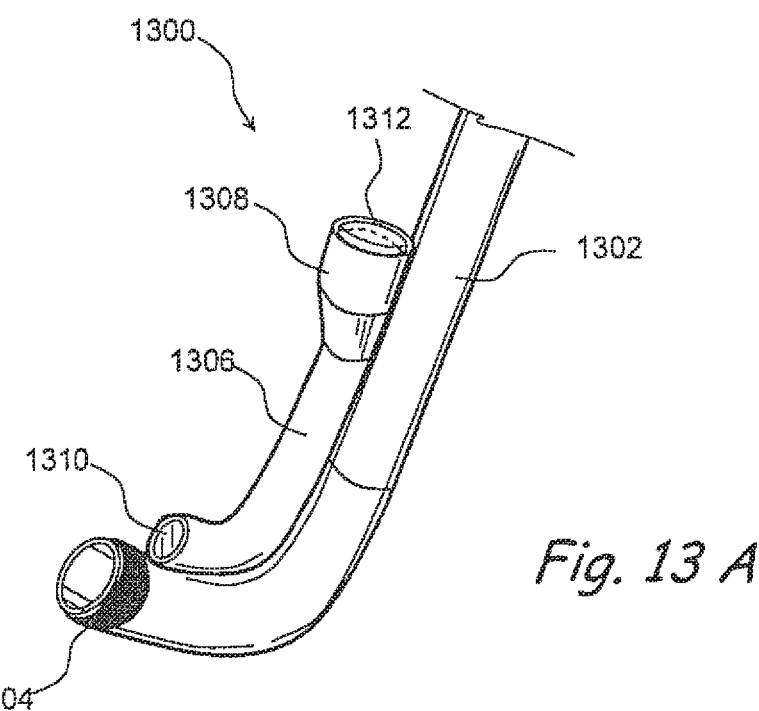
Fig. 13 A
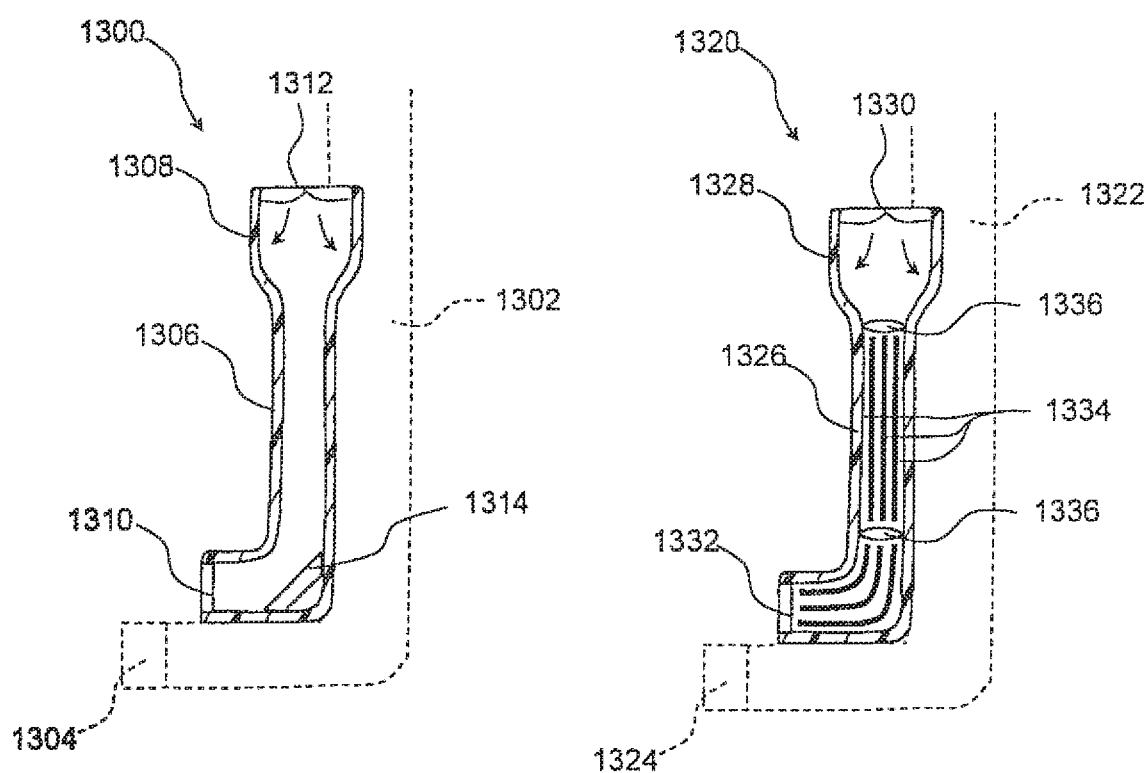
Fig. 13 B
Fig. 13 C

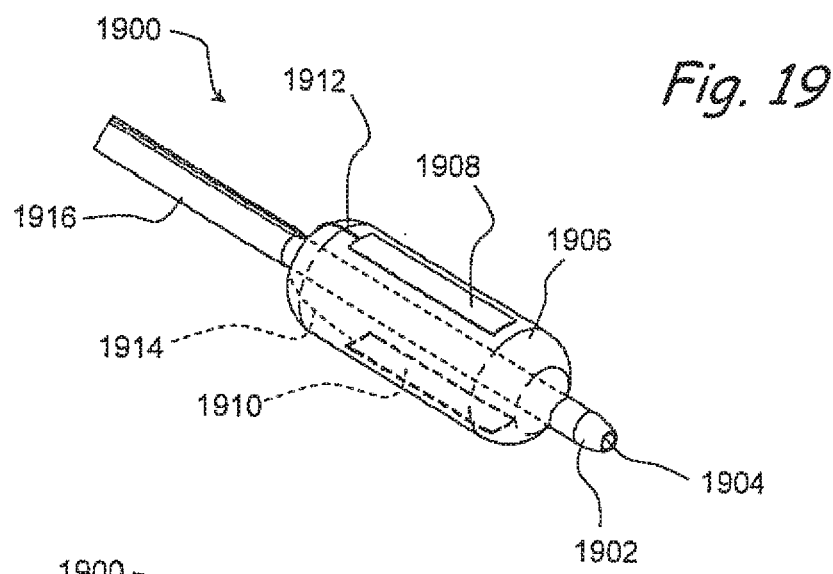
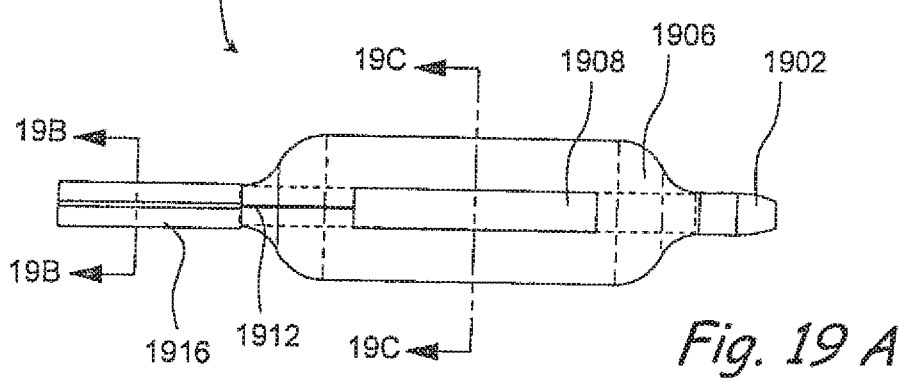
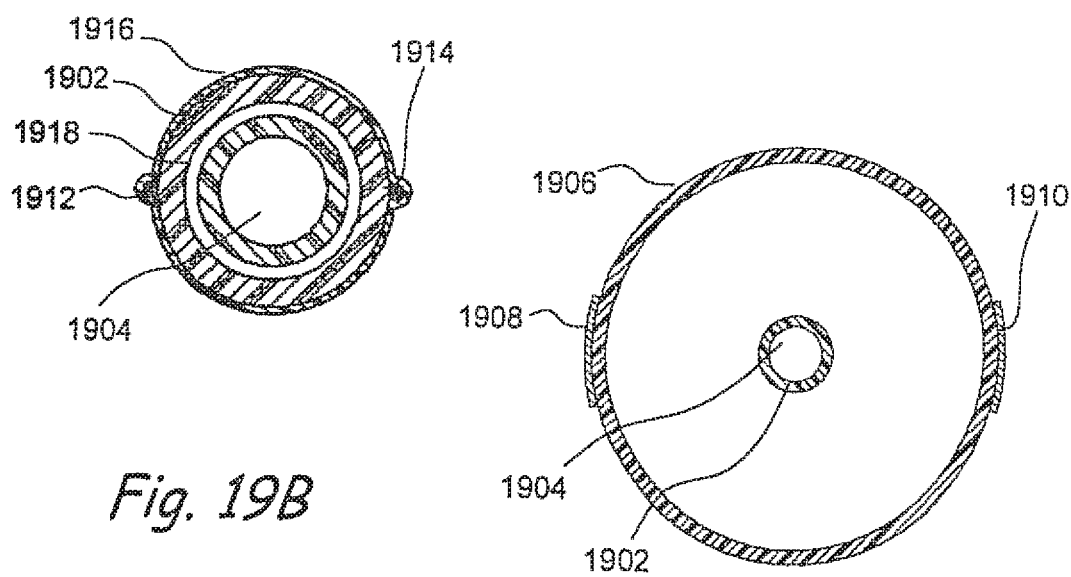
Fig. 19
Fig. 19 A
Fig. 19B
Fig. 19 C

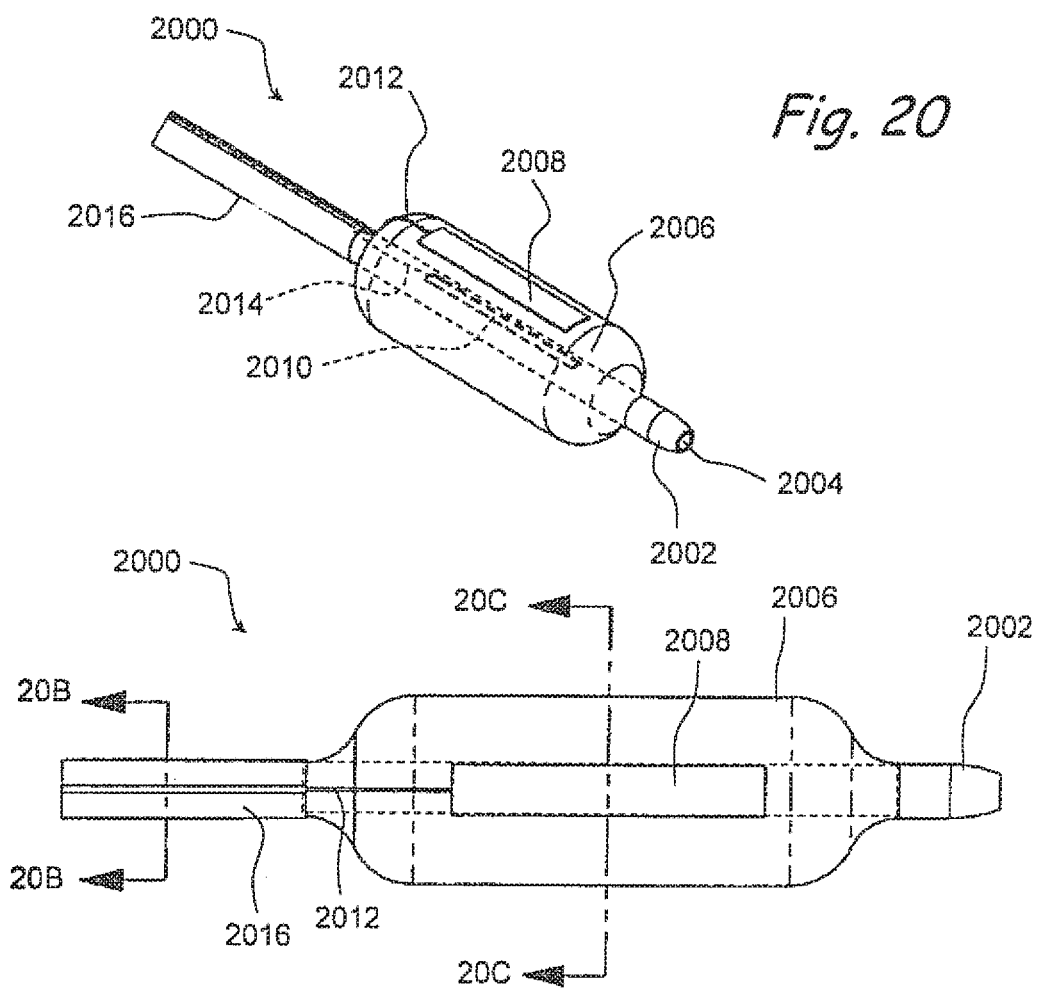
Fig. 20
Fig. 20 A
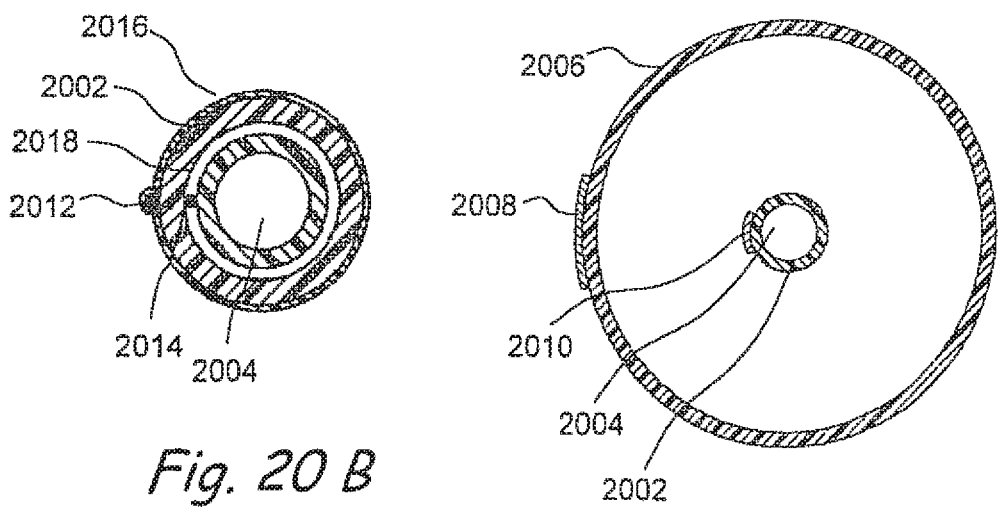
Fig. 20 B
Fig. 20 C

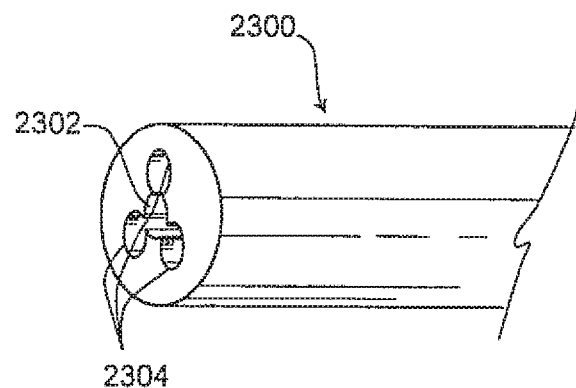
*Fig. 23*
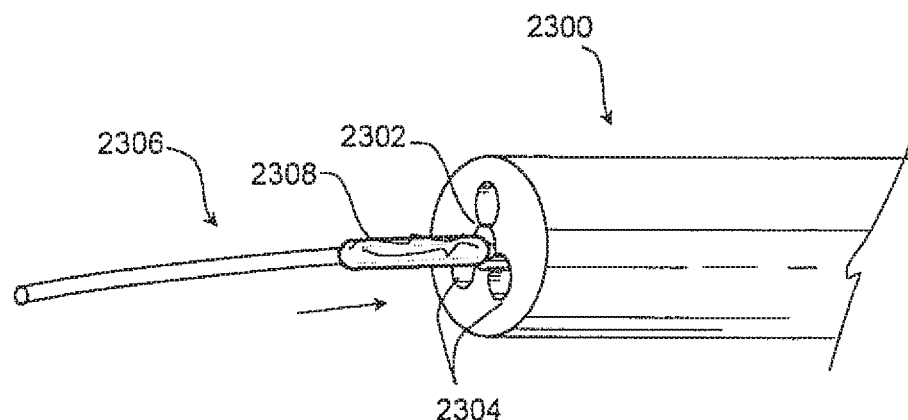
*Fig. 23 A*
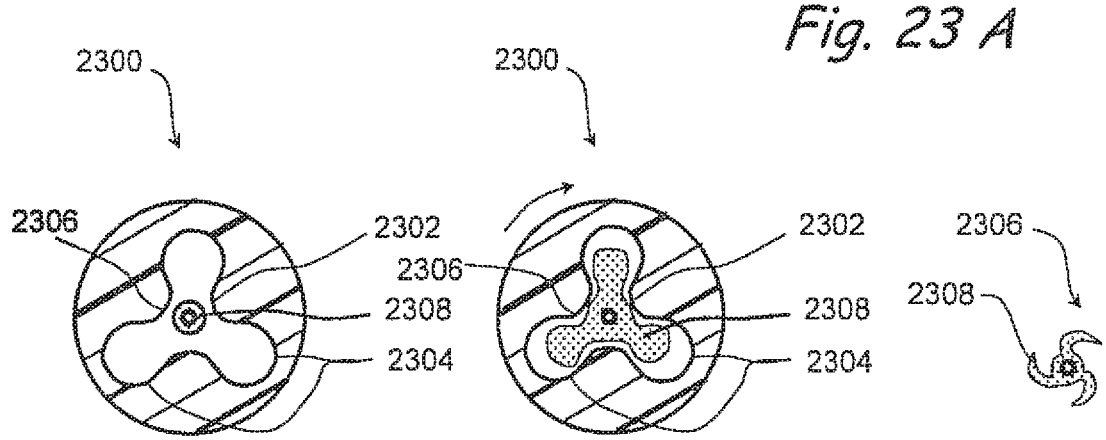
*Fig. 23 B*   *Fig. 23 C*   *Fig. 23 D*

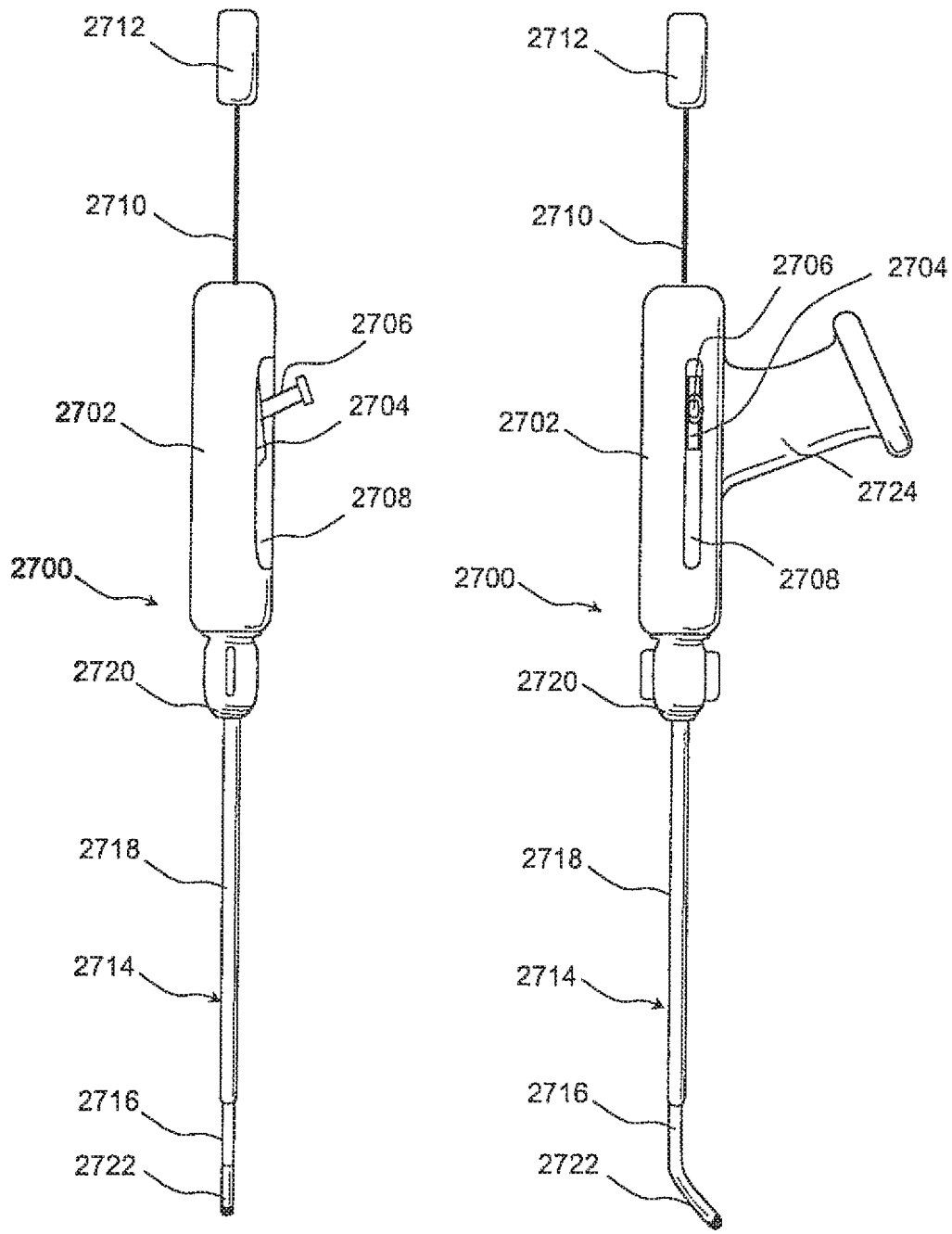

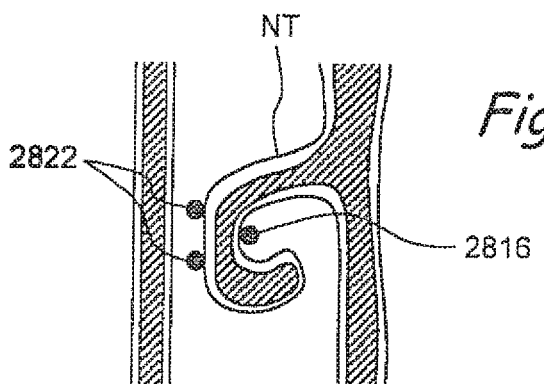
Fig. 29C
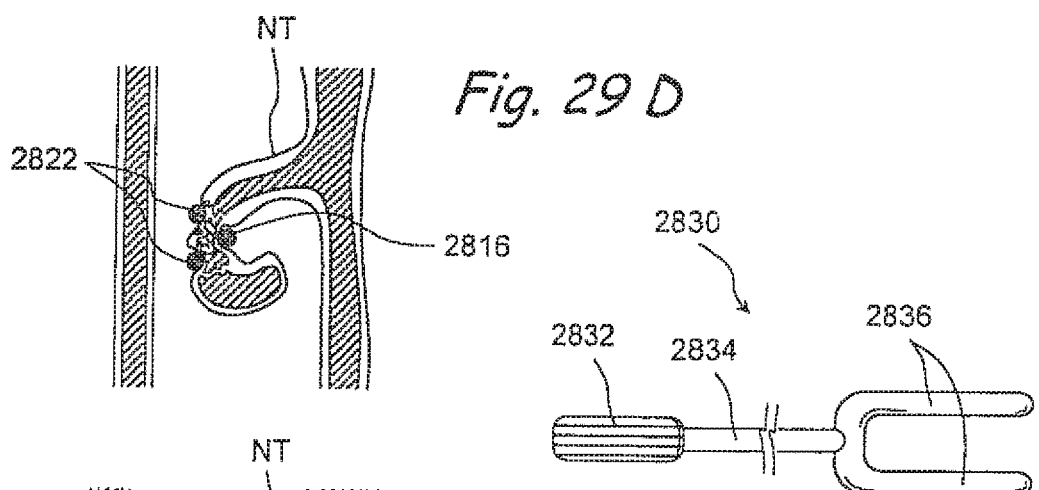
Fig. 29D
Fig. 29E
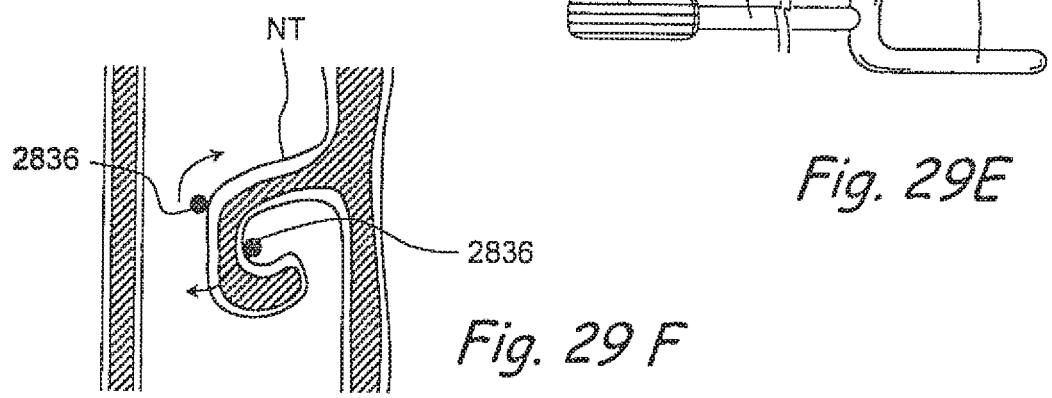
Fig. 29F
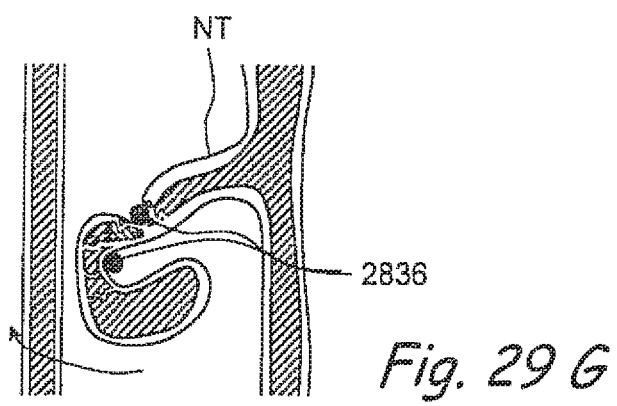
Fig. 29G

METHODS AND APPARATUS FOR TREATING DISORDERS OF THE EAR NOSE AND THROAT

RELATED APPLICATIONS

This application is a continuation of U.S. patent application Ser. No. 15/795,834 entitled "Methods and Apparatus for Treating Disorders of the Ear Nose and Throat" filed Oct. 27, 2017, issued as U.S. Pat. No. 10,813,547 on Oct. 7, 2020, which is a continuation of U.S. patent application Ser. No. 11/929,667 entitled "Methods and Apparatus for Treating Disorders of the Ear Nose and Throat" filed Oct. 30, 2007, now U.S. Pat. No. 9,814,379, which is a continuation of U.S. patent application Ser. No. 11/193,020 entitled "Methods and Apparatus for Treating Disorders of the Ear, Nose and Throat" filed on Jul. 29, 2005, now abandoned, which is a continuation-in-part of U.S. patent application Ser. No. 10/829,917 entitled "Devices, Systems and Methods for Diagnosing and Treating Sinusitis and Other Disorders of the Ears, Nose and/or Throat" filed on Apr. 21, 2004, now U.S. Pat. No. 7,654,997; Ser. No. 10/944,270 entitled "Apparatus and Methods for Dilating and Modifying Ostia of Paranasal Sinuses and Other Intranasal or Paranasal Structures" filed on Sep. 17, 2004, now abandoned; Ser. No. 11/116,118 entitled "Methods and Devices for Performing Procedures Within the Ear, Nose, Throat and Paranasal Sinuses" filed Apr. 26, 2005, now U.S. Pat. No. 7,720,521.

FIELD OF THE INVENTION

The present invention relates generally to medical apparatus and methods and more particularly to devices and methods that are useable to treat disorders of the paranasal sinuses as well as other ear, nose & throat disorders.

BACKGROUND OF THE INVENTION

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut tissue and/or bone, cauterize, suction, etc. In most FESS procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical instruments used in the prior art FESS procedures have included; applicators, chisels, curettes, elevators, forceps, gouges, hooks, knives, saws, mallets, morselizers, needle holders, osteotomes, ostium seekers, probes, punches, backbiters, rasps, retractors, rongeurs, scissors, snares, specula, suction canulae and trocars. The majority of such instruments are of substantially rigid design.

In order to adequately view the operative field through the endoscope and/or to allow insertion and use of rigid instruments, many FESS procedures of the prior art have included the surgical removal or modification of normal anatomical structures. For example, in many prior art FESS procedures, a total uncinectomy (e.g., removal of the uncinate process) is performed at the beginning of the procedure to allow visualization and access of the maxilary sinus ostium and/or ethmoid bulla and to permit the subsequent insertion of the regid surgical instruments. Indeed, in most traditional FESS procedures, if the uncinate process is allowed to remain, such can interfere with endoscopic visualization of the maxillary sinus ostium and ethmoid bulla, as well as subsequent dissection of deep structures using the available rigid instrumentation.

More recently, new devices, systems and methods have been devised to enable the performance of FESS procedures and other ENT surgeries with minimal or no removal or modification of normal anatomical structures. Such new methods include, but are not limited to, uncinate-sparing balloon sinuplasty procedures and uncinate-sparing ethmoidectomy procedures using catheters, non-rigid instruments and advanced imaging techniques (Acclarent, Inc., Menlo Park, Calif.). Examples of these new devices, systems and methods are described in incorporated U.S. patent application Ser. No. 10/829,917 entitled Devices, Systems and Methods for Diagnosing and Treating Sinusitis and Other Disorders of the Ears, Nose and/or Throat, issued as U.S. Pat. No. 7,654,997 on Feb. 2, 2010; Ser. No. 10/944,270 entitled Apparatus and Methods for Dilating and Modifying Ostia of Paranasal Sinuses and Other Intranasal or Paranasal Structures, published as U.S. Pub. No. 2006/0004323 on Jan. 5, 2006, now abandoned; Ser. No. 11/116,118 entitled Methods and Devices for Performing Procedures Within the Ear, Nose, Throat and Paranasal Sinuses filed Apr. 26, 2005, issued as U.S. Pat. No. 7,720,521 on May 18, 2010 and Ser. No. 11/150,847 entitled Devices, Systems And Methods Useable For Treating Sinusitus filed on Jun. 10, 2005, issued as U.S. Pat. No. 7,803,150 on Sep. 28, 2010, of which this application is a continuation-in-part.

There remains a need for further development of new and different devices and methodology for surgical treatment of sinusitis and other ear, nose and throat disorders.

SUMMARY OF THE INVENTION

The present invention provides apparatus and methods for treating sinusitis and other disorders of the ear, nose, throat and paranasal sinuses. The various devices and methods of the present invention may be used separately or in any possible and desirable combinations with each other.

In accordance with the invention, there is provided endoscopic guide systems that generally comprise tubular guides (e.g., rigid, flexible and/or malleable guide catheters) that incorporate or are attachable to endoscopic apparatus. The endoscopic apparatus is useable to enable endoscopically view areas ahead of or adjacent to the distal end of the tubular guide. In some embodiments, such endoscopic guide systems are useable to facilitate trans-nasal advancement of a guidewire, catheter, instrument or other device to a position within or near an opening or a paranasal sinus (e.g., any trans-nasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.). To facilitate this, the endoscopic guide system may comprise a) a tubular guide having a proximal end, a distal end and a lumen that extends longitudinally therethrough, said tubular guide having a distal portion that is more flexible than the remainder of the guide and said tubular guide being configured such that it may be i)

inserted, distal end first, through a nostril of the subject's nose and ii) advanced, without requiring substantial modification or removal of any normal anatomical structure, to a position where the distal end of the guide is within or adjacent to the ostium of the paranasal sinus; and b) an endoscopic device incorporated in or attached to the tubular guide, said endoscopic device being useable to view a visual field that includes an area beyond the distal end of the tubular guide. In some embodiments, a portion (e.g., a distal portion) of the tubular guide may be curved and the endoscopic apparatus may allow to user to essentialy see around the curve. The endoscopic apparatus may comprise a rigid, flexible, deflectable or steerable endoscope that is incorporated into, inserted into or through, or attached to the tubular guide. Or, the endoscopic apparatus may comprise a waveguide, periscope or other device that serves as an extension of a separate endoscope such that the endoscope may be connected (e.g., attached, inserted, coupled or otherwise associated) to the proximal end of the endoscopic apparatus and will receive an image from the distal end of the endoscopic apparatus.

Further in accordance with the invention, there are provided seeker devices that are useable to locate or access structures within the ear, nose and throat. In some embodiments, these seeker devices have lumens extending therethrough. In such embodiments having lumens, guidewires may be inserted or advanced through the lumen, thereby providing seeker/guidewire systems that are useable for placing guidewires into various anatomical structures (e.g., into a paranasal sinus). In embodiments having lumens, the proximal end of the seeker device may be attachable to a source of fluid for irrigation or substance delivery through the lumen and/or to a source of negative pressure to permit suction through the lumen. Also, in some embodiments that have lumens, a slot opening may extend along all or a portion of the lumen to allow a guidewire or other elongate device to be extracted laterally from all or a portion of the lumen. Additionally or alternatively, in some embodiments, the seeker device may have an expandable member (e.g., a balloon) that is useable to dilate anatomical structures, anchor the seeker and/or for other purposes. Structurally, a seeker device of the present invention may comprise an elongate substantially rigid (e.g., straight, pre-shaped, bent, curved, malleable) shaft, optionally having a bulbous (e.g., enlarged) distal tip on one or both ends, Various curves may be formed or formable in the seeker shaft.

Still further in accordance with the invention, there are provided dilator devices (e.g., balloon dilators) that may be used to dilate anatomical structures within the ear, nose or throat of a human or animal subject (e.g., opening of paranasal sinuses as defined hereabove, metal passageways, other openings or passages). Such dilator devices may comprise a) a handpiece, b) an elongate shaft that extends from the handpiece, such elongate shaft having a distal portion that is insertable through a nostril of the subject's nose, c) a dilator having a non-expanded configuration and an expanded configuration and a dilator expansion control or trigger apparatus on or associated with the handpiece, such dilator expansion control or trigger apparatus being useable to move the dilator between its non-expanded configuration and its expanded configuration. In some embodiments, the dilator may be advanceable (or advanceable/retractable) from the elongate shaft. In such embodiments having an advanceable or advanceable/retractable dilator, the handpiece may additionally have a dilator advancement control or trigger. In some designs of these devices, the handpiece, dilator expansion control or trigger and/or dilator advancement control or trigger may be operable by one hand, thereby leaving the operators other hand free for handling other instruments or performing other tasks. In embodiments where the dilator comprises a balloon, the expansion of the dilator may result for the provision of a flow of infusion fluid into the balloon. Accordingly, such devices may incorporate pumps and/or sources of pressurized inflation fluid to facilitate inflation of the balloon. The balloon may be compliant or non-compliant. In embodiments having non-compliant balloons, the device may additionally comprise apparatus for applying negative pressure to the balloon thereby evacuating and collapsine the non-compliant balloon.

Further still in accordance with the invention, there are provided devices for deterring unwanted movement of catheter(s) or other device(s) (e.g., guidewires, endoscopes, dilators, etc.) that have been inserted into the nose of a human or animal subject. Such support device may generally comprise a support member (e.g., an elongate body) that is positionable adjacent to the subject's nose and an attachment substance or apparatus (e.g., adhesive, resilient or pliable projections, fingers, members, hook and loop connector material, other apparatus for frictional engagement, etc.). The attachment substance or apparatus is useable for releaseably holding the catheter(s) or other device(s) in substantially fixed position relative to the support member. Additionally, these devices may comprise positioning apparatus (e.g., legs, brackets, holders, adhesive) for holding the support member in position adjacent to the subject's nose.

Still further in accordance with the invention, there are provided balloon catheters that are constructed in new ways. Such balloon catheters have guidewire lumens that extend though some or all of the length of the catheter. In some embodiments, an optional slot opening may be formed along some or all of the length of the guidewire lumen to allow a guidewire or other device to be extacted laterally from all oft part of that lumen.

Further still in accordance with the invention, there are provided balloon folding tools that are useable to facilitate folding of catheter-mounted balloons, such as non-compliant balloons. A baloon folding tool of this invention may comprise a) a rigid body having a central bore formed therein, the central bore having a diameter that is less than the fully inflated balloon diameter, b) a plurality of side channels located adjacent to and substantially parallel with the central bore, each of such side channels being connected to the bore through a slot. The balloon is insertable into the central bore while in a less than fully inflated state. Thereafter the balloon is inflatable to a fully or partially inflated state causing a separate portion of the balloon to pass through the each slot and into each side channel. Thereafter the balloon is deflatable such that each separate portion of the balloon that has passed into each side channel will form a separate wing of the deflated balloon. Those wings are, thereafter, foldable to a collapsed shape.

Even further in accordance with the invention, there are provided apparats for compressing balloons to a low profile to facilitate subsequent insertion or reinsertion of the balloon into the body of a human or animal subject. Such a balloon compression apparatus may comprise a plurality of compression members disposed radially about a central cavity, such compression members being spaced apart from each other such that gaps exist between adjacent compression members, such compression members being moveable from non-compressing positions to compressing positions. The balloon is insertable into the central cavity of the compression device while the compression members are in their non-compressing positions. The compression members are then moveable to their compressing positions, thereby compressing portions of the balloon causing any inflation fluid to be forced out of the balloon and causing portions of the balloon to protrude outwardly into the gaps between the compression members. This results in the formation of a plurality of wings on the deflated balloon, such wings being thereafter foldable into a collapsed shape.

Still further in accordance with the invention, there are provided inflator handpiece devices that are attachable to balloon catheters or other balloon equipped devices (e.g., balloon equipped tubular guides, seekers, guidewires, etc, as described herein and elsewhere) and useable to inflate the balloon. An inflator handpiece of the present invention may comprise a) a handpiece body configured to be grasped by a human hand, such handpiece body being attachable to the proximal end of a balloon catheter or other balloon equipped device, b) an inflator (e.g., a pump or source of compressed inflation fluid) and an inflation trigger useable to cause the inflator to inflate the balloon. These handpieces may facilitate precise handling and positioning of balloon catheters and other balloon equipped devices. In some embodiments, the handpiece may comprise and elongate body having a grip member that extends at an angle from the elongate body (e.g., generally similar to a pistol grip type of arrangement). In some embodiments, the handpiece and inflation trigger may be configured to be useable by a single hand, thereby freeing the operators other hand for handling of other instruments or performing other tasks. In embodiments where the catheter or other balloon equipped device has a lumen useable for passage of a guidewire or other device or substance, the inflator handpiece device may incorporate a port or passage to permit a guidewire or other device to be advanced through that lumen and/or to permit fluids to be infused or suction applied through that lumen. Various valves, grippers, etc. may be associated with such passageway or port to provide hemostasis, prevent fluid leakage, deter unwanted movement of guidewires or devices, etc.

Further yet in accordance with the present invention, there are provided devices for breaking nasal turbinates or other bony anatomical structures in a human or animal subject. Such a breaking device may comprise a) first and second members positionable at spaced apart positions on one side of the turbinate or bony structure and a third member positionable on the other side of the turbinate or bony structure, between the first and second members. The third member and/or said first and second members are then moveable to exert pressure on the nasal turbinate or bony structure to cause the bone of the nasal turbinate or bony structure to break.

Still further in accordance with the invention, there are provided navigation adapters that are attachable to cannulae, catheters or elongate devices to facilitate their use in conjunction with navigation systems (e.g., optical, electromagnetic, etc.) of the type used in performing image guided surgery. Such navigation adapter may comprise a) an elongate adapter body that is attachable to the substantially rigid cannula, catheter or elongate device and b) apparatus useable by the image guidance system to determine the position of the substantially rigid cannula, catheter or elongate device within the body of a human it animal subject. The apparatus useable by the image guidance system may comprise various sensors, emitters, reflectors, transponders, reflective passive elements, light emitting diodes, transmitters or receivers of energy (e.g. optical energy, radiofrequency energy, etc.) or combinations thereof that are useable to enable a navigation system to track the position of catheter, cannula or other device within the body. Examples of commercially available navigation systems that may be useable in conjunction with these navigation adapters include but are not limited to (insert list from navigation application).

Still further in accordance with the invention, there are provided methods for using the above summarized devices.

Further yet in accordance with the present invention, there are provided methods where one or more anatomical structures (e.g. uncinate process, wall of ethmoid air cell, turbinate) and/or pathological structures (e.g., polyps, etc) are removed or modified in combination with a procedure where a dilator is inserted transnasally and used to dilate an opening of a paranasal sinus (as defined hereabove) or other anatomical structure within the ear, nose, throat or paranasal sinus of a human or animal subject. Such removal or modification of normal or pathological anatomical structures may facilitate visualization and/or access to various anatomical locations during and after the procedure.

Still further in accordance with the invention, there is provided a nasal introducer that comprises an introducer body (e.g., a plug) that insets into the nostril of a human or animal subject. One or more lumen(s) (e.g., passageway(s) or bore(s)) extend through the introducer body to allow one or more catheters or other devices (e.g., endoscopes, dilators, seekers, tubular guides, etc.) to be advanced through the introducer and into the nasal cavity or beyond. Various valves, grippers, etc. may be associated with such lumen(s) to provide hemostasis, prevent fluid leakage and/or deter unwanted movement of catheters or other devices that have been inserted through the lumen(s).

Further aspect, elements and advantages of the present invention will be understood by those of skill in the art upon reading of the detailed description set forth herebelow.

BRIEF DESCRIPTION OF THE DRAWINGS

FIGS. 3-3A show an embodiment of a nasal introducer that is insertable in to nares of a human or animal subject and useable to facilitate subsequent insertion and handling of catheters and other devices.

FIG. 4A shows a perspective view of an embodiment of a guidewire comprising an enlarged distal end.

FIG. 4B shows a longitudinal sectional view of an embodiment of a guidewire comprising an anchoring balloon.

FIG. 5A shows a cross sectional view of a first embodiment of a seeker device having a lumen.

FIG. 5B shows a perspective view of a second embodiment of a seeker device having a lumen.

FIG. 5C shows a cross section of the seeker in FIG. 5B through the plane 5C-5C.

FIG. 5D shows a cross sectional view of a third embodiment of a seeker device comprising a lumen.

FIGS. 7A-7C show a method for advancing a guidewire or other device through the working lumen of an endoscope into an anatomical opening viewed by the endoscope.

FIG. 11 shows a side-deflecting distal tip that may be formed on or attached to a tubular cannula or catheter.

FIG. 12 shows the distal portion of a guide catheter having a plurality of lumens through which guidewires or other devices may be introduced on different trajectories.

FIG. 12A is a cross sectional view through line 12A-12A of FIG. 12.

FIG. 14B' is a view of the distal portion of the tubular guide device of FIG. 14B showing details of the curve formed therein.

FIG. 14C' is a view of the distal portion of the tubular guide device of FIG. 14C showing details of the curve formed therein.

FIG. 14D' is a view of the distal portion of the tubular guide device of FIG. 14D showing details of the curve formed therein.

FIG. 14E' is a view of the distal portion of the tubular guide device of FIG. 14E showing details of the curve formed therein.

FIG. 19 shows a partial perspective view of the distal region of another balloon catheter that has capacitance measuring means for real time determination of balloon diameter.

FIG. 19A shows a side view of the distal region of the balloon catheter of FIG. 21.

FIG. 19B is a cross sectional view through line 19B-19B of FIG. 19A.

FIG. 19C is a cross sectional view through line 19C-19C of FIG. 19A.

FIG. 20 shows a partial perspective view of the distal region of another balloon catheter that has capacitance measuring means for real time determination of balloon diameter.

FIG. 20A shows a side view of the distal region of the balloon catheter of FIG. 20.

FIG. 20B is a cross sectional view through line 20B-20B of FIG. 20A.

FIG. 20C is a cross sectional view through line 20C-20C of FIG. 20A.

FIG. 23 shows a partial perspective view of a balloon folding tool of the present invention.

FIG. 23A shows a balloon catheter being inserted into the baloon folding tool of FIG. 23.

FIG. 23B shows a cross sectional view of the balloon folding tool of FIG. 23 with a fully deflated/collapsed balloon positioned therein.

FIG. 23C shows a cross sectional view of the balloon folding tool of FIG. 23 with a balloon partially inflated therein such that portions of the balloon protrude into side channels.

FIG. 23D shows a deflated/collapsed balloon after removal from the baloon folding tool of FIG. 23.

FIG. 24A is an exploded view of the balloon compressing apparatus of FIG. 24.

FIG. 26A is a perspective view of the navigation adaptor device of FIG. 26 attached to the proximal end of a guide tube of the present invention and having an optical navigation assembly mounted on the navigation adapter device.

FIG. 26B is a perspective view of the navigation adaptor device of FIG. 26 attached to the proximal end of a guide tube of the present invention and having an electromagnetic navigation assembly mounted on the navigation adapter device.

FIG. 27A is a top view of a dilation device useable to dilate the ostia of paranasal sinuses and other anatomical passages within the ear, nose and throat.

FIG. 27B is a side view f the device of FIG. 27A.

FIGS. 29C-D show steps in a method for temporarily or permanently breaking or deforming a nasal turbinate using the squeezing device of FIG. 29.

FIG. 29E shows a broken perspective view of a twistable device that is useable to break or deform anatomical structures such a nasal turbinates.

FIGS. 29F-G show steps in a method for temporarily or permanently breaking or deforming a nasal turbinate using the twisting device of FIG. 29E.

DETAILED DESCRIPTION

The following detailed description, the accompanying drawings and the above-set-forth Brief Description of the Drawings are intended to describe some, but not necessarily all, examples or embodiments of the invention. The contents of this detailed description do not limit the scope of the invention in any way.

A number of the drawings in this patent application may show anatomical structures of the ear, nose and throat. In general, these anatomical structures are labeled with the following reference letters:

| | |
|---|---|
| Nasal Cavity | NC |
| Nasopharynx | NP |
| Nasal Turbinate | NT |
| Frontal Sinus | FS |
| Frontal Sinus Ostium | FSO |
| Ethmoid Sinus | ES |
| Ethmoid Air Cells | EAC |
| Sphenoid Sinus | SS |
| Sphenoid Sinus Ostium | SSO |
| Maxillary Sinus | MS |
| Maxillary sinus ostium | MSO |
| Mucocyst | MC |
| Middle turbinate | MT |
| Inferior turbinate | IT |
| Uncinate | UN |
| Suprabullar ostium/recess | SO |
| Retro-bullar ostium/recess | RO |

The devices disclosed herein may be used alone or in various combinations to perform various procedures including, but not limited to, various transnasal procedures within paranasal sinuses and/or within openings of paranasal sinuses. As used herein, unless specified otherwise, the term "opening(s) of paranasal sinus(es)" shall include any transnasally accessible opening in a paranasal sinus or air cell including but not limited to; natural ostia, natural canals, surgically altered natural ostia, surgically created openings, antrostomy openings, ostiotomy openings, burr holes, drilled holes, puncture tracts, ethmoidectomy openings, fenestrations and other natural or man made passageways.

Figure 1:
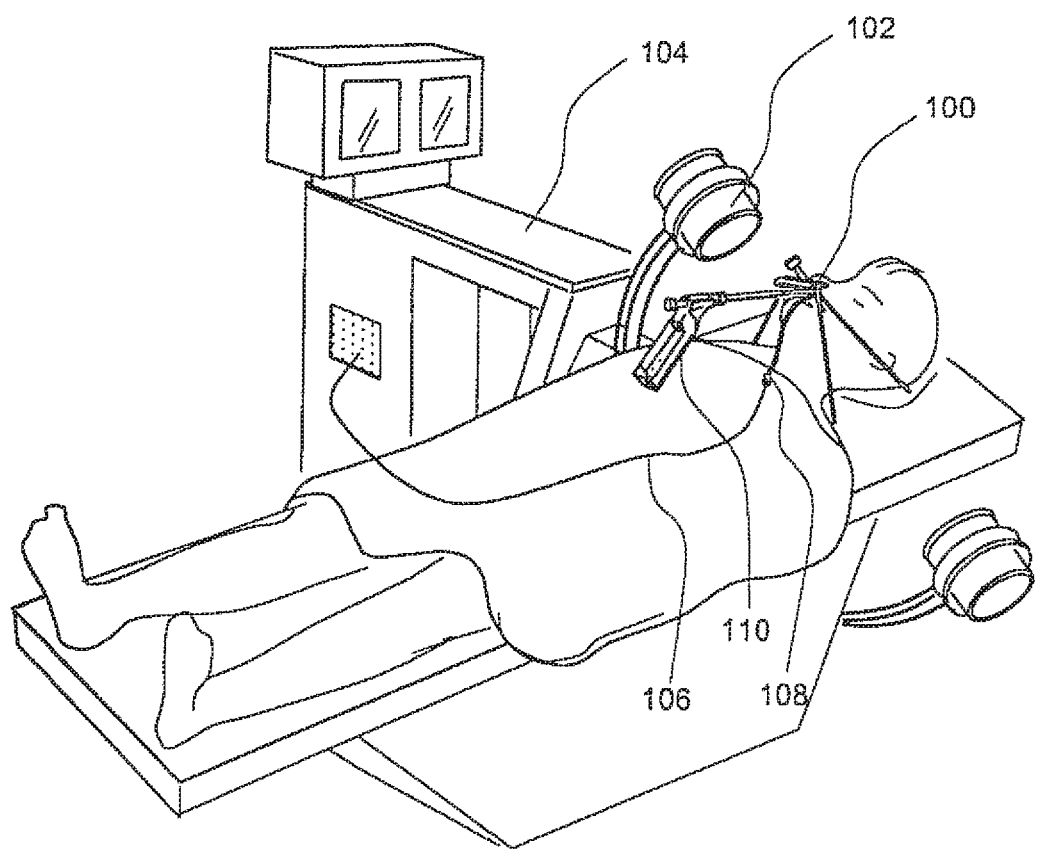
FIG. 1 is a perspective view of a human subject undergoing a procedure for treating sinusitus in accordance with the present invention.

FIG. 1 shows a human subject undergoing a procedure for treating sinusitis in accordance with one particular example of the present invention. The human subject is subjected to one or more diagnostic, therapeutic or access devices introduced through a support device 100. One example of a therapeutic device is a balloon catheter used to dilate openings of paranasal sinuses or other endonasal anatomical structures. One example of an access device is a guidewire used to access dilate natural ostia of paranasal sinuses or a natural or artificial passageway or tract leading to paranasal sinuses. In the embodiment shown in FIG. 1, support device 100 comprises a support member that is stabilized by three or more legs that rest on the operating table. The one or more diagnostic, therapeutic or access devices may be tracked or navigated through the anatomy using one or more tracking or navigation modalities. In the embodiment shown in FIG. 1, a C-arm fluoroscope 102 provides fluoroscopic visualization of anatomical regions during the procedure. An instrument console 104 comprising one or more functional modules may also be provided. Instrument console 104 can be controlled by console control means e.g. a foot pedal controller, a remote controller etc. Instrument console 104 may be fitted with wheels to enable an operator to change the position of the instrument console in an operating area. Instrument console 104 may comprise functional modules including, but not limited to:

1. Suction pump for delivering a controlled amount of vacuum to a suction device,
2. Irrigation pump to deliver saline or other suitable irrigation medium,
3. Power module to supply power to drills or other electrical devices,
4. Storage modules for storing instruments, medications etc.,
5. Energy delivery module to provide radiofrequency, laser, ultrasound or other therapeutic energy to a surgical device,
6. Fluoroscope, MRI, CT, Video, Endoscope 106 or Camera or other imaging modules to connect or interact with devices used during various diagnostic or therapeutic procedures,
7. Display module e.g. a LCD, CRT or Holographic screen to display data from various modules such as an endoscope, fluoroscope or other data or imaging module,
8. Remote control module to enable an operator to control one or more parameters of one or more functional modules, and
9. Programmable Microprocessor that can store one or more operation settings for one or more functional modules etc.

In the embodiment shown in FIG. 1, instrument console 104 is connected to endoscope 106. Endoscope 106 may be introduced in the anatomy through one or more introducing devices 108 such as guide catheters. A physician may use a hand held introducer 110 comprising a surgical navigation modality to introduce one or more diagnostic, therapeutic or access devices into the anatomy. Examples of surgical navigation modalities that may be located on introducer 110 include, but are not limited to navigation modalities comprising reflective passive elements, light emitting diodes, transmitters or receivers of energy (e.g. optical energy, radiofrequency energy, etc.), a combination of tow or more of the abovementioned navigation modalities, etc.

Figure 2A:
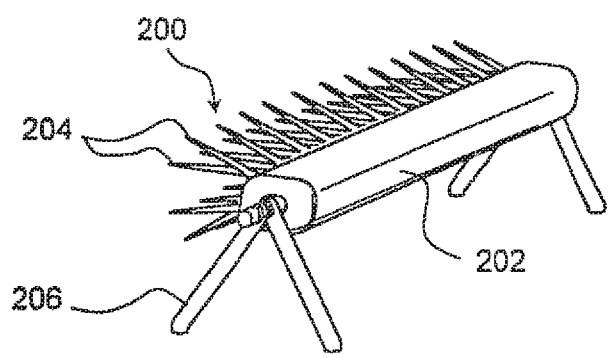
FIG. 2A shows a perspective view of an embodiment of a support device having finger members in the nature of bristles.

One or more devices disclosed herein may be supported by one or more support devices while performing diagnostic, therapeutic or access procedures on a patient. For example, FIG. 2A shows a perspective view of one embodiment of a support device 200 comprising an elongate, generally cylindrical body 202 having a plurality of projections 204 (e.g., strands, wires, bristles, pliable or resilient members, etc.) extending therefrom. Projections 204 are located sufficiently close to each other and are made of a suitable material to frictionally grip a device that has been inserted between adjacent projections 204. For example, projections 204 may be made of polymers, rubber materials including, but not limited to neoprene, silicone rubber, ABS, Nylon, PVC, Pebax, etc. Projections 204 can be used to reversibly support one or more devices while performing diagnostic, therapeutic or access procedures on a patient. In some embodiments, one or more attachment substances or apparatus may be used to attach the body 202 to a region of the patient's body such as face, head, etc; a table; a flexible, rigid or repositionable arm mounted on a support; etc. In the embodiment shown in FIG. 2A, body 202 is attached to four arms 206 that enable support device 200 to be placed on a suitable surface.

Figure 2B:
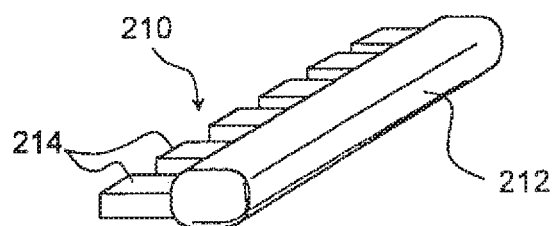
FIG. 2B shows a perspective view of an embodiment of a support device having finger members in the nature of pliable or resilient projections.

FIG. 2B shows a perspective view of another embodiment of a support device. In this example, the support device 210 comprises a and elongate body 212 having an adhesive material disposed on one or more regions of its outer surface to reversibly adhere the support device 216 to a surface, such as the patient's body, a table or a flexible arm, etc. The body 212 of this support device 210 further comprises two or more fingers 214 constructed and spaced in relation to each other to frictionally grip and substantially hold device(s) (e.g., catheter, cannula, endoscope, guidewire, etc.) that has been inserted between adjacent fingers 214. The fingers 214 may be formed of any suitable material, typically a pliable or resilient material such as certain polymer foams, elastomers, rubber materials including, but not limited to neoprene, silicone rubber, ABS, Nylon, PVC, Pebax, etc. Fingers 214 can be used to frictionally hold one or more device(s) (e.g., catheter, cannula, endoscope, guidewire, etc.) in substantially fixed position while performing diagnostic, therapeutic or access procedures on a patient. Body 212 is connected to one or more attachment mechanisms to attach body 212 to a region such as the patient's body, a table or a flexible arm, etc.

Figure 2C:
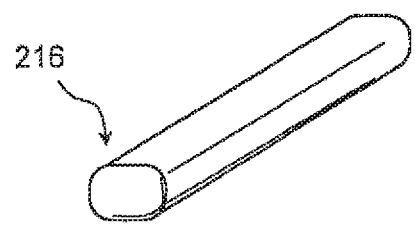
FIG. 2C shows a perspective view of an embodiment of a support device comprising an adhesive surface.

FIG. 2C shows a perspective view of another embodiment of a support device 216 comprising an elongate body having one or more regions of its outer surface coated with an adhesive material to which one or more device(s) (e.g., catheter, cannula, endoscope, guidewire, etc.) may releasably adhere. The body of this support device 216 may be made of any suitable biocompatible materials including, but not limited to silicone, nylon, DELRIN®, polycarbonate, stainless steel, ABS, etc. Typical examples of adhesives that may be disposed on the outer surface of the body to include, but are not limited to medical grade rubber pressure sensitive adhesives, acrylic adhesives such as 3M Emtech adhesive P1500™, 3M Emtech adhesive P1510™ etc. The adhesive coated regions may also be used to reversibly adhere the body of this support device 216 to another surface such as the patient's body, a table or a flexible arm, etc.

Figure 2D:
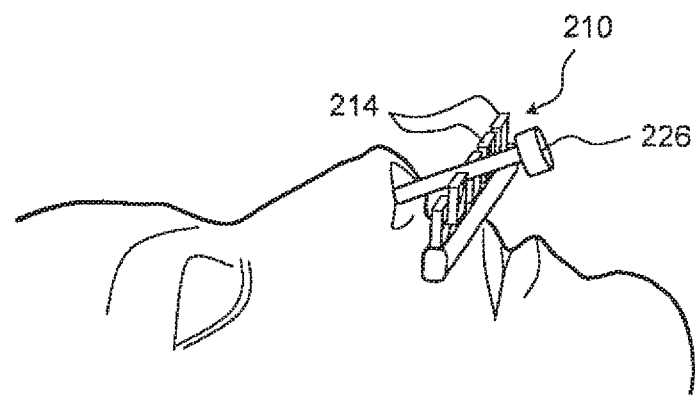
FIGS. 2D through 2G show perspective views of various embodiments of a support device being used to support a working device.

FIGS. 2D through 2G show perspective views of various embodiments of support devices being used to support working devices. In FIG. 2D, support device 210 is reversibly attached to a the patient's face. FIG. 2D also shows a guide catheter 226 introduced through the nose and supported between adjacent fingers 214 of the support device 210 with the elongate body of the support device being disposed transversely (e.g., from side to side) inferior to the subject's nose (e.g., below the nares).

Figure 2E:
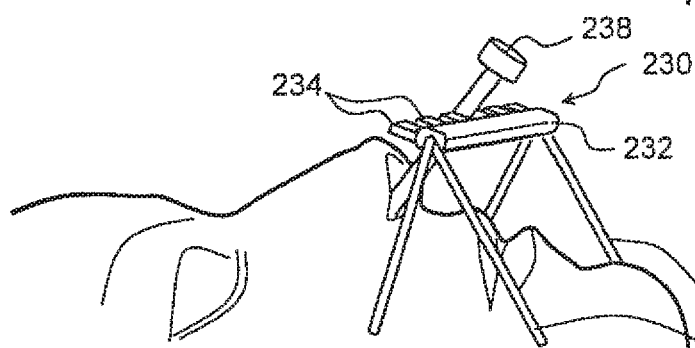

In the example of FIG. 2E, a support device 230 comprises a body 232 and two or more thin strands, wires, or bristles 234 that are connected to body 232. Bristles 234 are designed to frictionally grip a device located between adjacent bristles 234. Body 232 is connected to one or more attachment mechanisms such as arms 236 that enable support device 230 to be placed on a patient's face. In the embodiment shown in FIG. 2E, a guide catheter 238 is supported by support device 230.

Figure 2F:
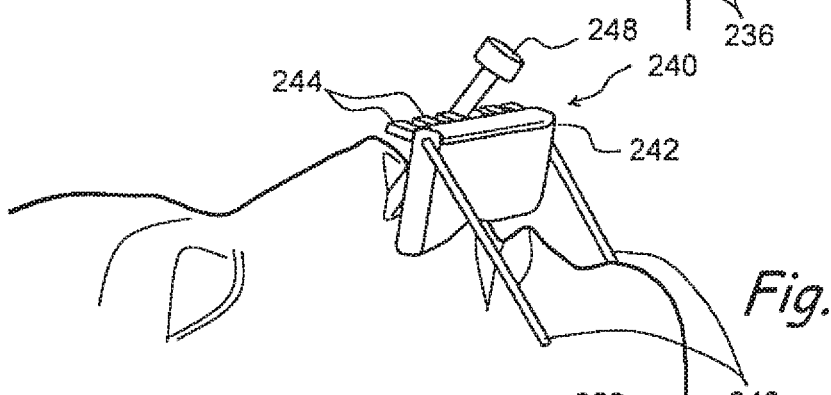

In FIG. 2F, a support device 240 comprises a body 242 and two or more thin strands, wires, or bristles 244 that are connected to body 242. One region of body 242 is in contact with a facial region of a patient. Bristles 244 are designed to frictionally grip a device located between adjacent bristles 244. Body 242 is connected to one or more attachment mechanisms such as arms 246 that enable support device 240 to be supported on a patient's face. In the embodiment shown in FIG. 2F, a guide catheter 248 is supported by support device 240.

Figure 2G:
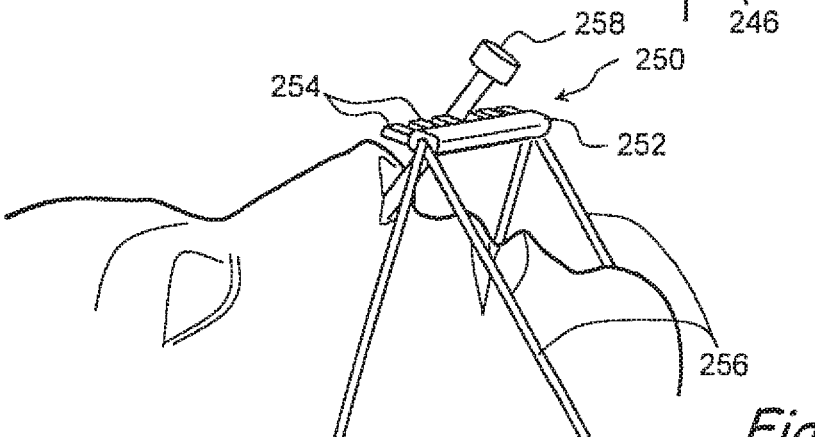

In FIG. 2G, a support device 250 comprises a body 252 and two or more thin strands, wires, or bristles 254 that are connected to body 252. Bristles 254 are designed to frictionally grip a device located between adjacent bristles 254. Body 252 is connected to one or more attachment mechanisms such as arms 256 that enable support device 250 to be placed on a mount table. In the embodiment shown in FIG. 23, a guide catheter 258 is supported by support device 250.

Similar support devices may also be designed using hook and loop fasteners such as Velcro™.

One or more devices disclosed herein may be introduced through one or more nasal introducers. Such nasal introducers may also be used for keeping catheters or devices separate from each other and/or for anchoring for deterring unwanted movement or slippage of one or more catheter or other devices that have been inserted into the nose. Such nasal introducers may also be used for plugging the nostrils to prevent leakage of fluids through the nostril. For example, FIGS. 3-3A show an embodiment of a nasal introducer that is insertable in to nares of a human or animal subject and useable to facilitate subsequent insertion and handling of catheters and other devices. FIG. 3 shows a perspective view of an embodiment of the nasal introducer 300 comprising a body having a proximal region, a distal region and one or more lumens or bores extending therethrough to permit insertion of the desired device(s). The outer diameter of proximal region is larger than the outer diameter of the distal region. The outer diameter of nasal introducer 300 gradually reduces or tapers in the distal direction, as shown in FIG. 3, This nasal introducer 300 is placed in a nostril and one or more diagnostic, therapeutic or access devices may be introduced through nasal introducer 300. Examples of such diagnostic, therapeutic or access devices include, but are not limited to guide catheters, guidewires, endoscopes, etc. In the example shown in FIGS. 3 and 3A, the nasal introducer 300 has two lumens, a first device introducing lumen 302 and a second device introducing lumen 304. The proximal end of first device introducing lumen 302 emerges out of the proximal end of nasal introducer 300 through a first opening 306. The distal end of first device introducing lumen 302 emerges out of the distal end of nasal introducer 300 through a second opening 307. Similarly, the proximal end of second device introducing lumen 304 emerges out of the proximal end of nasal introducer 300 through a third opening 308. The distal end of second device introducing lumen 304 emerges out of the distal end of nasal introducer 300 through a fourth opening 309. In one embodiment, first opening 306 and third opening 308 are provided with a locking mechanism such as a rotating hemostasis valve. The locking mechanism can be used to anchor one or more devices being introduced through nasal introducer 300 to the nose. Nasal introducer 300 may be made of suitable biocompatible materials including, but not limited to rubber, polymers, metals, etc.

FIG. 4A shows a side view of an embodiment of a guidewire comprising an enlarged distal end. Guidewire 400 comprises an elongate body 402. Elongate body 402 may be made of a variety of biocompatible materials including, but not limited to stainless steel, Nickel-titanium alloy (e.g., Nitinol), etc. Elongate body 402 may be coated with a variety of guidewire coatings including, but not limited to lubricious coatings such as PTFE coatings, etc. The distal end of elongate body 402 comprises an enlarged region 404. In one embodiment, enlarged region 404 is substantially spherical in shape. The length of elongate body 402 may range from 65 to 75 cm. The distal region of guidewire 400 may comprise a curved, bent or angled region. In one embodiment, the distal region of guidewire 400 comprises a J-tip.

In some method embodiments of the invention disclosed herein, a guidewire may be inserted into a paranasal sinus or into/near the opening of a paranasal sinus and, thereafter, one or more diagnostic or therapeutic devices may be introduced over the guidewire. In some instances, forces generated during introduction of devices over the guidewire may tend to cause the position of the guidewire to change. The forces may also cause the guidewire to get dislodged from a desired position in a paranasal sinus or opening of a paranasal sinus. To prevent such unwanted movement of the guidewire, one or more anchoring or occlusion apparatus may be present on the guidewire. For example, FIG. 4B shows a longitudinal sectional view of a guidewire 410 having an elongate body 412, a lumen 414 and a balloon 416 or other inflatable member that may be used to anchor the distal end of the guidewire 410 or for other purposes (e.g., dilation). Elongate body 412 may be made of a variety of biocompatible materials including, but not limited to stainless steel, Nickel-titanium alloy (e.g., Nitinol), etc. In one embodiment, elongate body 412 is made of a suitable hypotube. Elongate body 412 may be coated with a variety of guidewire coatings including, but not limited to lubricious coatings such as PTFE coatings, etc. The outer diameter of elongate body 412 may range from 0.014 inches to 0.040 inches. In a preferred embodiment, the outer diameter of elongate body 412 is 0.035 inches. Elongate body 412 comprises a lumen 414. The distal end of lumen 414 is in fluid communication with an anchoring balloon 416. Anchoring balloon 416 may be made of a compliant, semi-compliant or non-compliant material. Anchoring balloon 416 may be present on the distal end of elongate body 412 or on the distal region of elongate body 412. The proximal region of elongate body 412 may comprise a microvalve located in lumen 414. The microvalve allows a user to inflate or deflate anchoring balloon 416 and also provide a fluid seal to lumen 414 when guidewire 410 is used to perform a diagnostic or therapeutic procedure. The distal region of guidewire 400 may comprise a curved, bent or angled region. In one embodiment, the distal region of guidewire 400 comprises a J-tip. In one embodiment of a method of using guidewire 400, distal end of guidewire 400 is introduced into an anatomical region such as a paranasal sinus with anchoring balloon 416 deflated. Thereafter, anchoring balloon 416 is inflated. Guidewire 400 is then pulled in the proximal direction to anchor anchoring balloon 416 in the ostium of the paranasal sinus. Thereafter, guidewire 400 is used to perform a diagnostic or therapeutic procedure. It will be appreciated that, as an alternative to a balloon 416, other anchoring apparatus such as deployable projections or expandable polymer or metal mesh structures may be incorporated into or on the guidewire 410.

Various diagnostic, therapeutic or access devices disclosed herein may be introduced in the anatomy through a seeker. FIG. 5A shows a seeker device 500 that comprises an elongate body 502 having a lumen 506 extending therethrough. The elongate body 502 can be made of suitable biocompatible material(s) including, but not limited to metals e.g. stainless steel, titanium, nickel-titanium alloy (e.g., Nitinol), etc.; polymers e.g. Pebax, PEEK, Nylon, polyethylene, etc. Some or all of the elongate body 502 may be bent, angled, curved or malleable. The distal end of elongate body 502 may comprise a tip structure 504. Such tip member 504 may be constructed to be substantially atraumatic so as to prevent or reduce damage to adjacent anatomy while using seeker 500. In the embodiment shown in FIG. 5A, tip structure 504 comprises an enlarged, substantially spherical or bulbous region. Lumen 506 extends from the proximal end of elongate body 502 and to the distal end of the device. The lumen 506 can be used for introducing one or more elongate devices, suctioning, introducing one or more fluids, etc. The proximal end of elongate body 502 may comprise a suitable hub such as a luer lock. Seeker 500 may be introduced through an opening in the human body to determine the location of a cavity, sinus or other anatomical regions. Thereafter, one or more elongate devices such a guidewires may be inserted through lumen 506 and into the cavity, sinus or other anatomical regions. In one method embodiment, seeker 500 is inserted through the nose into the nasal cavity. Thereafter, seeker 500 is advanced such that optional tip structure 504 is located near a target anatomy e.g. an opening of a paranasal sinus. Seeker 500 is then moved by the user such that atraumatic tip 504 engages with the target anatomy. This provided the user information about the location and orientation of the target anatomy such as an ostium or passageway leading to a paranasal sinus. Seeker 500 is then used to introduce a guidewire through lumen 506 into the paranasal sinus. Thereafter, seeker 500 is removed leaving the guidewire in place. The guidewire is then used to introduce one or more diagnostic or therapeutic devices into the paranasal sinus. In another method embodiment, an endoscope may be incorporated within or introduced through lumen 506 and used to visualize anatomical structures and/or to guide the navigation of seeker 500. Optionally, a dilator (e.g., a balloon) may be mounted on the seeker 500 at or near the distal end of the device and may be used to dilate structures into which the seeker device 500 has been inserted. In instances where a balloon or other inflatable dilator is used, a second lumen may extend through the shaft 502 terminating distally in an opening within the balloon to permit inflation/deflation of the balloon.

FIGS. 5B-C show a second embodiment of a seeker device 510 comprising an elongate body 512 having a lumen 518 extending therethrough from end to end. Elongate body 512 can be made of suitable biocompatible materials including, but not limited to metals e.g. stainless steel, titanium, Nickel-titanium alloy (e.g., Nitinol), etc.; polymers e.g. Pebax, PEEK, Nylon, polyethylene, etc. The distal region of elongate body 512 may comprise a bent, angled or curved region. In some embodiments, some (e.g., a distal region) or all of the elongate body 512 may be substantially curved or malleable. The distal end of elongate body 512 may, in some cases, comprise an atraumatic tip 514 to prevent or reduce damage to adjacent anatomy while using seeker 510. In the embodiment shown in FIG. 5B, atraumatic tip 514 comprises an enlarged, substantially spherical region. The proximal region of elongate body 512 may comprise a handle 516 to enable a user to advance and/or twist seeker 510. In the particular example of FIG. 5B, the lumen 518 extends from the proximal end of elongate body 512 to through distal end of the atraumatic tip 514. Also, in this particular example, the elongate body 512 further comprises a longitudinal slit 520 that extends into lumen 518. The proximal end of elongate body 512 may comprise a suitable hub such as a luer lock. In one method of use, this seeker 510 may be inserted through the nose into the nasal cavity. Thereafter, seeker 510 is advanced such that atraumatic tip 514 becomes positioned near a target anatomy e.g. an ostium of a paranasal sinus. Seeker 510 is then moved by the user such that its atraumatic tip 514 touches adjacent anatomical structures. This provides the user with information about the location and orientation of the target anatomy and/or surrounding anatomical structures. In some applications, after the atraumatic tip 514 of the seeker 510 has been inserted into or through an ostium of a paranasal sinus, a guidewire may be advanced through lumen 518 into the paranasal sinus. Thereafter, the seeker 510 may be removed leaving the guidewire in place. To facilitate removal of the seeker 510 while leaving the guidewire in place, the proximal portion of the guidewire may be extracted laterally through slit 520. After the seeker 510 has been removed, the guidewire may be used to introduce one or more working devices (e.g., diagnostic or therapeutic devices) into the paranasal sinus. In some applications, an endoscope is introduced through lumen 518 to guide the navigation of seeker 510. FIG. 5D shows Another seeker 530 comprising an elongate body 532 having a lumen 534 extending therethrough. The body 532 may be made of suitable biocompatible materials including, but not limited to metals e.g. stainless steel, titanium, Nickel-titanium alloy (e.g., Nitinol), etc.; polymers e.g. Pebax, PEEK, Nylon, polyethylene, etc. The distal region of elongate body 532 may comprise a bent, angled or curved region. In one embodiment, elongate body 532 is substantially malleable. Lumen 534 is an end-to-end lumen extending from the proximal end of elongate body 532 through an opening in the distal end of elongate body 532. A guidewire 536, which may optionally have an atraumatic tip 538, is loaded in lumen 534 as shown. The distal region of guidewire 636 may be curved, bent or angled such that it forms an internal angle, for example an angle of about 30 degrees, about 60 degrees, about 90 degrees, about 110 degrees, etc. The proximal end of elongate body 532 may comprise a suitable hub such as a rotating hemostasis valve to reversibly secure guidewire 536 to seeker 530. In one method embodiment, seeker 530 along with guidewire 536 is inserted through the nose into the nasal cavity. Thereafter, seeker 530 is advanced such that atraumatic tip 538 is located near a target anatomy e.g. an ostium of a paranasal sinus. Seeker 530 is then moved by the user such that atraumatic tip 538 engages with the target anatomy. This provided the user information about the location and orientation of the target anatomy. Seeker 530 is then used to advance guidewire 536 through lumen 534 into the paranasal sinus. Thereafter, seeker 530 is removed leaving guidewire 536 in place. This step is performed by sliding seeker 530 in the proximal direction over guidewire 536. Guidewire 536 is then used to introduce one or more diagnostic or therapeutic devices into the paranasal sinus.

Figure 5E:
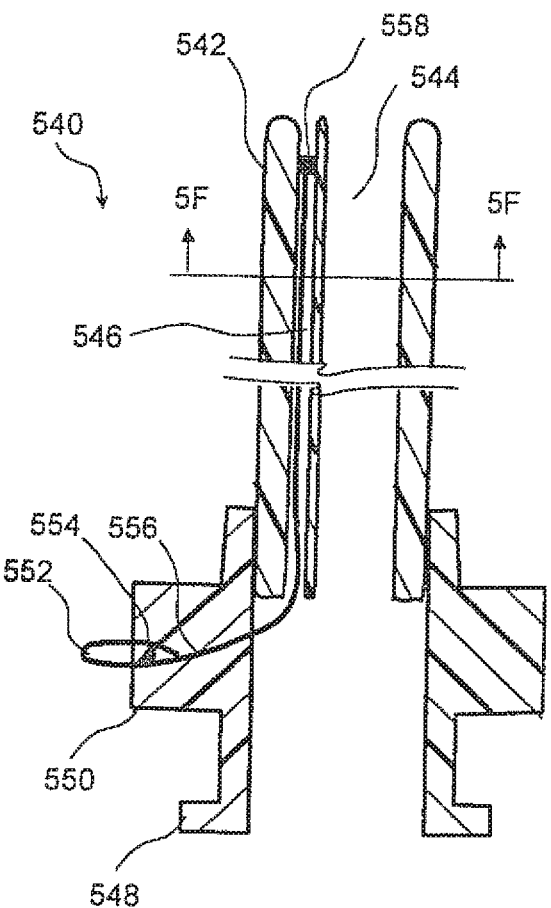
FIG. 5E shows a longitudinal section of an embodiment of a seeker device comprising a deflectable or bendable distal tip.
Figure 5F:
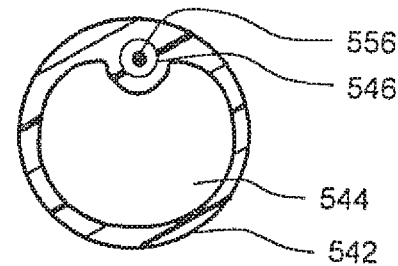
FIG. 5F shows a cross sectional view through plane 5F-5F in FIG. 5E.

Any of the seeker devices disclosed herein may comprise a deflectable or bendable distal tip. For example, FIG. 5E shows a seeker device 540 having a deflectable or bendable distal tip. Seeker 540 comprises an elongate body 542 having a first lumen 544 and a second lumen 546 extending therethrough. The elongate body 542 may be made from suitable biocompatible material(s) including, but not limited to Pebax, PEEK, Nylon, polyethylene, etc. The distal end of elongate body 542 may optionally comprise an atraumatic tip. In one embodiment, the distal end of elongate body 542 comprises an enlarged, spherical region. In the embodiment shown in FIG. 5E, the inner diameter of the first lumen 544 is larger than the inner diameter of the second lumen 546. The proximal end of elongate body 542 may be connected to a suitable hub 548, such as a female luer lock. Hub 548 may comprise one or more wings 550 to enable a user to twist or torque seeker 540. Seeker 540 further comprises a deflecting or bending mechanism. In this embodiment, the deflecting or bending mechanism comprises a deflecting handle 552 attached to a pivot 554. One end of deflecting handle 552 is connected to a pull wire 556. The distal end of pull wire 556 is attached to the distal region of elongate body 542 by an attachment means 558. In one embodiment, attachment means 558 is glue. To cause deflecting or bending of the distal tip of elongate body 542, a user pulls deflecting handle 552. Deflecting handle 552 in turn pulls pull wire 556. This causes deflecting or bending of the distal tip of elongate body 542. FIG. 5F shows a cross sectional view through plane 5F-5F in FIG. 5E. FIG. 5F shows elongate body 542 comprising first lumen 544 and second lumen 546. Pull wire 556 passes through second lumen 546. Similar deflecting mechanisms may also be used for constructing one or more guide catheters disclosed herein. Such guide catheters may be used for introducing one or more diagnostic, therapeutic or access devices into the anatomy.

Any of the seeker devices disclosed herein may be used to open or puncture scar tissue or adhesions of paranasal sinus ostia or passageways leading to paranasal sinuses. Such scar tissue or adhesions may be caused for example due to infection, prior surgery, etc.

Figure 6B:
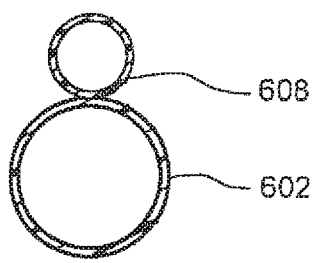
FIG. 6B is a cross sectional view through line 6B-6B of FIG. 6A.
Figure 6A:
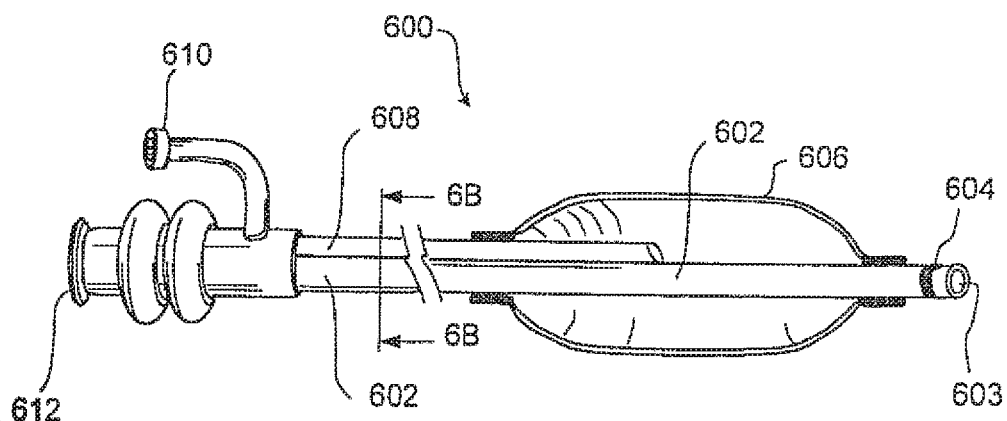
FIG. 6A is a perspectiove, partially section view of a tubular guide having a balloon.
Figure 6:
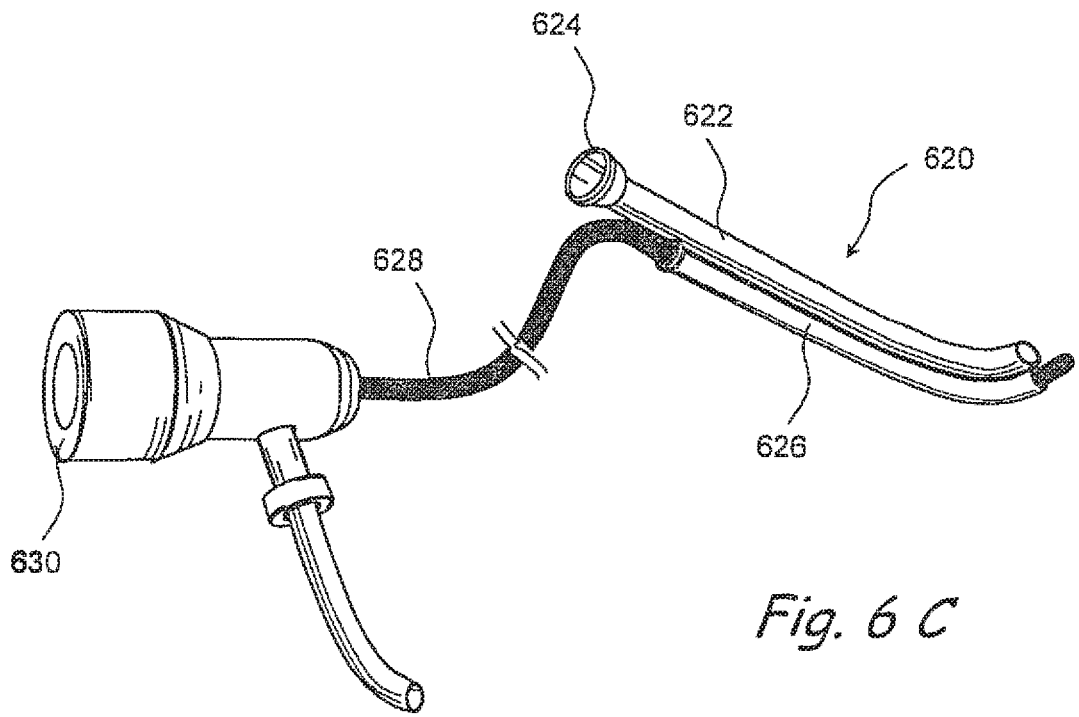
FIG. 6C shows a perspective view of a tubular guide having a separate lumen useable for insertion of an endoscope.
FIG. 6D shows a perspective view of a tubular guide having clip(s) useable for attachment of an endoscope or other apparatus.
FIG. 6E shows an embodiment of a combination endoscope and tubular guide.
FIG. 6F shows another embodiment of a combination endoscope and tubular guide.
FIG. 6G shows another embodiment of a combination endoscope and tubular guide.
FIGS. 6H and 6I show apparatus useable to hold a tubular guide and an endoscope in substantially fixed side-by-side positions.
FIG. 6J shows a perspective view of a removable clip device useable for attaching a second device (e.g., an endoscope) to a tubular guide or other elongate device.
FIGS. 6K and 6L, show steps in a method wherein the removable clip device of FIG. 6J is used to attach an endoscope to a tubular guide.
FIGS. 6M through 6O show steps of a method of introducing one or more diagnostic or therapeutic devices through a tubular guide having an associated endoscope.
FIG. 6P shows a method for introducing a dilator through a tubular guide that has an associated endoscope.
FIG. 6Q shows a perspective view of a combination endoscope/tubular guide that is bendable or deflectable.
FIG. 6R shows the distal end of the device of FIG. 6Q in a bent or deflected state.
Figure 6:
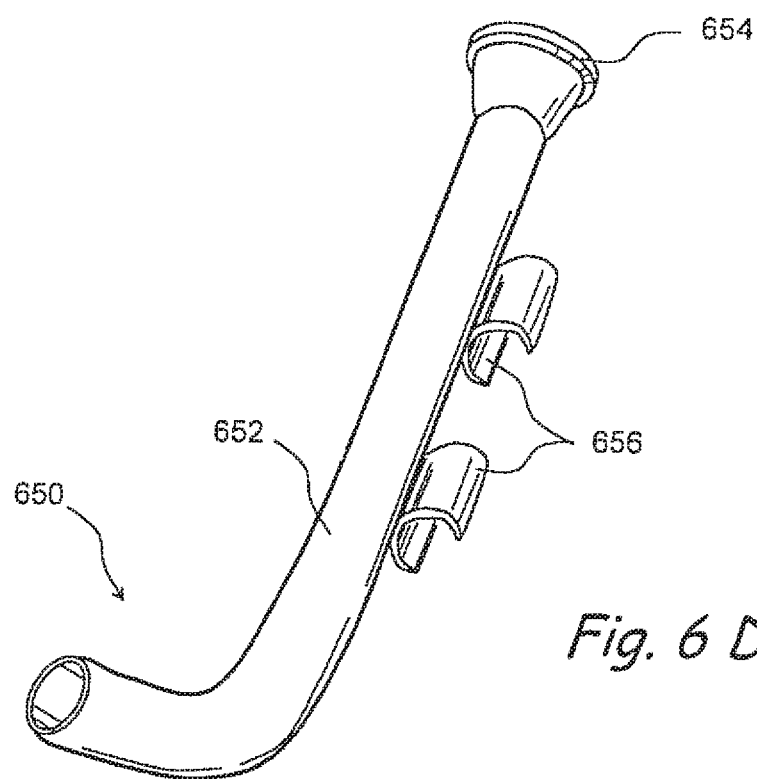
Figure 6:
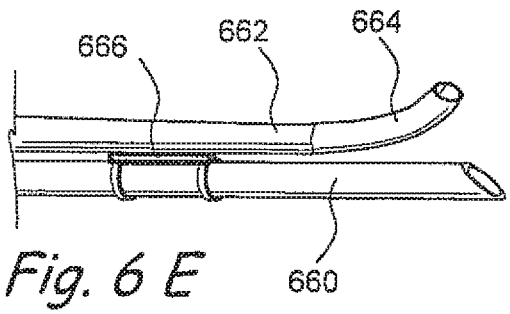
Figure 6:
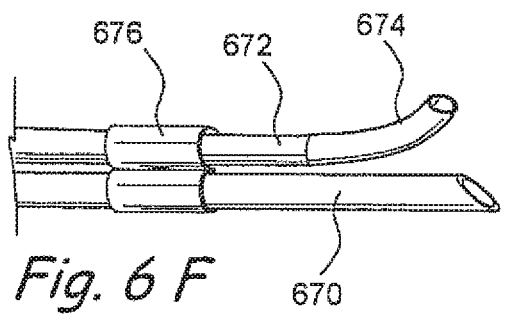
Figure 6:
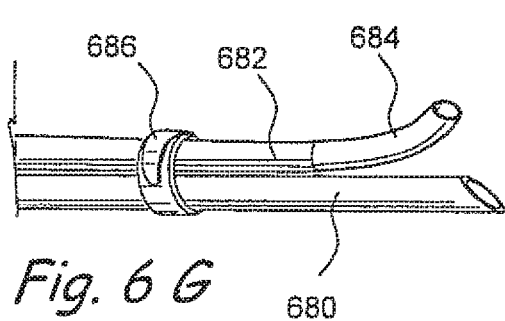
Figure 6:
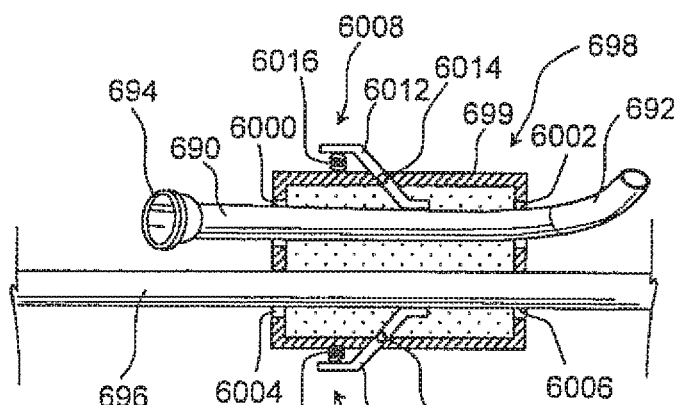
Figure 6:
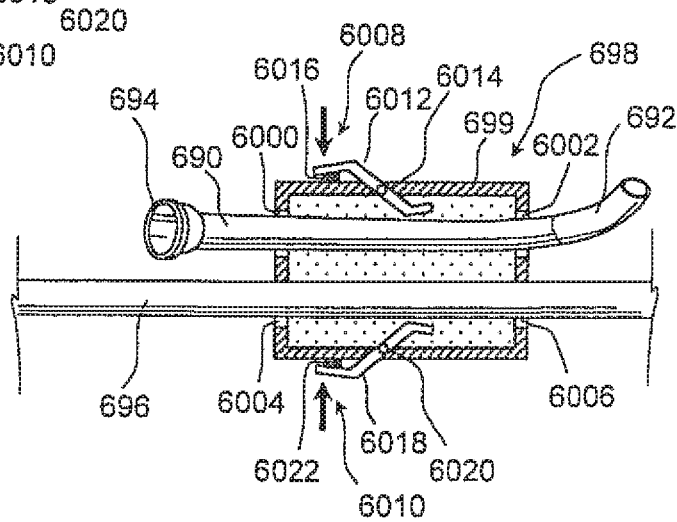
Figure 6:
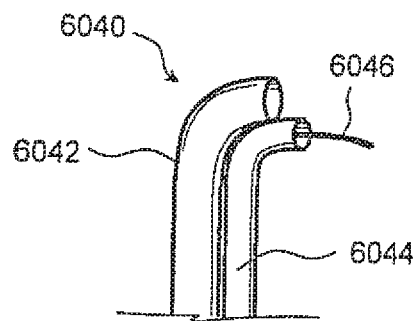
Figure 6:
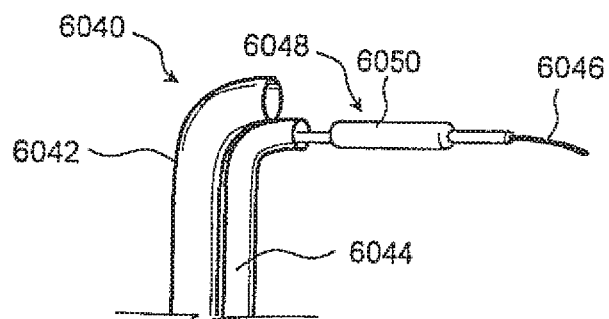
Figure 6:
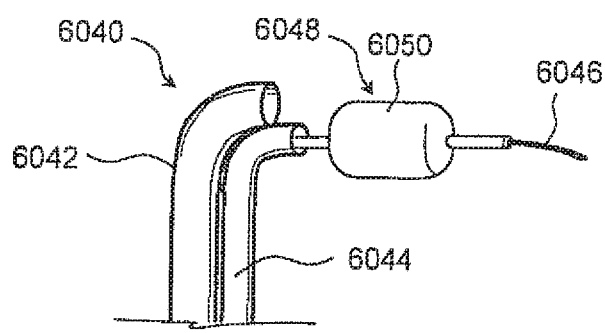
Figure 6:
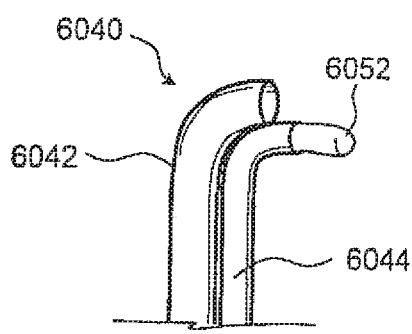
Figure 6:
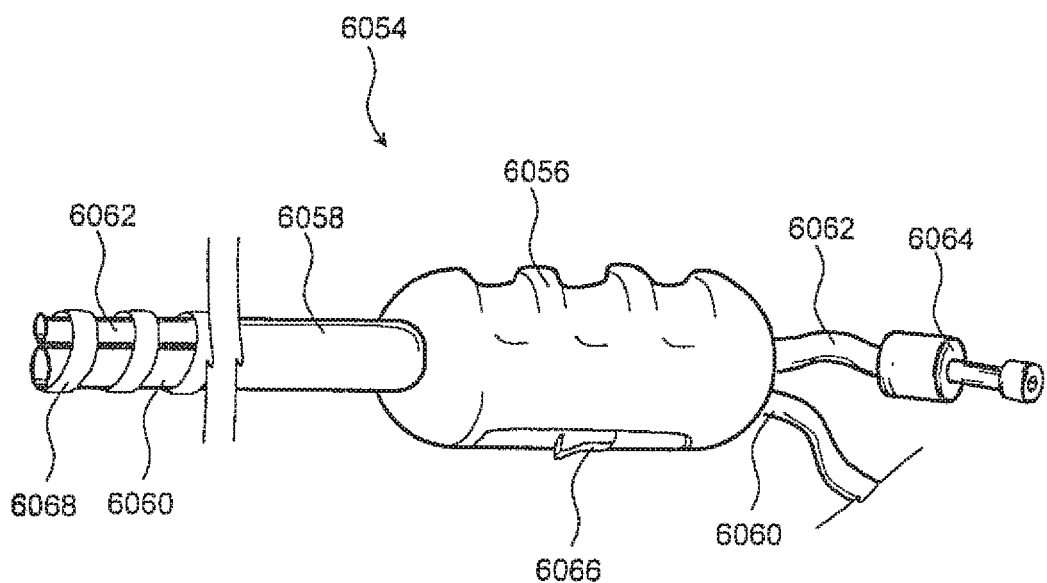
Figure 6:
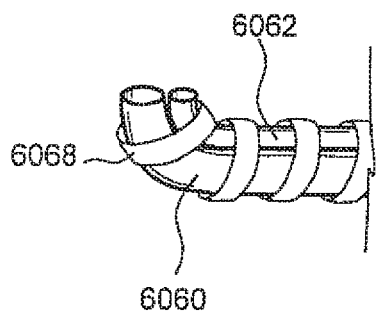

FIG. 6A shows a tubular guide or guide catheter 600 having an elongate guide shaft 602, a lumen 603 extending therethrough and an expandable dilator such as a balloon 606. Guide shaft 602 may be made of suitable biocompatible materials including, but not limited to metals e.g. stainless steel, titanium, nickel-titanium alloy (e.g., Nickel-titanium alloy (e.g., Nitinol)), etc.; polymers e.g. Pebax, PEEK, Nylon, polyethylene, etc. The distal region of guide shaft 602 may comprise an angled, curved or bent region. In one embodiment, the distal tip of guide catheter 600 comprises a soft, atraumatic tip to reduce or prevent damage to surrounding anatomy. The distal region of guide shaft 602 may comprise a navigational marker 604 such as a radiopaque marker band or a sensor/emitter usable with an electromagnetic or other type of navigation or image guidance system. Balloon 606 may be made of suitable biocompatible materials including, but not limited to PET, Nylon, PVC, polyurethane, silicone, etc. Balloon 606 can be inflated by a hollow balloon inflation tube 608. Balloon inflation tube 608 is attached to guide shaft 602 and is substantially collinear to guide shaft 602. The proximal end of balloon inflation tube 608 is in fluid connection to a balloon inflation port 610. The proximal end of guide shaft 602 may comprise a suitable hub such as a female luer lack 612. Guide catheter 600 can be used for introducing one or more devices or fluids through lumen 603. Lumen 603 can also be used for suctioning fluids. Balloon 606 may be used for dilating anatomical regions including, but not limited to anatomical passageways, ostia of paranasal sinuses, etc. FIG. 6B shows a cross sectional view through the plane 6B-6B of FIG. 6A. FIG. 6B shows balloon inflation tube 608 is attached to guide shaft 602.

FIG. 6C shows a guide catheter 620 that has an elongate body 622 comprising a lumen and a side channel, such as a side tube 626. Elongate body 622 may be made of suitable biocompatible materials including, but not limited to metals e.g. stainless steel, etc. or polymers e.g. Pebax, PEEK, etc. The distal end of elongate body 622 may comprise a curved, angled or bent region. The distal end of elongate body 622 may comprise a malleable region or may be actively deflectable by a user. The proximal end of elongate body 622 comprises a hub 624. In one embodiment, hub 624 is a female luer lock. The side lumen 626 may be aligned substantially parallel to the lumen of elongate body 622 and may extend distally to be flush with the distal end of the elongate body 622 or, in some cases, may terminate proximal to the distal end of the elongate body. In the particular example shown in the drawings, side lumen 626 extends from a proximal region of guide catheter 620 to a location that is substantially flush with the distal end of the elongate body 622. Side lumen 626 may be permanently or detachably attached to elongate body 622. A suitable endoscope 628 or other imaging device or imaging probe can be introduced through elongate side lumen 626 such that the distal end of endoscope 628 emerges out of the distal end of elongate side lumen 626. Examples of suitable endoscopes 628 that can be used with guide catheter 620 include Karl Storz Flexible Rhino-Laryngoscope (11101RP), made by Karl Storz Endoscopy—America, Culver City, Calif. The proximal end of endoscope 628 is connected to a video camera 630 to enable a user to view the anatomy around the distal region of guide catheter 620. This combination of guide catheter 620 and endoscope 628 is introduced in a target anatomy. Thereafter, one or more diagnostic, therapeutic or access devices are introduced through the lumen of elongate body 622 under endoscopic guidance. The curved, angled or bent region in the distal end of elongate body 622 is especially useful to navigate endoscope 628 around a tight bend in the anatomy.

FIG. 6D shows a guide catheter 650 having an elongate body 652, a lumen that extends through the elongate body and one or more attachment apparatus such as side clip(s) 656. Elongate body 652 may be made of suitable biocompatible materials including, but not limited to metals e.g. stainless steel, etc. or polymers e.g. Pebax, PEEK, etc. The distal end of elongate body 652 may comprise a curved, angled or bent region. The proximal end of elongate body 652 may comprise a hub 654. In one embodiment, hub 654 is a female luer lock. Side clips 656 may be permanently or removably attached to the outer surface of elongate body 652 as shown in FIG. 6C. The one or more side clips 656 may form a channel through which an endoscope may be introduced or may otherwise hold an endoscope in a position beside the elongate body 652 such that the endoscope may view a field ahead of or adjacent to the distal end of the device 650. Thus, one or more diagnostic, therapeutic or access devices may be introduced through the lumen of elongate body 652 under endoscopic guidance using an endoscope (or other imaging device or probe) that has been inserted or so other wise positioned within or supported by side clips 656. In one embodiment, side clips 656 may be cylindrical. In another embodiment, side clips 656 may be ring shaped.

FIG. 6E shows an endoscope 660 or other imaging device or imaging probe is combined with a guide catheter 662. Guide catheter 662 has a lumen. Guide catheter 662 may comprise a bent, angled or curved distal tip 664. In this particular example a magnet 666 causes the endoscope 660 to be attached by magnetic force to the guide catheter 662, as shown in FIG. 6D. This combination of endoscope 660 and guide catheter 662 is then introduced in the anatomy. Thereafter, one or more diagnostic, therapeutic or access devices may be introduced through the lumen of guide catheter 662 under endoscopic guidance or other image guidance using an endoscope 660 or other imaging device or imaging probe attached by magnetic force to the guide catheter 662.

FIG. 6F shows an endoscope 670-guide catheter 672 combination device or system. In this example, the guide catheter 672 has a lumen. Guide catheter 672 may comprise a bent, angled or curved distal tip 674. In this embodiment, endoscope 670 is combined with guide catheter 672 by an attachment apparatus that comprises a collar, such as a rubber collar 676. Rubber collar 676 comprises two parallel lumens. Endoscope 670 fits in the first lumen of rubber collar 676. Rubber collar 676 may be made of suitable biocompatible rubber materials including, but not limited to silicone, Pebax, PVC, etc. Similarly, guide catheter 672 fits in the second lumen of rubber collar 676. Thus, endoscope 670 is combined with guide catheter 672 to enable simultaneous introduction of endoscope 670 and guide catheter 672 into a target anatomy. Thereafter, one or more diagnostic, therapeutic or access devices are introduced through the lumen of guide catheter 672 under endoscopic guidance.

FIG. 6G shows an endoscope 680-guide catheter 682 combination device or system. Guide catheter 682 has a lumen and may comprise a bent, angled or curved distal tip 684. In this embodiment, endoscope 680 is combined with guide catheter 682 by a removable band 686 that ties endoscope 680 with guide catheter 682. In one embodiment, removable band 686 comprises a hook and loop type of attaching mechanism such as Velcro. Removable band 686 may be made of suitable biocompatible materials including, but not limited to silicone, Pebax, nylon, stainless steel, Nickel-titanium alloy (e.g., Nitinol)™ etc. Thus, endoscope 680 is combined with guide catheter 682 to enable simultaneous introduction of endoscope 680 and guide catheter 682 into a target anatomy. Thereafter, one or more diagnostic, therapeutic or access devices are introduced through the lumen of guide catheter 682 under endoscopic guidance.

FIGS. 6H and 6I show another endoscope-guide catheter combination device or system 698. As seen in FIG. 6H, the guide catheter comprises an elongate shaft 690. In some cases, a distal region of elongate shaft 690 may further comprise a curved, bent or angled region 692. The guide catheter further comprises a hub 694 located on the proximal end of elongate shaft 690. In one embodiment, hub 694 is a female luer lock. The guide catheter is attached to an endoscope 696 such as a fiber-optic endoscope by an adjustable connector 698 comprising a hollow body 699. Hollow body 699 comprises two channels: a first channel comprising a first proximal orifice 6000 and a first distal orifice 6002 and a second channel comprising a second proximal orifice 6004 and a second distal orifice 6006, The first channel allows the guide catheter to pass through adjustable connector 698. The second channel allows endoscope 696 to pass through adjustable connector 698. Adjustable connector comprises a first gripping mechanism 6008 and a second gripping mechanism 6010. First gripping mechanism 6008 enables adjustable connector 698 to grip the guide catheter. Similarly, second gripping mechanism 6010 enables adjustable connector 698 to grip endoscope 696. In the embodiment shown in FIG. 6H, first gripping mechanism 6008 comprises an elongate lever 6012 pivoted on a pivot 6014 located on adjustable connector 698. One end of elongate lever 6012 is attached by a spring mechanism 6016 to adjustable connector 698. Spring mechanism 6016 causes the distal end of elongate lever 6012 to press on the guide catheter. This in turn causes the guide catheter to press on an edge of first proximal orifice 6000 and first distal orifice 6002. This in turn causes adjustable connector 698 to grip the guide catheter. Similarly, second gripping mechanism 6010 comprises an elongate lever 6018 pivoted on a pivot 6020 and a spring mechanism 6022 to cause adjustable connector 698 to grip endoscope 696. To adjust the relative positions of the guide catheter and/or the endoscope 696, a user presses the proximal regions of elongate lever 6012 and/or elongate lever 6018 as shown in FIG. 6I. Pressing the proximal region of elongate lever 6012 causes the distal region of elongate lever 6012 to move away from the guide catheter. This in turn releases the guide catheter from adjustable connector 698. Similarly, pressing the proximal region of elongate lever 6018 releases endoscope 696 from adjustable connector 698. Thus, adjustable connector 698 can be used to maintain the relative position of the guide catheter and endoscope 696 during introduction or removal of the guide catheter in the anatomy and/or while performing a diagnostic, therapeutic or access procedure. If needed, the relative position of the guide catheter and endoscope 696 can be adjusted before during or after a procedure. Various regions of adjustable connector may be made of suitable biocompatible materials including, but not limited to metals e.g. stainless steel, Nickel-titanium alloy (e.g., Nitinol), titanium, etc.; suitable polymers, etc. Similarly, other embodiments of adjustable connectors can be used to maintain the relative position of the guide catheter and endoscope 696 during introduction or removal of the guide catheter in the anatomy and/or while performing a diagnostic, therapeutic or access procedure.

FIG. 6J shows a perspective view of an embodiment of a removable attachment apparatus comprising a clipping device 6030 useable to introduce or support an endoscope, image apparatus or various other devices along side a guide catheter 6020. In the example shown, guide catheter 6020 comprises an elongate hypotube 6022 enclosing an elongate tubular member 6024. Elongate tubular member 6024 encloses a lumen to allow for insertion of one or more devices through guide catheter 6020. The distal end of tubular member 6024 may be angled, bent or curved. The distal end of tubular member 6024 may comprise an atraumatic tip 6026. The proximal end of tubular member 6024 comprises a hub. In one embodiment, the hub is a female luer lock. A removable clipping device 6030 can clip on to guide catheter 6020. Clipping device 6030 can be made of suitable biocompatible materials such as metals, rubbers, polymers, etc. Clipping device 6030 comprises a first clip 6032 and a second clip 6034. First clip 6032 is adapted to attach to the outer surface of guide catheter 6020. Second clip 6034 is adapted to attach to the outer surface of an endoscope. Such a combination of an endoscope and a device such as a guide catheter can be introduced by a physician using a single hand.

FIGS. 6K and 6L show the steps of a method of accessing an anatomical region using the removable clipping device shown in FIG. 6J. In FIG. 6K, clipping device 6030 is attached to guide catheter 6020. Thereafter, guide catheter 6020 is introduced in an anatomical region such as the nasal cavity. An endoscope 6036 is introduced in the anatomy along with guide catheter 6020. Endoscope 6036 helps to visualize the anatomy to facilitate the introduction and/or the navigation of guide catheter 6020 in the anatomy. If desired, endoscope 6036 may be attached to guide catheter 6020 using clipping device 6030 as shown in FIG. 6L. This enables the relative position of endoscope 6036 and guide catheter 6020 to be relatively fixed during a procedure. Endoscope 6036 and guide catheter 6020 can thus be co-introduced in an anatomical region. In one embodiment, clipping device 6030 is made of a flexible material such as a suitable rubber to allow for angular displacement of the axis of endoscope 6036 relative to the axis of guide catheter 6020. In another embodiment, the contact surface between clipping device 6030 and one or both of endoscope 6036 and guide catheter 6020 is smooth. This allows endoscope 6036 to slide relative to guide catheter 6020. In another embodiment, endoscope 6036 and/or guide catheter 6020 can be rotated around their axes even when attached to clipping device 6030. In another embodiment, clipping device 6030 allows minimal motion of endoscope 6036 relative to guide catheter 6020.

FIGS. 6M through 6O shows various steps of a method of introducing one or more diagnostic or therapeutic devices along or beside another device such as an endoscope or other imaging device or imaging probe. In the example of FIG. 6M, the introducing device 6040 comprises an endoscope 6042 and an attachment or receiving apparatus comprising a side lumen 6044. Introducing device 6040 is introduced in a desired region of the anatomy. This introduction may be performed using endoscope 6042, using a separate endoscope or using fluoroscopy or other imaging/guidance techniques. Thereafter, a guidewire 6046 is introduced through side lumen 6044. Guidewire 6046 is navigated through the anatomy under endoscopic visualization by endoscope 6042. Thereafter, guidewire 6046 is placed in a desired target region. In one method embodiment, guidewire 6046 is placed across an ostium of a paranasal sinus. Thereafter, in FIG. 6N, a working device such as a balloon catheter 6048 comprising a dilating balloon 6050 is introduced over guidewire 6046 into the target anatomy. Thereafter, in FIG. 6O, balloon 6050 is inflated to dilate a region of the target anatomy. In one method embodiment, balloon 6050 is inflated to dilate an ostium of a paranasal sinus. Thereafter, balloon 6050 is deflated and balloon catheter 6048 and introducing device 6040 are removed form the anatomy. Similarly, other diagnostic or therapeutic devices may be introduced through side lumen 6044 to perform one or more diagnostic or therapeutic procedures.

FIG. 6P shows an embodiment of a method of introducing a dilator through the introducing device of FIG. 6M. In this embodiment, dilator 6052 comprises a flexible shaft and a rounded distal end to dilate or displace tissue.

FIG. 6Q shows a deflectable introducing device 6054 that generally comprises an endoscope and an introducing lumen. Introducing device 6054 comprises a proximal handle 6056. Proximal handle 6056 encloses an elongate tubular element 6058. In one embodiment, the proximal region of tubular element 6058 is substantially rigid. In another embodiment, the distal region of tubular element 6058 comprises a bent region. In another embodiment, the distal region of tubular element 6058 is malleable or plastically deformable. In FIG. 6Q, the distal region of tubular element 6058 is removed to show structures enclosed by the distal region of tubular element 6058. Tubular element 6058 encloses an endoscope 6060 and an introducing lumen 6062. Endoscope 6060 is used to visualize the anatomy or one or more diagnostic or therapeutic devices while performing a diagnostic or therapeutic procedure. The proximal end of introducing lumen 6062 may comprise a suitable hub 6064. In one embodiment, hub 6064 is a female luer hub. Introducing lumen 6062 can be used to introduce one or more diagnostic, therapeutic or access devices into the anatomy. In one embodiment, introducing device 6054 comprises a steering or deflecting mechanism to allow a user to controllably bend or deflect the distal region of tubular element 6058. In the embodiment shown in FIG. 6Q, introducing device 6054 comprises a sliding button 6066 that is attached to a pull wire. The pull wire in turn is attached to one or more distal rings 6068 located on the distal region of tubular element 6058. A user can move sliding button 6066 to cause a distal region of tubular element 6058 to controllably bend or deflect. In another embodiment of a steering or deflecting mechanism, the distal region of endoscope 6060 is attached to a distal region of tubular element 6058. The distal region of endoscope 6060 may be attached to a distal region of tubular element 6058 by one or more distal rings 6068. In this embodiment, pulling endoscope 6060 causes a distal region of tubular element 6058 to controllably bend or deflect. FIG. 6R shows a perspective view of the distal region of the introducing device of FIG. 6Q in a bent or deflected state. A distal region of tubular element 6058 has been removed to show structures enclosed by the distal region of tubular element 6058. Introducing device 6054 may be used to introduce one or more diagnostic, therapeutic or access devices into the anatomy. In one embodiment, introducing device 6054 is used to introduce a balloon catheter. In another embodiment, introducing device 6054 is used to introduce a guidewire into the anatomy. The guidewire is thereafter used to introduce one or more diagnostic, therapeutic or access devices into the anatomy.

FIGS. 7A through 7C show various steps of a method of accessing an anatomical opening using an introducing device 700 that generally comprises an endoscope 702 and an introducing lumen 704. The introducing device 700 may be inserted into the body through an orifice or opening such as a nostril. Thereafter, introducing device 700 is positioned, possibly under endoscopic visualization or other image guidance, such that the distal end of introducing device 700 is positioned near a target of interest such as an opening of a paranasal sinus. Thereafter, in FIG. 6S, a diagnostic, therapeutic or access device is inserted through introducing lumen 704 into the target of interest. In the example shown in FIG. 7B, the target of interest is an opening of a paranasal sinus and a guidewire 706 is being inserted through introducing lumen 704 into a retro-bullar ostium or recess. Guidewire 706 may then be used to introduce one or more diagnostic, therapeutic or access into the retro-bullar ostium or recess, as shown. FIG. 7C shows a perspective view of a region of the human face showing the manner in which the introducing device 700 may be transnasally inserted in the method shown in FIGS. 7A and 7B. After the introducing device 700 has been inserted and positioned, various guidewires or other diagnostic, therapeutic or access devices may be inserted through introducing lumen 704.

Figure 8A:
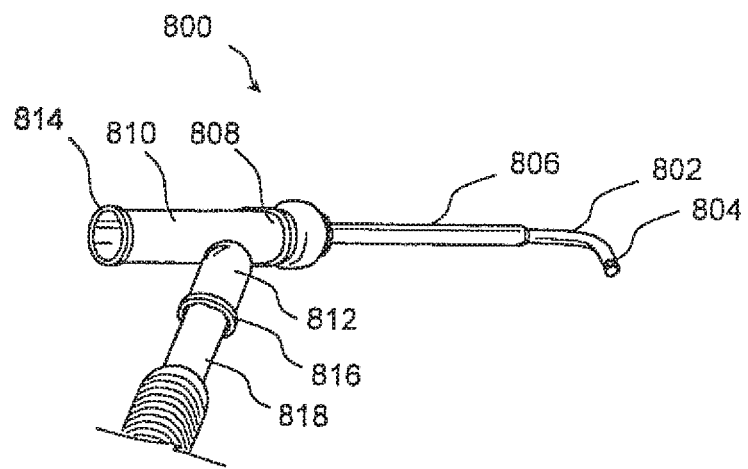
FIG. 8A shows a perspective view of a tubular guide equipped for optional suctioning.

Any of the guide catheters or other luminal devices disclosed herein may comprise an arrangement for suctioning an anatomical region through the distal end of the guide catheter or device unless to do so would render the device unusable for its intended purpose. For example, FIG. 8A shows a guide catheter 800 comprising an elongate tube 802 that may be made of suitable biocompatible materials including, but not limited to metals such as stainless steel, titanium, Nickel-titanium alloy (e.g., Nitinol), etc.; plastics such as Pebax, PEEK, Nylon, polyethylene, etc. The distal region of elongate tube 802 may comprise a curved, bent or angled region. In some embodiments, the distal end of elongate tube 802 may comprise an atraumatic tip 804. Although various modes of construction may be used, in the example shown, an elongate hypotube 806 is disposed on the outer surface of elongate tube 802 and the proximal end of guide catheter 800 comprises a branched or Y-connector 808. The proximal region of Y-connector 808 comprises a straight arm 810 and a side arm 812. The proximal end of straight arm 810 comprises suitable hub 814. In one embodiment, hub 814 is a female luer hub. In another embodiment, hub 814 comprises a rotating hemostasis valve such as a Touhy-Borst adapter. The proximal end of side arm 812 comprises a suitable hub 816. In one embodiment, hub 816 comprises a rotating hemostasis valve such as a Touhy-Borst adapter to adjust the amount of suction. Hub 816 is connected to a suction tube 818 that provides suction to guide catheter 800. Thus, guide catheter 800 can be used to provide suction as well as introduce one or more diagnostic, therapeutic or access devices into the anatomy.

Figure 8B:
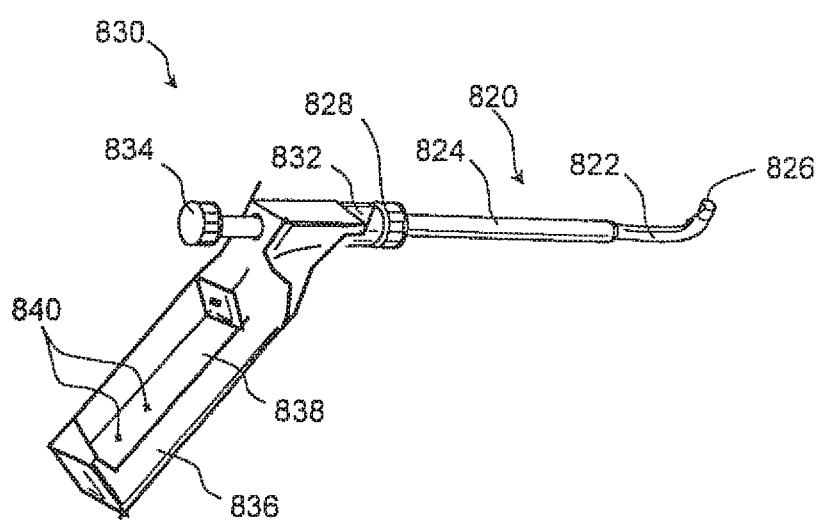
FIG. 8B shows a perspective view of a guide having a handpiece that is configured to receive a detachable navigational modality to facilitate use of the device in an image guided surgical or interventional procedure.

Various devices being introduced in the anatomy may comprise a detachable navigation apparatus (e.g., a navigation module or localizer) useable in conjunction with a navigation or image guidance system to track and/or navigate the devices through the anatomy. For example, FIG. 8B shows a perspective view of a guide catheter 820 having a navigation adapter 830 that is designed to receive detachable navigation apparatus such as a navigation module or localizer containing sensor(s), emitter(s), transmitter(s), reflector(s), etc. that are useable in conjunction with a navigation system. The navigation apparatus may be selected from the various navigation apparatus disclosed herein or in one of the patent applications incorporated herein by reference. In the embodiment shown in FIG. 8B, guide catheter 820 comprises an elongate body 822 having a lumen. Elongate body 822 may be made of suitable biocompatible materials including, but not limited to metals e.g. stainless steel, titanium, Nickel-titanium alloy (e.g., Nitinol), etc.; polymers e.g. Pebax, PEEK, Nylon, polyethylene, etc. The distal end of elongate body 822 may comprise a bent, curved or angled region. The proximal region of elongate body 822 may comprise a hypotube 824 located on the external surface of elongate body 822. The distal end of elongate body 822 may comprise an atraumatic tip 826. The proximal end of guide catheter 820 comprises a first attachment mechanism 828. In one embodiment, first attachment mechanism 828 is a female luer lock. First attachment mechanism 828 is used to attach guide catheter 820 to a navigational adaptor 830. Navigational adaptor 830 comprises a second attachment mechanism 832 that attached to first attachment mechanism 828 on the proximal end of guide catheter 820. In one embodiment, second attachment mechanism 832 is a male luer lock. Navigational adaptor 830 further comprises a proximal hub 834 that is in fluid communication with second attachment mechanism 832. Navigational adaptor 830 further comprises a handle 836 to enable a user to hold and navigate guide catheter 820. The outer surface of handle 836 may be roughened to increase the grip of a user on handle 836. In one embodiment, outer surface of handle 836 is roughened by knurling. Handle 836 comprises a bay to attach a suitable navigational localizer 838 to navigational adaptor 830. Examples of navigational localizer 838 are encoded passive manipulator, active manipulator, ultrasound localizer, electromagnetic localizer, active optical localizer, passive optical localizer, etc. Navigation adaptor 830 may further comprise an identification module 840. Identification module 840 enables navigational localizer 838 to identify the type of navigational adaptor 830 that is being connected to navigational localizer 838. This enables the registration of the location and orientation of the distal tip of navigational adaptor 830 by navigational localizer 838. In the embodiment shown in FIG. 8B, identification module 840 comprises a pair of magnets. The unique magnetic field generated by the pair of magnets is measured by navigational localizer 838. This enables navigational localizer 838 to identify the type of navigational adaptor 830 being attached to navigational localizer 838. Other examples of identification module 840 include, but are not limited to electrical modules e.g. a ROM that provides electrical information to navigational localizer 838; mechanical modules e.g. connector-pin arrangements that provide mechanical information to navigational localizer 838; other magnetic modules that provides magnetic information to navigational localizer 838; etc. In a particular embodiment, the distal end of elongate body 822 comprises a malleable or shapeable region. In this embodiment, the position and orientation of the distal tip of guide catheter 820 is re-calibrated to navigational localizer 838 after performing a step of bending or shaping the distal end of elongate body 822.

In an alternate embodiment of navigational adaptor 830 of FIG. 8B, handle 836 may comprise a non-detachable navigational localizer 838.

Figure 9:
FIG. 9 shows a perspective view of a tubular guide having a tapered connector on its proximal end to facilitate attachment of a suction tube to the tubular guide.

The devices disclosed herein, especially the guide catheters, may comprise a proximal region adapted to fit to a suction tube. For example, FIG. 9 shows a perspective view of a tubular guide having a tapered connector on its proximal end to facilitate attachment of a suction tube to the tubular guide. FIG. 9 shows a tubular guide 900 comprising an elongate shaft 902. The proximal end of elongate shaft 902 may comprise a suitable hub 904 to attach one or more devices to the proximal end of guide catheter 900. In one embodiment, hub 904 is a female luer lock. Tubular guide 900 further comprises a tapered region 906 on the proximal region of elongate shaft 902. Tapered region 906 comprises a wider proximal region and a narrower distal region to allow a suction tube to be fitted on the proximal end of tubular guide 900. One or more grooves or ridges of the external surface of tapered region 906 may be provided to increase the grip of the suction tube on tapered region 906. Tapered region 906 may also be used to attach a tube on the proximal end of tubular guide 900 to deliver a suitable flushing fluid. The distal region of tubular guide 900 may comprise a bent, curved or angled distal region 908.

Figure 10:
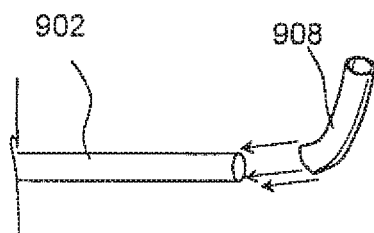
FIG. 10A is an exploded view showing the components of a tubular guide device formed of a straight proximal segment and a curved distal segment.
FIG. 10B is an assembled view of the device shown in FIG. 10A.
FIG. 10C shows a distal portion of a tubular guide comprising a polymeric inner tube and an outer tube having apertures, wherein the polymeric material of the inner tube is caused to flow or protrude through the apertures thereby holding the inner tube in substantially fixed position within the outer tube.
Figure 10:
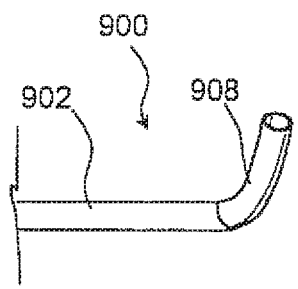
Figure 10:
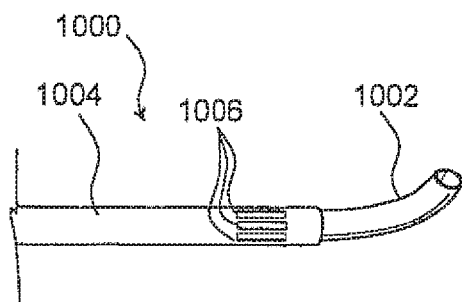

Bent, curved or angled regions of one or more devices disclosed herein may be made by bending a portion of the device and, in some instances, the devices will me formed of malleable material or may incorporate a malleable region to permit the user to bend, curve, angle or otherwise configure the device as desired. Some of the devices disclosed herein may be made by joining two elements, one of which comprises a bent, curved or angled region. For example, FIG. 10A is an exploded view showing the components of a tubular guide device of FIG. 9 formed of a straight proximal segment 902 and a curved distal segment 908. In this example, the bent, curved or angled distal segment 908 is attached to the proximal segment 902 as shown in the assembled view of FIG. 10B. The distal end of proximal region 902 may be joined to the proximal end of distal region 908 at any desired angle. This may be done, for example, by cutting the distal end of proximal segment 902 at and angle and/or cutting the proximal end of distal segment 908 at an angle and then joining the segments in an end-to-end butt joint fashion. Optionally, a sleeve or covering may surround the joint between the proximal end of the distal segment 902 and the distal end of the proximal segment 908. Embodiments where the distal segment 908 is joined to the proximal segment 902 at an angle may be used to make one or more of the devices disclosed herein that comprise a bent, curved or angled region.

In an alternate method of manufacture, bent, curved or angled regions of one or more devices disclosed herein are made by joining two molded parts. The two molded parts are made such that each molded part comprises a bent, curved or angled region. The two molded parts are then joined to each other to produce a tubular element enclosing a lumen.

FIG. 10C shows a tubular guide or guide catheter 1000 that comprises a first tube 1004 and a second tube 1002 that is formed of polymeric or other material that melts or softens so as to be flowable through openings 1006 formed in the first tube 1004. The second tube 1002 protrudes out of and beyond the distal end of the fist tube 1004. Second tube 1002 may be made of suitable biocompatible materials including, but not limited to Pebax, PEEK, Nylon, polyethylene, etc. The first tube 1004 may also be formed of any suitable material such as hypotube made of a biocompatible metals including, but not limited to stainless steel, Nickel-titanium alloy (e.g., Nitinol), etc. During manufacture, the second tube 1002 is positioned such that a proximal portion of the second tube 1002 extends into of through the lumen of the first tube 1004 and the second tube 1002 is caused to melt or soften (e.g., by heating) in the area of the openings 1006. The melted or softened material of second tube 1002 thereafter enters the one or more openings (e.g., holes or notches) 1006 of first tube 1004 and is allowed to resolidify, thereby forming a bond or lock between the first tube 1004 and the second tube 1002. Such a method of manufacture may be used for manufacturing one or more devices comprising hypotubes disclosed herein or in the patent applications incorporated herein by reference.

FIG. 11 shows a perspective view of an embodiment of a guide catheter comprising a curved, bent or angled distal flap. Guide catheter 1100 comprises an elongate body 1102 comprising a lumen. Elongate body 1102 may be made from suitable biocompatible materials including, but not limited to metals such as stainless steel or Nickel-titanium alloy (e.g., Nitinol), or polymers such as Nylon, Pebax, PEEK, polyethylene, etc. The lumen of elongate body 1102 may be used to introduce one or more elongate devices through guide catheter 1100. The distal region of elongate body 1102 comprises a curved, bent or angled distal flap 1104. Flap 1104 is oriented at an angle to the axis of guide catheter 1100 as shown in FIG. 11. In one embodiment, flap 1104 is created by removing material from the distal end of elongate body 1102 and bending the distal end of elongate body 1102. In another embodiment, flap 1104 is created by attaching an element comprising flap 1104 to the distal region of elongate body 1102. Such guide catheters may be used for introducing one or more elongate devices such as a guidewire 1106 at a desired angle to the guide catheter.

Similar flap regions may also be attached to the distal end of endoscopes comprising one or more endoscope lumens. This enables a user to introduce one or more devices through the one or more endoscope lumens at an angle to the axis of the distal region of the endoscope.

FIG. 12 shows a perspective view of a guide catheter comprising an elongate body 1202, lumens 1206, 1210 terminating in openings 1208, 1212 and an optional atraumatic distal tip 1204. Atraumatic distal tip 1204 prevents or reduces damage to the anatomy while introducing guide catheter 1200 into the anatomy. Elongate body 6172 may be made from suitable biocompatible materials including, but not limited to Nylon, Pebax, PEEK, polyethylene, etc. Guide catheter 1200 further comprises a lumen 1206 that extends from the proximal region of guide catheter 1200. The distal end of lumen 1206 emerges out of the distal region of guide catheter 1200 through a lumen opening 1208. The distal end of lumen 1206 comprises a bent, curved or angled region such that an elongate device introduced through lumen 1206 emerges out of lumen opening 1208 at an angle to the axis of guide catheter 1200. Guide catheter 1200 may comprise one or more lumens. In the example shown in FIG. 12, guide catheter 1200 further comprises a second lumen 1210 that extends from the proximal region of guide catheter 1200. The distal end of second lumen 1210 emerges out of the distal region of guide catheter 1200 through a second lumen opening 1212. FIG. 12A shows a cross section through the guide catheter shown in FIG. 12 through the plane 12A-12A. Guide catheter 1200 comprises an elongate body 1202 comprising lumen 1206 and second lumen 1210. Such guide catheters may be used for introducing one or more elongate devices such as guidewires at a desired angle to the guide catheter. Such guide catheters may also comprise an endoscope lumen. In one embodiment, the endoscope lumen has a side opening to enable a user to introduce one or more elongate devices such as guidewires under endoscopic guidance.

Figure 13:
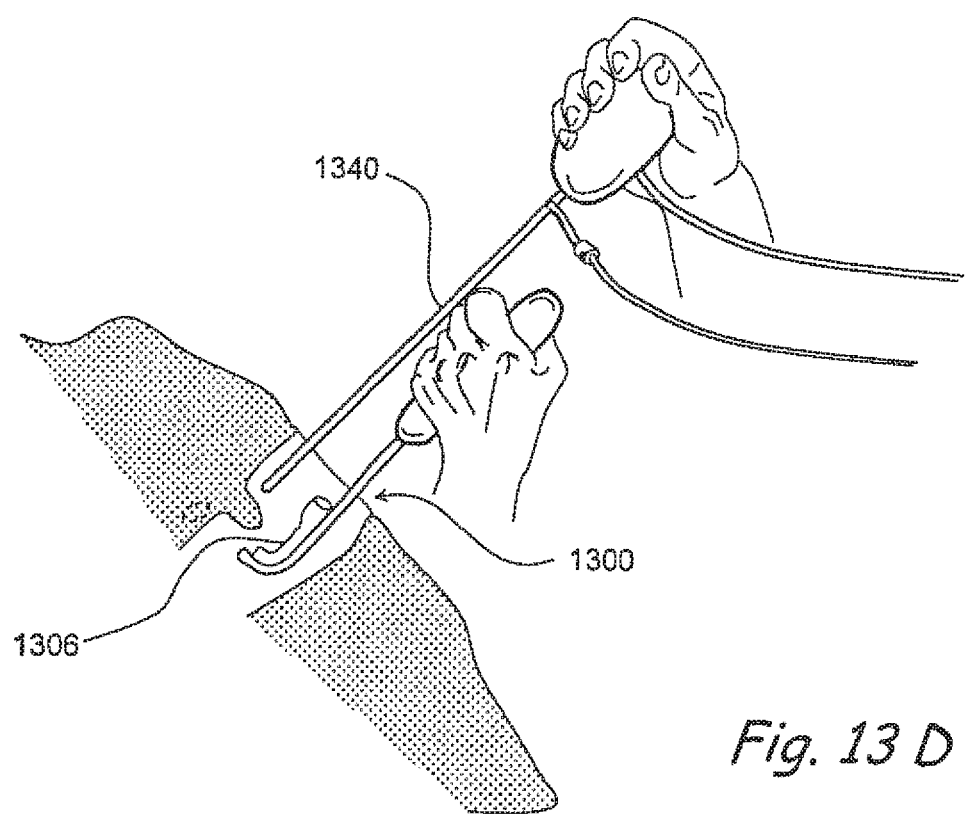
FIG. 13A shows a distal portion of a tubular guide having a curved endoscopic apparatus attached thereto.
FIG. 13B is a longitudinal sectional view of an endoscopic apparatus in the nature of a periscope.
FIG. 13C is a longitudinal sectional view of an endoscopic apparatus in the nature of a curved wave guide.
FIGS. 13D-E show steps in a method wherein the device of FIG. 13A is used in combination with a straight endoscope to accomplish position of the distal tip of the tubular guide at an obscured anatomical location within the body of a human or animal subject.
Figure 13:
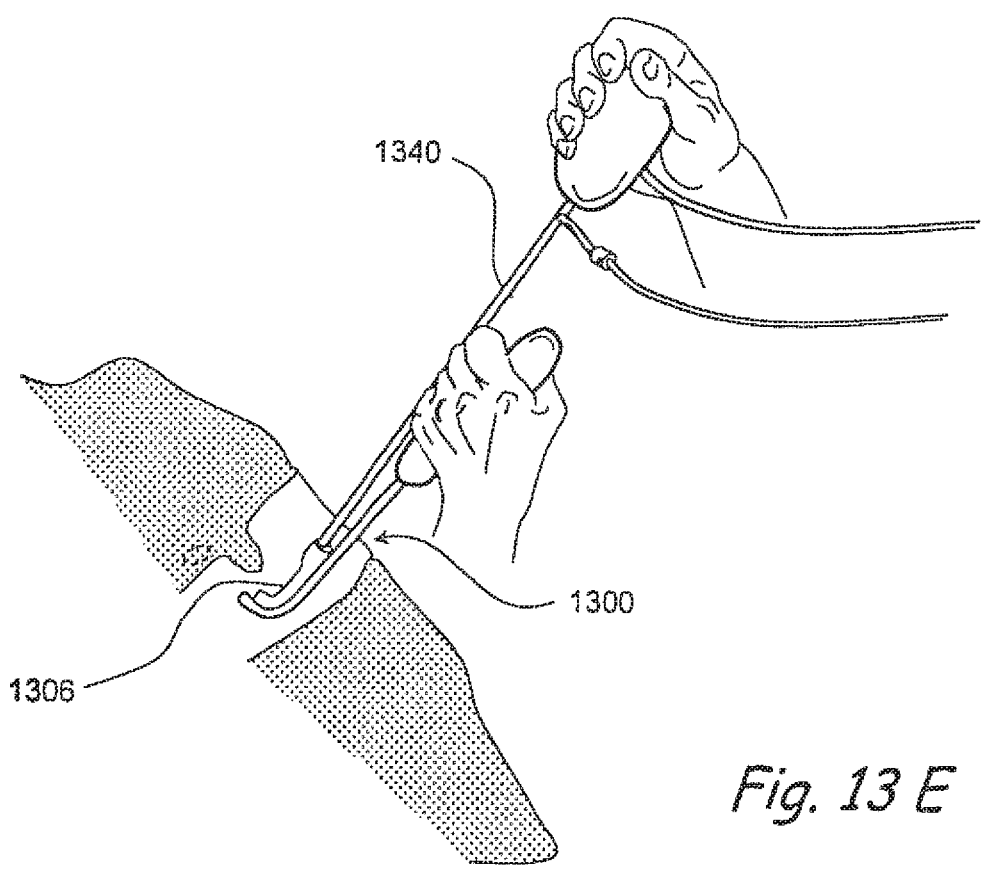

FIG. 13A shows a tubular guide or guide catheter 1300 comprises an elongate tubular body 1302 that may be substantially rigid and an endoscopic apparatus 1306 attached to the body 1302 and useable to facilitate endoscopic viewing of a field ahead or adjacent to the distal end of the tubular guide body 1302. Elongate body 1302 may be made of suitable biocompatible materials including, but not limited to metals such as stainless steel, titanium, Nickel-titanium alloy (e.g., Nitinol), etc.; plastics such as Nylon, Pebax, PEEK, polyethylene, etc. The distal region of elongate body 1302 comprises a curved, bent or angled region to enable the user to introduce one or more devices into the target region around the anatomical obstruction. The curved, bent or angled region of elongate body 1302 may be bent by an angle ranging from 25 degrees to 130 degrees. The distal end of elongate guide 1302 may comprise an atraumatic tip 1304 to reduce or eliminate trauma to surrounding tissues while using device guide 1300. In this example, the endoscopic apparatus 1306 comprises a periscope or waveguide that is attached to the side of the tubular body 1302. The proximal end of this periscope 1306 comprises a socket

1308. Socket 1308 enables the distal end of an endoscope to attach to periscope 1306. Distal end of periscope 1306 comprises a curved, bent or angled region to enable the user to visualize the target region around the anatomical obstruction. The curved, bent or angled region of periscope 1306 may be bent by an angle ranging from 25 degrees to 130 degrees. In one embodiment of a method of using device guide 1300, the target region around the anatomical obstruction is visualized by an endoscope attached to periscope 1306. Thereafter, one or more diagnostic, therapeutic or introducing devices are introduced into the target region through elongate body 1302. FIG. 13B shows a longitudinal sectional view of the device guide shown in FIG. 13A. FIG. 13B shows device guide 1300 comprising an elongate body 1302 with an atraumatic tip 1304. The proximal end of periscope 1306 comprises a socket 1308. Socket 1308 comprises a gasket 1312 to substantially seal the interface between an endoscope and socket 1308. The distal end of periscope 1306 comprises lens 1310. Light entering lens 1310 is reflected by a mirror 1314 and is directed towards socket 1308. Thereafter, the light enters the endoscope to provide the user an image of the target anatomy to be visualized. In one alternate embodiment, the mirror may be polarized to improve image quality and reduce glare.

FIG. 13C shows a longitudinal sectional view of a second embodiment of a device guide comprising a periscope to enable a user to endoscopically visualize a target region around an anatomical obstruction. Device guide 1320 comprises an elongate body 1322 comprising a lumen. Elongate body 1322 may be made of suitable biocompatible materials including, but not limited to metals such as stainless steel, titanium, Nickel-titanium alloy (e.g., Nitinol), etc.; plastics such as Nylon. Pebax, PEEK, polyethylene, etc. The distal region of elongate body 1322 comprises a curved, bent or angled region to enable the user to introduce one or more devices into the target region around the anatomical obstruction. The curved, bent or angled region of elongate body 1322 may be bent by an angle ranging from 25 degrees to 130 degrees. The distal end of elongate guide 1322 may comprise an atraumatic tip 1324 to reduce or eliminate trauma to surrounding tissues while using device guide 1320. A periscope 1326 is attached lengthwise to elongate body 1320. Distal end of periscope 1326 comprises a curved, bent or angled region to enable the user to visualize the target region around the anatomical obstruction. The curved, bent or angled region of periscope 1326 may be bent by an angle ranging from 25 degrees to 130 degrees. The proximal end of periscope 1326 comprises a socket 1328. Socket 1328 enables the distal end of an endoscope to attach to periscope 1326. Socket 1328 comprises a gasket 1330 to substantially seal the interface between an endoscope and socket 1328. The distal end of periscope 1326 comprises a lens 1332. Periscope 1326 further comprises fiber optic fibers 1334 located proximal to lens 1332. Light passing through lens 1332 passes through fiber optic fibers 1334. Thus, light emitted by the endoscope is transmitted by fiber optic fibers 1334 through lens 1332 to illuminate a field of view. The light is reflected from anatomical regions and enters lend 1332. Light entering lens 1332 is transmitted by fiber optic fibers 1334 to socket 1328. Thereafter, the light enters the endoscope attached to socket 1328 to provide the user an image of the target anatomy to be visualized. Fiber optic fibers 1334 of periscope 1326 are arranged such that they are substantially aligned with the fiber optic fibers of the endoscope attached to socket 1328. In one embodiment, a part of fiber optic fibers 1334 of periscope 1326 are designed to transmit light emitted from the endoscope to illuminate the field of view. Another part of fiber optic fibers 1334 of periscope 1326 are designed to transmit light reflected from anatomical structures to the endoscope. In one embodiment, periscope 1326 further comprises one or more intermediate lenses 1336 located between the ends of adjacent bundles of fiber optic fibers 1334 as shown in FIG. 13C. In one embodiment of a method of using device guide 1320, the target region around the anatomical obstruction is visualized by an endoscope that is attached to periscope 1326. Thereafter, one or more diagnostic, therapeutic or introducing devices are introduced into the target region through elongate body 1322.

FIGS. 13D and 13E show the various steps of an embodiment of a method to endoscopically visualize a target region around an anatomical obstruction using a device guide comprising a periscope. In this method embodiment, device guide 1320 shown in FIG. 13A is used as an example of a device guide comprising a periscope. In FIG. 13D, a user attempts to visualize a target anatomical region around an anatomical obstruction using an endoscope 1340. In one embodiment, the target anatomical region is the ostium of a maxillary sinus and the anatomical obstruction is a nasal turbinate. If the attempt is unsuccessful, the method proceeds to the step shown in FIG. 13E. In FIG. 13E, the user fits the distal tip of endoscope 1340 into the proximal end of periscope 1306. This enables the user to visualize the anatomy around the anatomical obstruction. Thereafter, one or more devices may be introduced through device guide 1320 into the anatomy.

The various devices described or incorporated herein may include one or more optical marker(s). Such optical marker(s) may be used for example for optically determining the relative location of the balloon of the balloon catheter with respect to the distal end of a guide catheter through which the balloon catheter is introduced. Such optical marker(s) may enable a user to determine the location of the balloon of the balloon catheter with respect to the distal end of a guide catheter without using methods like fluoroscopy that used ionizing radiation. If the balloon is too close to the distal end of the guide catheter, there is a risk that the balloon may be inflated by a user while it is inside the guide catheter. If the balloon is too far from the distal end of the guide catheter, the guide catheter may not provide adequate support to the balloon catheter. Thus, the balloon of the balloon catheter should be located at an optimal distance with respect to the distal end of the guide catheter. In one embodiment, the optimal distance is ensured by providing an optical marker on the proximal region of the balloon catheter. The balloon catheter is inserted through a guide catheter such that the distal region of the balloon catheter emerges out of the distal end of the guide catheter. The location of the optical marker relative to the proximal region of the guide catheter is used to determine the relative location of the balloon of the balloon catheter with respect to the distal end of the guide catheter. In another embodiment, the optimal distance is ensured by providing an optical marker on the distal region of the balloon catheter. The balloon catheter is inserted through a guide catheter such that the distal region of the balloon catheter emerges out of the distal end of the guide catheter. The location of each optical marker may be tracked by an endoscope inserted in the anatomy. The location of the optical marker relative to the distal end of the guide catheter is used to determine the relative location of the balloon of the balloon catheter with respect to the distal end of the guide catheter.

Similar optical markers may be located on other balloon catheters disclosed herein. For example, an optical marker may be located on a balloon catheter proximal to a balloon on the balloon catheter. Such an optical marker is especially useful to determine the location of the balloon with respect to a paranasal sinus ostium after the balloon has been introduced in a paranasal sinus. After the balloon is inserted inside the paranasal sinus, the balloon can no longer be visually seen by an endoscope. The user can then note the location of the optical marker proximal to the balloon. This information enables the user to determine the length of the balloon that is present inside the opening. This information in turn can be used by the user to accurately position the balloon with respect to the paranasal sinus ostium to achieve optimal dilation of the paranasal sinus ostium.

The optical markers disclosed herein may be combined optical-radiopaque markers. In one embodiment, the combined optical-radiopaque marker comprises a platinum coil or marker. Preferably, the combined optical-radiopaque marker comprises a coating of a colored polymer including, but not limited to colored heat shrink polyethylene terephthalate. The length of the combined optical-radiopaque marker ranges preferably from 0.5 mm-10 mm.

While removing a balloon catheter from the anatomy, the balloon of the balloon catheter might accidentally pull anatomical structures like the uncinate and damage the anatomical structures. To prevent such damage, in the method embodiments where a balloon catheter is introduced through a guide device, the balloon catheter may be removed from the anatomy along with the guide device. This step may be performed after ensuring that an undesirably long distal region of the balloon catheter is not protruding from the distal end of the guide device. The guide device may have a suitable attachment mechanism such as a rotating hemostasis valve, a clip, etc. to temporarily attach the balloon catheter to the guide device. The attachment mechanism enables a user to remove the balloon catheter from the anatomy along with the guide device.

The flexible endoscopes disclosed herein may comprise one or more endoscope lumens. In one embodiment, the endoscope lumen is a side lumen. The side lumen is designed such that one or more diagnostic, therapeutic or access devices can be inserted in the anatomy through the side lumen under endoscopic guidance.

Figure 14:
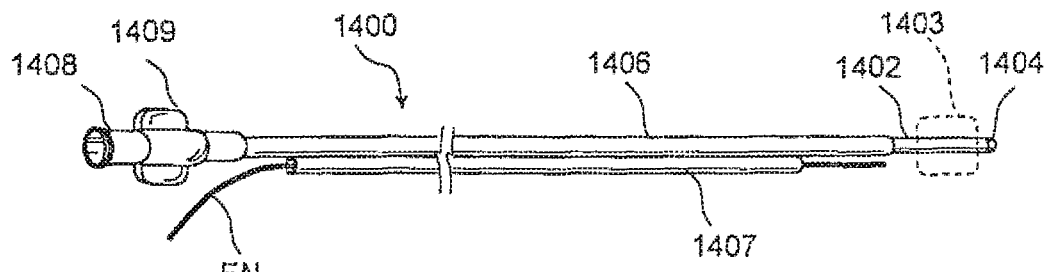
FIG. 14A is a perspective view of a straight tubular guide of the present invention having an endoscopic device attached thereto or integrated therewith and an optional balloon.
FIG. 14B is a perspective view of a curved tubular guide of the present invention having an endoscopic device attached thereto or integrated therewith and an optional balloon.
FIG. 14C is a perspective view of another curved tubular guide of the present invention having an endoscopic device attached thereto or integrated therewith and an optional balloon.
FIG. 14D is a perspective view of another curved tubular guide of the present invention having an endoscopic device attached thereto or integrated therewith and an optional balloon.
FIG. 14E is a perspective view of another curved tubular guide of the present invention having an endoscopic device attached thereto or integrated therewith and an optional balloon.
Figure 14:
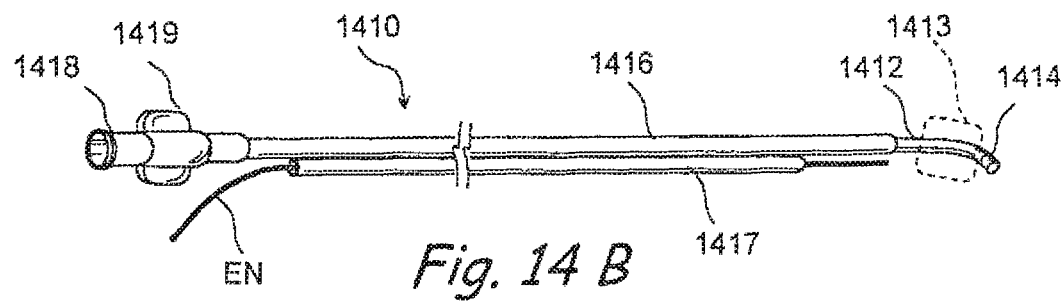
Figure 14:
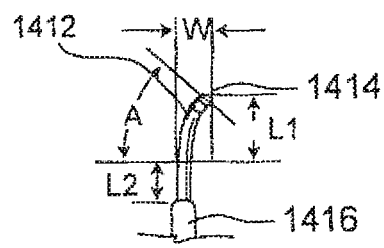
Figure 14:
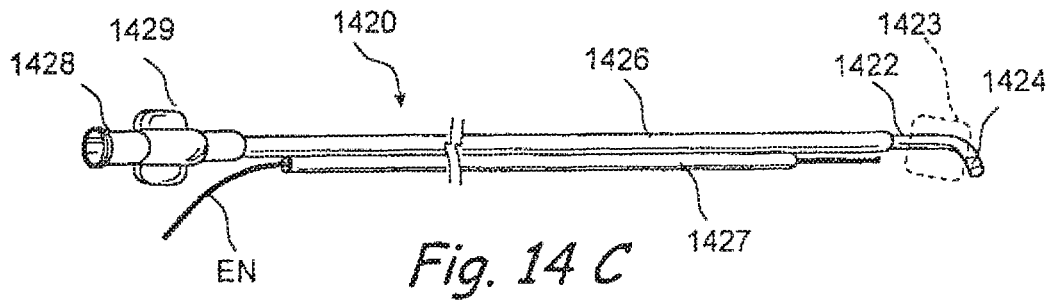
Figure 14:
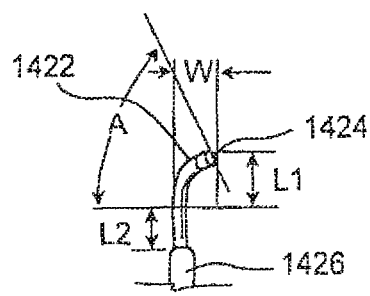
Figure 14:
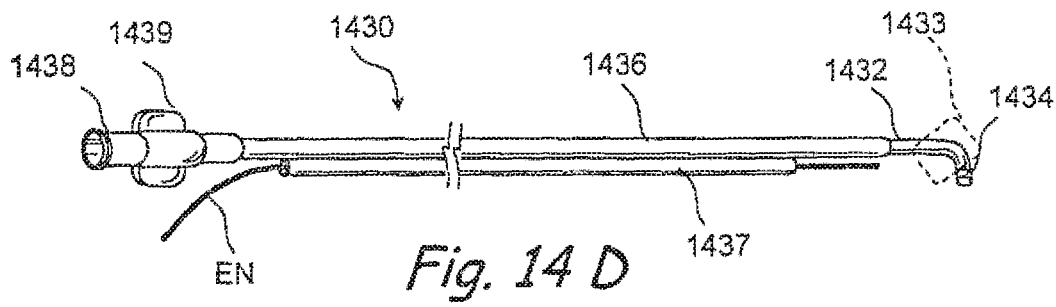
Figure 14:
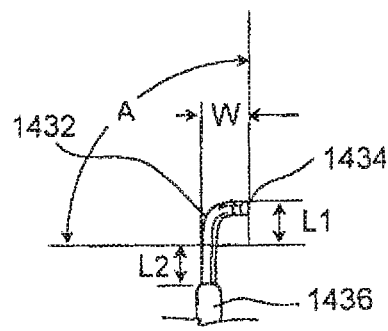
Figure 14:
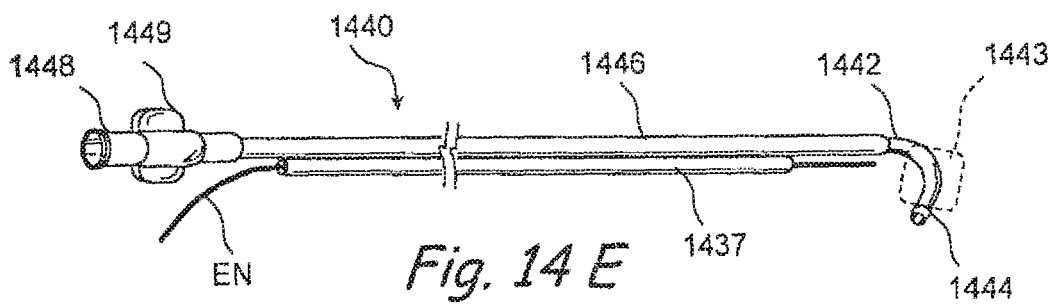
Figure 14:
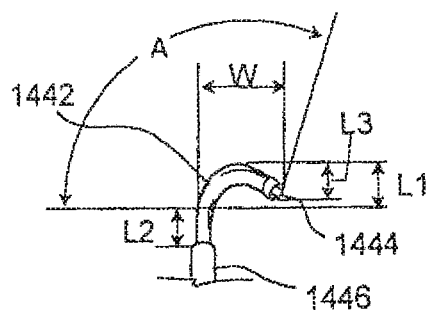

The guide catheters disclosed herein may comprise a bent, curved or angled distal region to allow easier access to a paranasal sinus ostium. Such guide catheters may further comprise mechanisms to introduce an endoscope along the guide catheters. For example, FIGS. 14A through 14E' show side views of embodiments of guide devices comprising bent, curved or angled distal regions and mechanisms to introduce an endoscope along the guide catheters. One or more of these guide devices may be provided as a part of the system for diagnosing or treating paranasal sinus pathologies. FIG. 14A shows a side view of a first embodiment of a guide device comprising a substantially straight distal portion. Guide device 1400 comprises an elongate tube 1402. Elongate tube 1402 may be made of suitable biocompatible materials such polymers e.g. Nylon, Pebax, etc. In a preferred embodiment, the material of elongate tube 1402 has Rockwell hardness in the range of about 70R to about 110R. In this preferred embodiment, the distal portion is flexible enough to prevent or reduce damage to the anatomy. Yet, the distal portion is rigid enough to retain its shape as one or more devices are passed through guide device 1400. Furthermore, the distal portion is rigid enough to enable a user to use the distal portion to displace anatomical structures. The distal portion of elongate tube 1402 comprises a curved, bent or angled region curved at an angle of less then 5 degrees. In one embodiment, distal portion of elongate tube 1402 is substantially straight. The inner surface of elongate tube 1402 may be lined by a lubricious coating or a tubular lubricious liner made of a suitable biocompatible material such as PTFE. In one embodiment, the outer diameter of elongate tube 1402 is around 0.134+/−0.005 inches. An optional dilating balloon 1403 may be located on the distal region of guide device 1400. Dilating balloon may be made of suitable biocompatible materials including, but not limited to PET, Nylon, PVC, etc. The distal portion of elongate tube 1402 comprises an atraumatic tip 1404. Atraumatic tip 1404 may be made of suitable biocompatible materials including, but not limited to Pebax, etc. Atraumatic tip 1404 prevents or reduces damage to the anatomy caused by the distal end of guide device 1400. In one embodiment, length of atraumatic tip 1404 is 0.08+/−0.04 inches and the material of tip 1404 has Shore Durometer hardness in the range of about 35D to about 72D. Guide device 1400 further comprises a hypotube 1406. Hypotube 1406 may be made of suitable biocompatible materials such as stainless steel 304, titanium, Nickel-titanium alloy (e.g., Nitinol), polymers such as Nylon etc. In one embodiment, the outer diameter of hypotube 1406 is 0.154+/−0.005 inches. In one embodiment of a method of constructing guide device 1400, a stainless steel hypotube 1406 is bonded to an elongate tube 1402 such as a Nylon elongate tube 1402 to increase the strength of elongate tube 1402. In one embodiment, hypotube 1406 is heat bonded to elongate tube 1402. One or more openings, perforations or holes may be located an hypotube 1406 to enable material of elongate tube 1402 to melt into the one or more openings, perforations or holes. When the melted material of elongate tube 1402 solidifies, an additional mechanical bonding is created between hypotube 1406 and elongate tube 1402. Guide device 1400 further comprises an endoscope introducing mechanism for introducing an endoscope EN. In the embodiment shown in FIG. 14A, the endoscope introducing mechanism comprises a side lumen 1407 through which a suitable flexible endoscope EN can be introduced in the anatomy. The proximal end of guide device 1400 comprises a hub 1408. In one embodiment, hub 1408 is a female luer hub. Hub 1408 may have wings 1409 to enable a user to turn guide device 1400. In one embodiment, the axial length of guide device 1400 is 5+/−0.25 inches. In one embodiment, the inner diameter of guide device 1400 is around 0.1 inches. The distal portion of guide device 1400 may comprise a radiopaque marker. In one embodiment, the radiopaque marker is a platinum/iridium marker band. The guide device design shown in FIG. 14A is especially suited for trans-nasal access of the sphenoid sinuses.

FIG. 14B shows a side view of a first embodiment of a guide device comprising a bent, angled or curved distal portion. Guide device 1410 comprises an elongate tube 1412. Elongate tube 1412 may be made of suitable biocompatible materials such polymers e.g. Nylon, Pebax, etc. Elongate tube 1412 comprises a substantially straight proximal portion enclosed by a hypotube and a distal portion comprising a curved, bent or angled region. The angle of the curved, bent or angled region of the distal portion can range from 5 degrees to 45 degrees. In this embodiment, distal portion of elongate tube 1412 is bent by an angle of around 30 degrees. The inner surface of elongate tube 1412 may be lined by a lubricious coating or a tubular lubricious liner made of a suitable biocompatible material such as PTFE. In one embodiment, the outer diameter of elongate tube 1412 is around 0.134+/−0.005 inches. An optional dilating balloon 1413 may be located on the distal region of guide device 1410. Dilating balloon may be made of suitable biocompatible materials including, but not limited to PET, Nylon, PVC, etc. The distal portion of elongate tube 1412 comprises an atraumatic tip 1414. Atraumatic tip 1414 may be made of suitable biocompatible materials including, but not limited to Pebax, etc. Atraumatic tip 1414 prevents or reduces damage to the anatomy caused by the distal end of guide device 1410. In one embodiment, length of atraumatic tip 1414 is 0.08+/−0.04 inches. Guide device 1410 further comprises a hypotube 1416 covering the proximal portion of elongate tube 1412. Hypotube 1416 may be made of suitable biocompatible materials such as stainless steel 304, titanium, Nickel-titanium alloy (e.g., Nitinol), polymers such as Nylon etc. In one embodiment, the outer diameter of hypotube 1416 is 0.154+/−0.005 inches. In one embodiment of a method of constructing guide device 1410, a stainless steel hypotube 1416 is bonded to a Nylon elongate tube 1412. Guide device 1410 further comprises an endoscope introducing mechanism for introducing an endoscope EN. In the embodiment shown in FIG. 14B, the endoscope introducing mechanism comprises a side lumen 1417 through which a suitable flexible endoscope EN can be introduced in the anatomy. The proximal end of guide device 1410 comprises a hub 1418. In one embodiment, hub 1418 is a female luer hub. Hub 1418 may have wings 1419 to enable a user to turn guide device 1410. Wings 1419 may be aligned in the plane of the curve of the distal tip as an indicator of the position and orientation of the distal tip in the anatomy. In one embodiment, the axial length of guide device 1410 is 5+/−0.25 inches. In one embodiment, the inner diameter of guide device 1410 is around 0.1 inches. The distal portion of guide device 1410 may comprise a radiopaque marker. In one embodiment, the radiopaque marker is a platinum-iridium marker band. FIG. 14B' shows an enlarged view of the distal portion of the guide device in FIG. 14B. FIG. 14B' shows elongated tube 1412 enclosed by hypotube 1416. Distal end of elongated tube 1412 comprises atraumatic tip 1414. Several parameters defined hereafter characterize the design of the distal portion of guide device 1410. The width of the distal end of guide device 1410 is called W as shown. The length measured from the proximal-most point on the distal curved portion of elongate tube 1412 to the distal-most part of the distal tip is called L1. L1 is measured along the linear direction of the straight proximal portion of guide device 1410 as shown in FIG. 14B'. The length of the straight region of elongate tube 1412 from the distal end oft hypotube 1416 till the proximal most point on the curved region of the distal portion is called L2. In one particular embodiment, W is 0.34+/−0.08 inches, L1 is 0.46+/−0.08 inches, L2 is 0 to 2 inches and the radius of curvature of the distal curved region of elongate tube 1412 is 0.180 inches. The guide device design shown in FIGS. 14B and 14B' is especially suited for trans-nasal access of the sphenoid sinuses.

FIG. 14C shows a side view of a second embodiment of a guide device comprising a bent, angled or curved distal portion. The design of guide device 1420 is similar to the design of guide device 1410. Guide device 1420 comprises an elongate tube 1422. The distal portion of elongate tube 1422 comprises a curved, bent or angled region curved at an angle ranging from 30 degrees to 140 degrees. In this embodiment, distal portion of elongate tube 1422 is bent by an angle of around 70 degrees. An optional dilating balloon 1423 may be located on the distal region of guide device 1420. Dilating balloon may be made of suitable biocompatible materials including, but not limited to PET, Nylon, PVC, etc. The distal portion of elongate tube 1422 comprises an atraumatic tip 1424. Guide device 1420 further comprises a hypotube 1426. Guide device 1420 further comprises an endoscope introducing mechanism for introducing an endoscope EN. In the embodiment shown in FIG. 14C, the endoscope introducing mechanism comprises a side lumen 1427 through which a suitable flexible endoscope EN can be introduced in the anatomy. The proximal end of guide device 1420 comprises a hub 1428. In one embodiment, hub 1428 is a female luer hub. Hub 1428 may have wings 1429 to enable a user to turn guide device 1420. FIG. 14C' shows an enlarged view of the distal portion of the guide device in FIG. 14C. FIG. 14C' shows elongated tube 1422 enclosed by hypotube 1426. Distal end of elongated tube 1422 comprises atraumatic tip 1424. In one particular embodiment, W is 0.45+/−0.08 inches, L1 is 0.32+/−0.08 inches, L2 is 0 to 2 inches and the radius of curvature of the distal curved region of elongate tube 1422 is 0.180 inches. The guide device design shown in FIGS. 14C and 14C' is especially suited for trans-nasal access of the frontal sinuses.

FIG. 14D shows a side view of a second embodiment of a guide device comprising a bent, angled or curved distal portion. The design of guide device 1430 is similar to the design of guide device 1410. Guide device 1430 comprises an elongate tube 1432. The distal portion of elongate tube 1432 comprises a curved, bent or angled region curved at an angle ranging from 70 degrees to 135 degrees. In this embodiment, distal portion of elongate tube 1432 is bent by an angle of around 90 degrees. An optional dilating balloon 1433 may be located on the distal region of guide device 1430. Dilating balloon may be made of suitable biocompatible materials including, but not limited to PET, Nylon, PVC, etc. The distal portion of elongate tube 1432 comprises an atraumatic tip 1434. Guide device 1430 further comprises a hypotube 1436. Guide device 1430 further comprises an endoscope introducing mechanism for introducing an endoscope EN. In the embodiment shown in FIG. 14D, the endoscope introducing mechanism comprises a side lumen 1437 through which a suitable flexible endoscope EN can be introduced in the anatomy. The proximal end of guide device 1430 comprises a hub 1438. In one embodiment, hub 1438 is a female luer hub. Hub 1438 may have wings 1439 to enable a user to turn guide device 1430. FIG. 14D' shows an enlarged view of the distal portion of the guide device in FIG. 14D. FIG. 14D' shows elongated tube 1432 enclosed by hypotube 1436. Distal end of elongated tube 1432 comprises atraumatic tip 1434. In one particular embodiment, W is 0.39+/−0.080 inches, L1 is 0.25+/−0.08 inches, L2 is 0 to 2 inches and the radius of curvature of the distal curved region of elongate tube 1432 is 0.180 inches. W may be as small as 5 mm with a corresponding reduction in the radius of curvature of the distal curved region of elongate tube 1432. The guide device design shown in FIGS. 14D and 14D' is especially suited for trans-nasal access of the maxillary sinuses.

FIG. 14E shows a side view of a third embodiment of a guide device comprising a bent, angled or curved distal portion. The design of guide device 1440 is similar to the design of guide device 1410. Guide device 1440 comprises an elongate tube 1442. The distal portion of elongate tube 1442 comprises a curved, bent or angled region curved at an angle ranging from 140 degrees to 120 degrees. In this embodiment, distal portion of elongate tube 1442 is bent by an angle of around 110 degrees. An optional dilating balloon 1443 may be located on the distal region of guide device 1440. Dilating balloon may be made of suitable biocompatible materials including, but not limited to PET, Nylon, PVC, etc. The distal portion of elongate tube 1442 comprises an atraumatic tip 1444. Guide device 1440 further comprises a hypotube 1446. Guide device 1440 further comprises an endoscope introducing mechanism for introducing an endoscope EN. In the embodiment shown in FIG. 14E, the endoscope introducing mechanism comprises a side lumen 1447 through which a suitable flexible endoscope EN can be introduced in the anatomy. The proximal end of guide device 1440 comprises a hub 1448. In one embodiment, hub 1448 is a female luer hub. Hub 1448 may have wings 1449 to enable a user to turn guide device 1440. FIG. 14E' shows an enlarged view of the distal portion of the guide device in FIG. 14E. FIG. 14E' shows elongated tube 1442 enclosed by hypotube 1446. Distal end of elongated tube 1442 comprises atraumatic tip 1444. In one particular embodiment, W is 0.46+/−0.08 inches, L1 is 0.25+/−0.08 inches, L2 is 0 to 0.5 inches and the radius of curvature of the distal curved region of elongate tube 1442 is 0.180 inches. L1 and W may be smaller than 0.25+/−0.08 inches and 0.46+/−0.08 inches respectively. The guide device design shown in FIGS. 14E and 14E' is especially suited for trans-nasal access of the maxillary sinuses.

Figure 15:
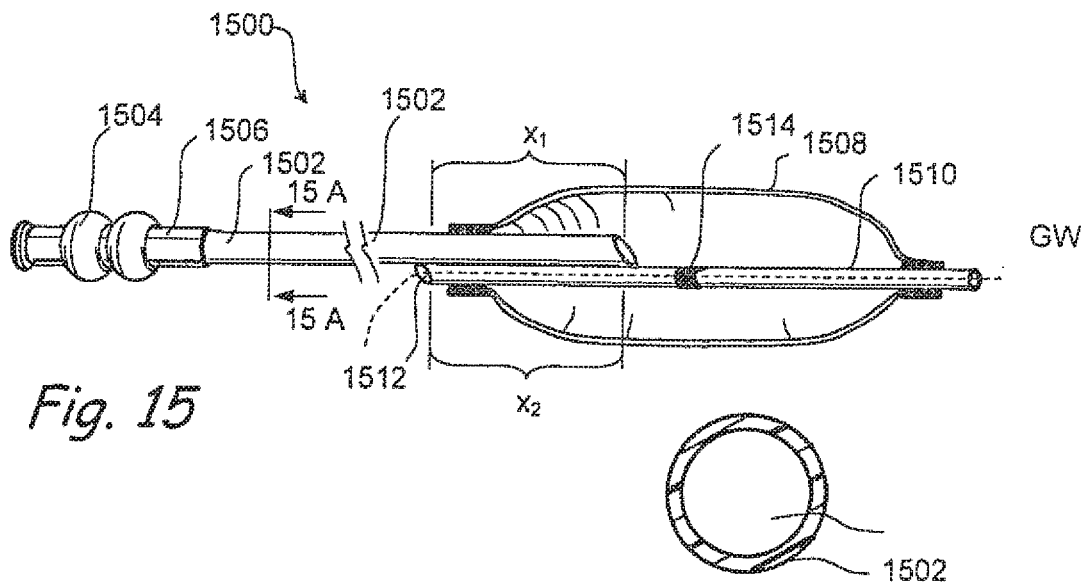
FIG. 15 is a perspective view of a baloon catheter constructed of first and second tubes such that a short lumen (e.g., a rapid exchange guidewire lumen) extends through the balloon.
Figure 15A:
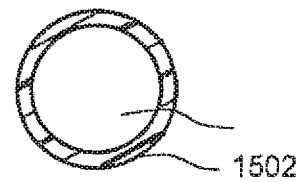
FIG. 15A is a cross sectional view through line 15A-15A of FIG. 15.

FIG. 15A shows a cross sectional view of a first embodiment of a balloon catheter comprising a short guidewire lumen. Balloon catheter 1500 comprises a hollow, elongate shaft 1502. Elongate shaft 1502 can be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. The proximal end of elongate shaft 1502 is connected to a suitable inflation port 1504 such as a female luer lock. In one embodiment, balloon catheter 1500 further comprises an elongate hypotube 1506 located between elongate shaft 1502 and inflation port 1504. The distal end of elongate shaft 1504 is attached to the proximal end of a balloon 1508 such that inflation port 1504 is in fluid communication with balloon 1508. Balloon 1508 can be made of suitable biocompatible materials including, but not limited to PET, Nylon, PVC, polyethylene, polyurethane, Pebax, etc. Balloon 1508 also encloses a guidewire shaft 1510 enclosing a guidewire lumen 1512. The length of guidewire shaft 1510 is less then the length of elongate shaft 1502. In one embodiment, the length of guidewire shaft 1510 ranges from 5-12 cm. The proximal region of guidewire shaft 1512 is connected sideways to elongate shaft 1502 such that guidewire shaft 1512 is substantially parallel to elongate shaft 1502. The proximal end of guidewire shaft 1512 is located in a region proximal to balloon 1508. The distal end of guidewire lumen 1512 is located in a region distal to balloon 1508. Guidewire shaft 1512 enables balloon catheter 1500 to be introduced over a suitable guidewire into an anatomical region. In one embodiment, the length of balloon catheter 1500 from the distal end of inflation port 1504 till the distal end of guidewire shaft 1510 is around 30 cm. In one embodiment, guidewire shaft 1512 comprises a navigational marker such as a radiopaque marker band 1514. Similar navigational markers may be present on other embodiments of balloon catheters disclosed herein and in the patent applications incorporated herein by reference. In one embodiment, two navigational markers are present on the balloon catheter shaft corresponding to the proximal and distal end respectively of the working length of the balloon. In another embodiment, a navigational marker is present on the balloon shaft corresponding to the proximal end of the balloon. Such a navigational marker is especially useful to determine the position of the proximal end of the balloon relative to the distal end of an introducing catheter when the balloon catheter is introduced through the introducing catheter. The user tracks the position of the navigational marker relative to the distal end of the introducing catheter to ensure that the balloon is not inflated within the introducing catheter. Examples of such a navigational marker include, but are not limited to a radiopaque marker band for fluoroscopic visualization, a colored ring for endoscopic visualization, etc.

Figure 16:
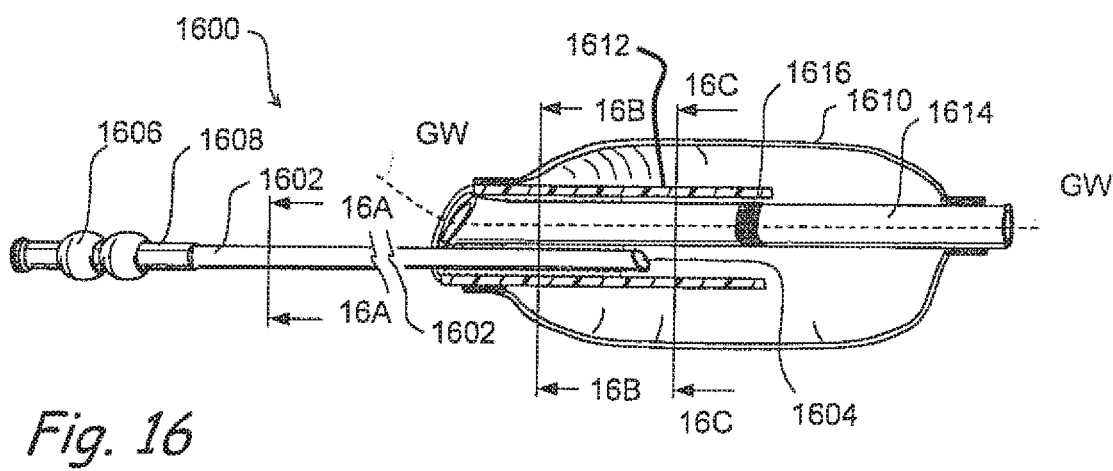
FIG. 16 is a perspective view of a baloon catheter constructed of first, second and third tubes such that a short lumen (e.g., a rapid exchange guidewire lumen) extends through the balloon.
Figure 16A:
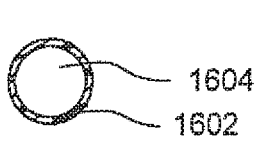
FIG. 16A is a cross sectional view through line 16A-16A of FIG. 16.
Figure 16B:
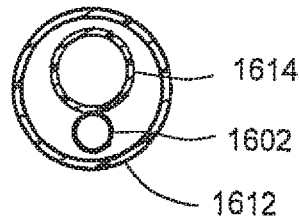
FIG. 16B is a cross sectional view through line 16B-16B of FIG. 16.
Figure 16C:
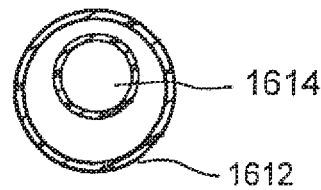
FIG. 16C is a cross sectional view through line 16C-16C of FIG. 16.

FIGS. 16-16C show a balloon catheter 1600 constructed of a first shaft 1602 having a first lumen 1604, a second shaft 1612 and third shafts such that a short lumen (e.g., a rapid exchange guidewire lumen) extends through the balloon. Balloon catheter 1600 comprises a hollow, first elongate shaft 1602. First elongate shaft 1602 can be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. First elongate shaft 1602 comprises a first lumen 1604. The proximal end of elongate shaft 1602 is connected to a suitable hub such as a female luer lock 1606 which is in fluid communication with first lumen 1604. A hypotube 1608 may be provided between female luer lock 1606 and first elongate shaft 1602. The distal end of first lumen 1604 is in fluid communication with a balloon 1610 located on the distal region of first elongate shaft 1602. Thus, first lumen 1604 can be used to inflate balloon 1610. Balloon 1610 can be made of suitable biocompatible materials including, but not limited to PET, Nylon, PVC, polyethylene, polyurethane, Pebax, etc. The distal region of first elongate shaft 1602 is enclosed by a second elongate shaft 1612. Second elongate shaft 1612 further encloses a region of a third elongate shaft 1614 comprising a lumen. The proximal end of the lumen of third elongate shaft 1614 is located proximal to balloon 1610. The distal end of the lumen of third elongate shaft 1614 is located distal to balloon 1610. In one embodiment, the length of third elongate shaft 1614 may range from 5-12 cm. Third elongate shaft 1614 enables balloon catheter 1600 to be introduced over a suitable guidewire GW into an anatomical region. Third elongate shaft 1614 may further comprise a navigational marker such as a radiopaque marker band 1616 made of suitable radiopaque materials such as platinum-iridium alloys, etc. In one embodiment, the length of balloon catheter 1600 from the proximal end of female luer lock 1606 till the distal end of third elongate shaft 1614 is around 30 cm.

FIG. 16A is a cross sectional view through line 16A-16A of FIG. 16. FIG. 16A shows a cross sectional view of elongate shaft 1602 comprising first lumen 1604. FIG. 16B is a cross sectional view through line 16B-16B of FIG. 16. FIG. 16B shows second elongate shaft 1612 enclosing first elongate shaft 1602 and third elongate shaft 1614. FIG. 16C is a cross sectional view through line 16C-16C of FIG. 16. FIG. 16C shows second elongate shaft 1612 enclosing third elongate shaft 1614.

Figure 17:
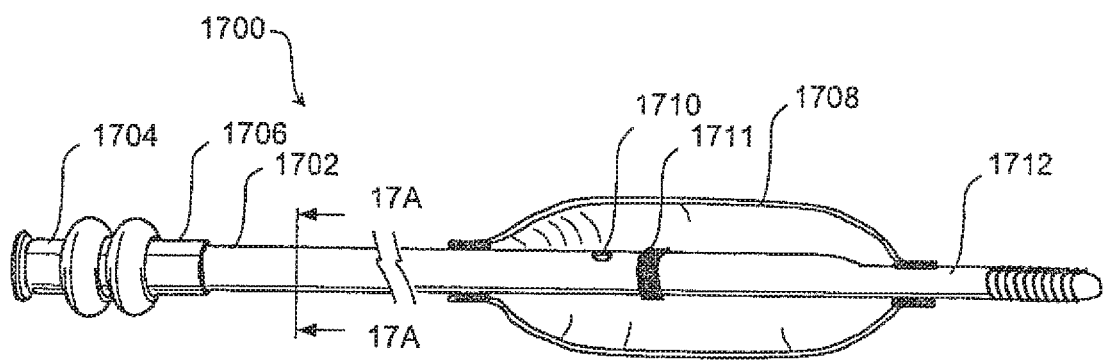
FIG. 17 is a broken, partially sectional view of a balloon catheter having a stylet permanently positioned therein and a guidewire tip protruding from its distal end.

FIG. 17 shows a balloon catheter 1700 that comprises an elongate shaft 1702 having a mandrel 1712 positioned therein. The elongate shaft 1702 may be made of suitable biocompatible materials including, but not limited to polyethylene, Pebax, Nylon, etc. Elongate shaft 1702 encloses a lumen. The proximal end of elongate shaft 1702 comprises a suitable hub 1704. In one embodiment, hub 1704 is a female luer lock. A strain relief tubing 1706 may be present between hub 1704 and elongate shaft 1702. The distal region of elongate shaft 1702 comprises a balloon 1708. Balloon 1708 may be made of suitable biocompatible materials including, but not limited to PET, Nylon, PVC, polyethylene, polyurethane, Pebax, etc. The region of elongate shaft 1702 enclosed by balloon 1708 comprises an opening 1710 that provides fluid communication between the lumen of elongate shaft 1702 and balloon 1708. The lumen of elongate shaft 1702 can thus be used to inflate balloon 1708. Elongate shaft 1702 may further comprise a navigational marker such as a radiopaque marker band 1711 located on the distal region of elongate shaft 1702. A mandrel 1712 is located in lumen 1703 such that a distal region of mandrel 1712 emerges out of the distal end of elongate shaft 1702. The distal end of elongate shaft 1702 is connected to mandrel 1712 by a fluid-tight seal. FIG. 17A shows a cross sectional view of balloon catheter 1700 of FIG. 17 through plane 17A-17A. FIG. 17A shows elongate shaft 1702 enclosing a lumen and mandrel 1712 located in the lumen.

Figure 17B:
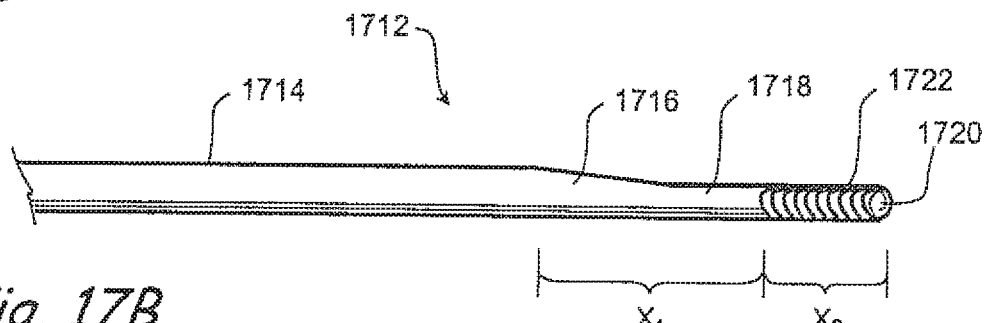
FIG. 17B is a partial perspective view of the stylet of the balloon catheter shown in FIG. 17.
Figure 17A:
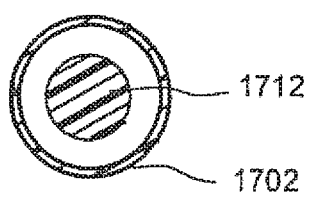
FIG. 17A is a cross sectional view through line 17A-17A of FIG. 17.

FIG. 17B shows an enlarged perspective view of the mandrel in FIG. 8F. Mandrel 1712 comprises a proximal region 1714, a tapering region 1716, a distal region 1718 and a distal tip 1720. Proximal region 1714 may have an outer diameter ranging from 0.005 inches to 0.12 inches. Distal tip 1720 emerges out of the distal end of elongate shaft 1702 and can be used to navigate balloon catheter 1700 through the anatomy or to insert balloon catheter 1700 through an anatomical opening or passageway. Distal tip 1720 further comprises a coil 1722 coiled around a region of or around the entire length of distal tip 1720. Coil 1722 can be made of suitable materials including, but not limited to platinum, stainless steel, nickel-titanium alloys such as Nitinol, etc. In a particular embodiment, the distance from the proximal end of tapering region 1716 to the distal end of distal region 1718 ranges from 2 to 6 cm and the length of distal tip ranges from 1 to 3 cm. Mandrel 1712 may be made of suitable biocompatible materials including, but not limited to stainless steel, Nickel-titanium alloy (e.g., Nitinol), etc.

Figure 18:
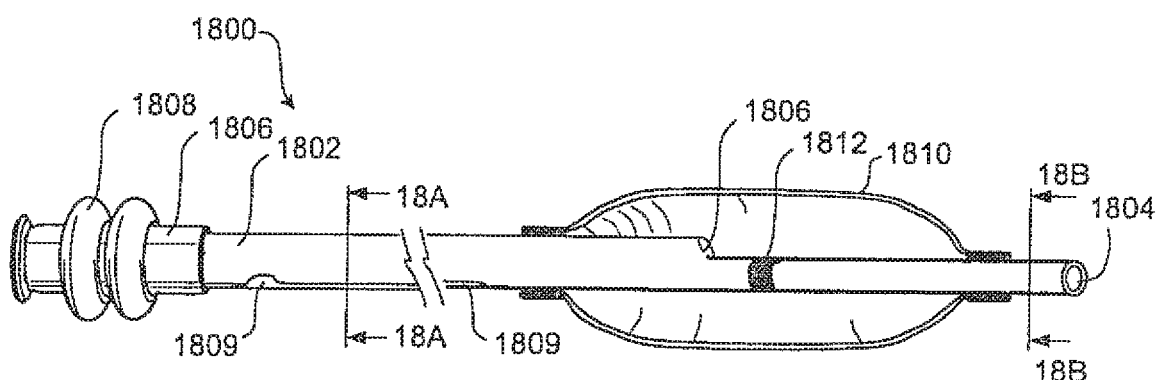
FIG. 18 is a broken, partially sectional view of a balloon catheter having a side slit.
Figure 18A:
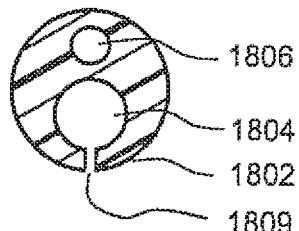
FIG. 18A is a cross sectional view through line 18A-18A of FIG. 18.
Figure 18B:
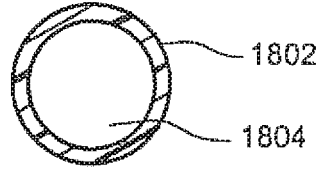
FIG. 18B is a cross sectional view through line 18B-18B of FIG. 18.

FIG. 18 shows a balloon catheter 1800 comprising a shaft 1802 having a lumen 1804 with a side slit 1809 and a balloon 1810 or other expandable dilator. Elongate shaft 1802 can be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. In the particular example shown, the elongate shaft 1802 comprises a first lumen 1804 useable as a guidewire lumen and a second lumen 1806 useable to inflate the balloon 1810. The proximal end of first lumen 1804 may be occluded proximal to a slit 1809. The proximal region of elongate shaft 1802 may be connected to a hub 1808 which is in fluid communication with second lumen 1806. In this example, hub 1808 is a female luer lock. The slit 1809 extends along one side of the shaft 1802 proximal to the balloon 1810 and slows a guidewire to be pulled laterally out of the first lumen 1804 and through the slit 1809, This enables balloon catheter 1800 to be advanced or withdrawn over a suitable elongate devices such as a guidewire such that the a portion of the suitable elongate device enters balloon catheter 1800 from the distal end of first lumen 1804 and exits out of balloon catheter 1800 through slit 1807. A balloon 1810 is located on the distal region of elongate shaft 1802. Balloon 1810 may be made of suitable biocompatible materials including, but not limited to PET, Nylon, PVC, polyethylene, polyurethane, Pebax, etc. A navigational marker 1812 such as a radiopaque marker band may be located on the region of elongate shaft 1802 enclosed by balloon 1810. The distal end of first lumen 1804 terminates in a region distal to balloon 1810. The distal end of second lumen 1806 is in fluid communication with balloon 1810 such that second lumen 1806 can be used to inflate or deflate balloon 1810. FIG. 18A shows a cross sectional view of the balloon catheter in FIG. 18 through the plane 18A-18A. FIG. 18A shows a cross section of elongate sheath 1802 showing first lumen 1804, second lumen 1806 and slit 1807. FIG. 18B shows a cross sectional view of the balloon catheter in FIG. 18 through the plane 18B-18B. FIG. 18B shows a cross section of elongate sheath 1802 showing first lumen 1804.

FIGS. 19-19C show a catheter device 1900 comprising an elongate catheter shaft 1902, a balloon 1906 or other expandable dilator mounted on elongate shaft 1902 and apparatus such as capacitance plates 1908, 1910 located on opposite sides of the balloon or other dilator for determining its diameter. In the example shown, the elongate shaft 1902 may be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. Elongate shaft 1902 may comprise a guidewire lumen 1904 to enable balloon catheter 1900 to be advanced or withdrawn over a suitable guidewire. The distal region of balloon catheter 1900 comprises a balloon 1906 made of suitable biocompatible materials including, but not limited to PET, Nylon, PVC, polyurethane, etc. Balloon 1906 may be inflated or deflated by introducing or withdrawing fluid through a balloon inflation lumen present in elongate shaft 1902. Balloon 1906 further comprises a first capacitance plate 1908 and a second capacitance plate 1910. First capacitance plate 1908 and second capacitance plate 1910 may be made of suitable biocompatible metals sheets. First capacitance plate 1908 and second capacitance plate 1910 are electrically insulated from balloon 1906 and the fluid used to inflate balloon 1906. First capacitance plate 1908 is connected by a first insulated wire 1912 to a source of electrical supply. Second capacitance plate 1910 is connected by a second insulated wire 1914 to the source of electrical supply such that an electric field is generated between first capacitance plate 1908 and second capacitance plate 1910. This causes balloon 1906 to behave like a capacitor with a capacitance depending on various properties such as distance between first capacitance plate 1908 and second capacitance plate 1910, type of inflation fluid, size of first capacitance plate 1908 and second capacitance plate 1910, etc. As balloon 1906 is inflated or deflated, the distance between first capacitance plate 1908 and second capacitance plate 1910 changes. This in turn changes the capacitance. The change in capacitance can be measured through first insulated wire 1912 and second insulated wire 1914 to non-invasively measure the degree of inflation of balloon 1906. Using this method, the degree of inflation of balloon 1906 may be measured without the use of ionizing radiation. First insulated wire 1912 and second insulated wire 1914 may be further insulated from the surroundings by a layer of insulating covering 1916. Insulating covering 1916 covers first insulated wire 1912, second insulated wire 1914 and elongate shaft 1902. FIG. 19A shows a side view of the balloon catheter in FIG. 19. FIG. 19A shows balloon catheter 1900 comprising elongate shaft 1902, balloon 1906, first capacitance plate 1908 and first insulated wire 1912 connected to first capacitance plate 1908. FIGS. 19B and 19C show cross sectional views of the balloon catheter in FIG. 19 through planes 19B-19B and 19C-19C respectively. FIG. 19B shows a cross section of shaft 1902 comprising guidewire lumen 1904 and a balloon inflation lumen 1918. In this embodiment, balloon inflation lumen 1918 is annular and is coaxial to guidewire lumen 1904. Shaft 1902 further comprises first insulated wire 1912 and second insulated wire 1914 covered by insulating covering 1916. FIG. 19C shows a cross section through balloon 1906 showing shaft 1902 enclosing guidewire lumen 1904.

Also shows are first capacitance plate 1908 and second capacitance plate 1910 located on balloon 1906.

FIGS. 20-20C show a balloon catheter 2000 comprising an elongate catheter shaft 2002, a balloon 2006 or other expandable dilator mounted on the catheter shaft 2002 and apparatus for determining the diameter of the balloon 2006, such as capacitance plates 2008, 2010, one of which is located on the wall of the balloon 2006 and the other of which is located on a portion of the catheter shaft 2016 that extends through the balloon 2006. The elongate shaft 2002 can be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. Elongate shaft 2002 may comprise a guidewire lumen 2004 to enable balloon catheter 2000 to be advanced or withdrawn over a suitable guidewire. Balloon 2006 made of suitable biocompatible materials including, but not limited to PET, Nylon, PVC, polyethylene, polyurethane, Pebax, etc. Balloon 2006 may be inflated or deflated by introducing or withdrawing fluid through a balloon inflation lumen present in elongate shaft 2002. First capacitance plate 2008 and second capacitance plate 2010 are electrically insulated from balloon 2006 and the fluid used to inflate balloon 2006. First capacitance plate 2008 is connected by a first insulated wire 2012 to a source of electrical supply. Second capacitance plate 2010 connected by a second insulated wire 2014 to the source of electrical supply such that an electric field is generated between first capacitance plate 2008 and second capacitance plate 2010. This causes balloon 2006 to behave like a capacitor with a capacitance depending on various properties such as distance between first capacitance plate 2008 and second capacitance plate 2010, type of inflation fluid, size of first capacitance plate 2008 and second capacitance plate 2010, etc. As balloon 2006 is inflated or deflated, the distance between first capacitance plate 2008 and second capacitance plate 2010 changes. This in turn changes the capacitance. The change in capacitance can be measured through first insulated wire 2012 and second insulated wire 2014 to non-invasively measure the degree of inflation of balloon 2006. Using this method, the degree of inflation of balloon 2006 may be measured without the use of ionizing radiation. First insulated wire 2012 and second insulated wire 2014 may be further insulated from the surroundings by a layer of insulating covering 2016. Insulating covering 2016 covers first insulated wire 2012, second insulated wire 2014 and elongate shaft 2002. FIG. 20A shows a side view of the balloon catheter in FIG. 20. FIG. 20A shows balloon catheter 2000 comprising elongate shaft 2002, balloon 2006, first capacitance plate 2008 and first insulated wire 2012 connected to first capacitance plate 2008. FIGS. 20B and 20C show cross sectional views of the balloon catheter in FIG. 20A through planes 20B-20B and 20C-20C respectively. FIG. 20B shows a cross section of shaft 2002 comprising guidewire lumen 2004 and a balloon inflation lumen 2018. In this embodiment, balloon inflation lumen 2018 is annular and is coaxial to guidewire lumen 2004. Shaft 2002 further comprises first insulated wire 2012 and second insulated wire 2014 covered by insulating covering 2016. FIG. 20C shows a cross section through balloon 2006 showing shaft 2002 enclosing guidewire lumen 2004. Also shows are first capacitance plate 2008 and second capacitance plate 2010 located on balloon 2006.

In an alternate embodiment, a balloon catheter comprises a first capacitance plate located on or within the balloon material; a second capacitance plate located on or within the balloon material and one or more shaft plates located on or within the balloon shaft. A user measures a first capacitance between the first capacitance plate and the one or more shaft plates. Also, the user measures a second capacitance between the second capacitance plate and the one or more shaft plates. The first capacitance and the second capacitance may be used to measure the degree of balloon inflation and also to measure the evenness of balloon inflation.

Any of the balloon catheters comprising capacitance measuring means disclosed herein may comprise a temperature sensor to measure the temperature of the inflation fluid. This is useful in cases where the dielectric constant of the inflation fluid varies significantly with temperature.

Figure 21:
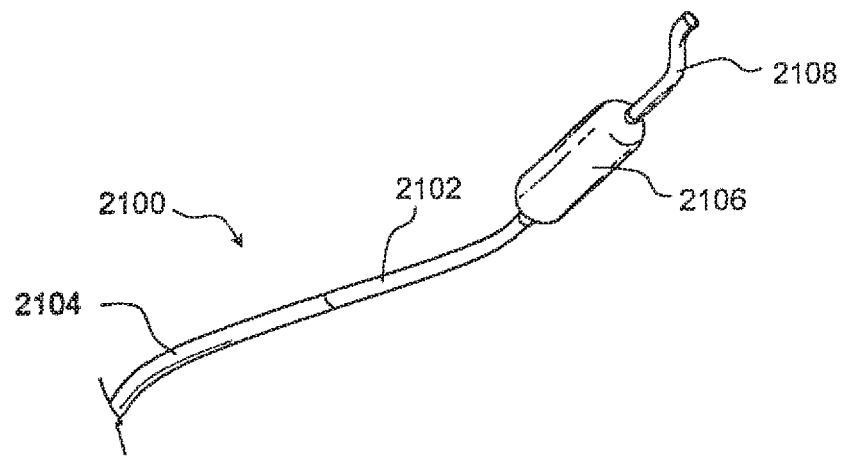
FIG. 21 shows a partial perspective view of a distal portion of balloon catheter having a malleable distal shaft.

FIG. 21 shows a balloon catheter 2100 having a proximal shaft 2104, a malleable distal shaft 2102, an expandable dilator such as a balloon 2106 and, optionally, a distal guide projection such as a wire 2108. This balloon catheter device is useable for a variety of applications including, but not limited to the diagnosis and treatment of certain Ethmoid sinus pathologies. The malleable distal region 2102 may be made of suitable biocompatible materials including, but not limited to stainless steel, Nickel-titanium alloy (e.g., Nitinol), polymer/metal composites, etc. Malleable distal region 2102 may be deformed or shaped by a user during a procedure to allow for easier access and navigation through a target anatomy. The proximal region of the catheter shaft may comprise a substantially non-malleable proximal region 2104. Malleable distal region 2102 comprises a balloon 2106. Balloon 2106 may be made of suitable biocompatible materials including, but not limited to PET, Nylon, PE etc. The length of balloon 2106 ranges from 3 to 40 mm and the inflated diameter of balloon 2106 ranges from 3 to 10 mm. In one embodiment adapted to treat Ethmoid sinuses, the length of balloon 2106 ranges from 3 to 10 mm and the inflated diameter of balloon 2106 ranges from 3 to 6 mm. Balloon catheter 2100 further comprises a navigation mechanism. In one embodiment, the navigation mechanism comprises a length of wire 2108 fixed to the distal end of balloon catheter 2100. The length of wire 2108 may range from 1 to 3 cm. In an alternate embodiment, the navigation mechanism is a rapid exchange lumen through the catheter shaft. In one embodiment, the length of rapid exchange lumen is more then half the total catheter length. For example, in a balloon catheter of total length around 20 cm, the length of the rapid exchange lumen may be about 10 cm. In a balloon catheter of total length around 15 cm, the length of the rapid exchange lumen may be about 13.5 to 10 cm. In an alternate embodiment, the navigation mechanism is an end-to-end lumen through the catheter shaft to allow balloon catheter 2100 to be introduced over a guidewire.

Figure 22:
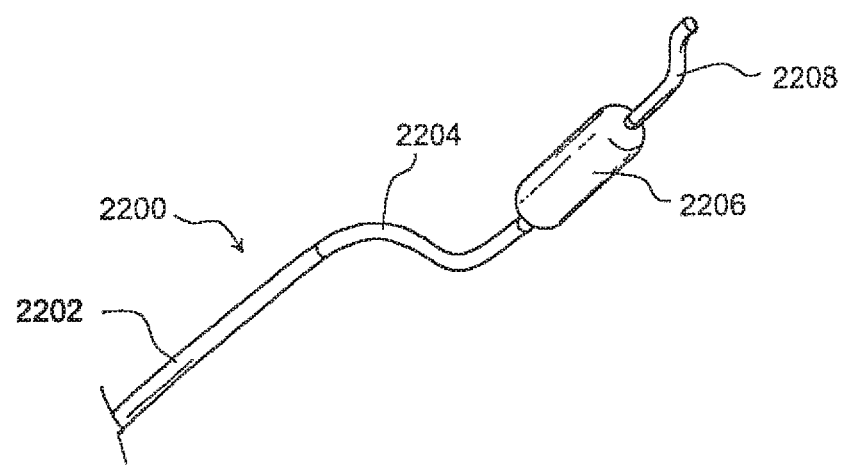
FIG. 22 shows a partial perspective view of a distal portion of balloon catheter having a flexible distal shaft.

FIG. 22 shows balloon catheter 2200 having a proximal shaft 2202, a flexible distal shaft 2204, an expandable dilator such as a balloon 2206 and, optionally, a distal guide projection such as a wire 2208. This balloon catheter device 2200 is useable to perform a variety of diagnostic or therapeutic procedures, some of which are disclosed herein. Such a balloon catheter design comprising a flexible distal shaft is especially suitable for diagnosing or treating pathologies including, but not limited to Ethmoid sinus pathologies. The proximal region 2202 of this catheter is substantially stiff and the distal region 2204 is more flexible than the proximal region 2202. Flexible distal region 2204 may be made of suitable biocompatible materials including, but not limited to Nylon, Pebax, HDPE, LDPE, Polyimide, polymer/metal composites, braided materials, etc. Flexible distal region 2204 is deformed during a procedure to allow for easier access and navigation through a target anatomy. Flexible distal region 2204 comprises a balloon 2206. Balloon 2206 may be made of suitable biocompatible materials including, but not limited to PET, Nylon, PE etc. The length of balloon 2206 ranges from 3 to 40 mm and the inflated diameter of balloon 2206 ranges from 3 to 10 mm. In one embodiment adapted to treat Ethmoid sinuses, the length of balloon 2206 ranges from 3 to 10 mm and the inflated diameter of balloon 2206 ranges from 3 to 6 mm. Balloon catheter 2200 further comprises a navigation mechanism. In one embodiment, the navigation mechanism comprises a length of wire 2208 fixed to the distal end of balloon catheter 2200. The length of wire 2208 may range from 1 to 3 cm. In an alternate embodiment, the navigation mechanism is a rapid exchange lumen through the catheter shaft. The length of the rapid exchange lumen may range from 1 cm to 15 cm. In one embodiment, the length of rapid exchange lumen is more then half the total catheter length. For example, in a balloon catheter of total length around 20 cm, the length of the rapid exchange lumen may be about 10 cm. In a balloon catheter of total length around 15 cm, the length of the rapid exchange lumen may be about 13.5 to 10 cm. In an alternate embodiment, the navigation mechanism is an end-to-end lumen through the catheter shaft to allow balloon catheter 2200 to be introduced over a guidewire.

The balloon catheters disclosed herein and in the patent applications incorporated herein by reference may comprise a balloon of a working length adapted for dilating a particular region of the anatomy. For example, a balloon catheter comprising a balloon of working length ranging from 10-40 mm may be used for treating a disease of the frontal sinuses. Ideally, the balloon comprises a working length ranging from 20-30 mm. The inflated diameter of such balloons may range from 4-10 mm. In another example, a balloon catheter comprising a balloon of working length ranging from 6-10 mm may be used for treating a disease of the maxillary sinuses. In another example, a balloon catheter comprising a balloon of working length ranging from 3-10 mm may be used for dilating the Ethmoid sinuses.

The shafts of the balloon catheters disclosed herein and in the patent applications incorporated herein by reference may comprise one or more angled regions. Such balloon catheters may for example comprise an angled balloon located on an angled region of the shaft. Such balloon catheters are especially suited for treating diseases of the maxillary sinuses.

The balloon catheters disclosed herein and in the patent applications incorporated herein by reference may comprise a substantially compliant balloon. Such a substantially compliant balloon may be inflated at an inflation pressure preferably less than 4 atmospheres. Such balloon catheter may be used for example to dilate the mucosa of anatomical regions such as passageways leading to paranasal sinuses. The step of dilation of the mucosa may or may not include dilation of the underlying bony structures. Such balloon catheters may also be used for sizing anatomical regions such as passageways leading to paranasal sinuses. This is performed by inflating the substantially compliant balloon by a fluid comprising radiopaque contrast and observing the radiographic image of the balloon. The step of sizing an anatomical region may be performed before and/or after the step of dilating the anatomical region.

The balloon catheters disclosed herein and in the patent applications incorporated herein by reference may be introduced in the anatomy by a variety of manual introducing tools. Examples of such manual introducing tools include, but are not limited to forceps (e.g. giraffe forceps), pincers, tweezers, tongs, etc. Such manual introducing tools may have curved, bent, angled or substantially straight distal regions. For example, a balloon catheter may be grasped in a region proximal to the balloon by a forceps and then introduced in the target anatomy.

The balloon catheters disclosed herein and in the patent applications incorporated herein by reference may be used to deliver heat or cold, a gas, electromagnetic energy in the visible spectrum, etc.

If a balloon catheter is used for performing multiple procedures, it may be useful to refold the balloon of the balloon catheter after each procedure to lower the profile of the balloon before the next procedure.

FIGS. 23-23D show a balloon folding tool 2300 useable to facilitate folding of a balloon 2308 mounted on a balloon catheter 2306. The balloon folding tool 2300 comprises a rigid body having a central bore or folding channel 2302 formed therein, such folding channel 2306 having a diameter that is less than the fully inflated balloon diameter. A plurality of side channels or parallel channels 2304 are located adjacent to and substantially parallel with the central bore or folding channel 2302 and are connected to the central bore or folding channel 2302 through slots or elongate openings. The balloon 2308 is insertable into the central bore or folding channel 2302 while in a less than fully inflated state and, thereafter, may be fully or partially inflated to cause separate portions of the balloon 2308 to pass through the each slot and into each side channel 2304 as seen in FIG. 23C. Thereafter, the balloon may be deflated such that each separate portion of the balloon that has passed into each side channel will form a separate wing of the deflated balloon 2308, as seen in FIG. 23D. The wings are thereafter foldable (e.g., to a creased, wrapped or furled state) to provide a collapsed balloon shape. The number of side or parallel channels 2304 and the resultant number of wings formed in the deflated balloon 2308 may vary depending of the size of the balloon 2308 and the manner in which it is intended to fold or furl the balloon. In some embodiments, about 2-6 side channels 2304 will be used, providing about 2-6 wings on the deflated balloon 2308.

The elongate body of the folding tool 2300 may be made of suitable biocompatible materials including, but not limited to metals e.g. titanium, stainless steel, etc.; polymers e.g. PVC, Nylon, DELRIN®, Polycarbonate, ABS, etc. Folding tool 2300 further comprises a balloon folding channel 2302. In one embodiment, the cross section of balloon folding channel 2302 is substantially uniform along the length of folding tool 2300. In another embodiment, the cross sectional size of balloon folding channel 2302 is larger at the proximal end of folding tool 2300. In this embodiment, the cross sectional size of balloon folding channel 2302 gradually reduces towards the distal end of folding tool 2300 to facilitate loading a balloon catheter in balloon folding channel 2302. In one embodiment, balloon folding channel 2302 extends through the entire length of the elongate body. In another embodiment, balloon folding channel 2302 extends through a part of the length of the elongate body. Folding tool 2300 further comprises one or more parallel channels 2304. Parallel channels 2304 are aligned substantially parallel to balloon folding channel 2302 and overlap lengthwise to balloon folding channel 2302 as shown in FIG. 23. FIG. 23A shows a perspective view of a balloon catheter 2306 comprising a balloon 2308 being introduced into folding tool 2300.

FIGS. 23B and 23C show an end view of the folding tool of FIG. 23 showing the steps of an embodiment of a method of folding the balloon of a balloon catheter. FIG. 23D shows a cross sectional view through a folded balloon 2308. In FIG. 23B, balloon catheter 2306 is introduced into balloon folding channel 2302. Thereafter, in FIG. 23C, balloon 2308 is partially inflated such that regions of balloon 2308 extend in parallel channels 2304. Thereafter, balloon 2308 is deflated and a vacuum is created in balloon 2308. This creates one or more ridges in balloon 2308. Thereafter, folding tool 2308 is turned to obtain one or more folds in balloon 2308. Thereafter, balloon 2308 is pulled out of folding tool 2300 to obtain a folded balloon as shown in FIG. 23O. Such a folded balloon may thereafter be introduced in a small diameter tube to further reduce the profile of the balloon.

In an alternate method of folding balloon 2308, balloon catheter 2306 is introduced into balloon folding channel 2302. Thereafter, balloon 2308 is partially inflated such that regions of balloon 2308 extend in parallel channels 2304. Thereafter, balloon 2308 is deflated and a vacuum is created in balloon 2308. This causes one or more ridges to be created in balloon 2308. Thereafter, balloon 2308 is pulled out of folding tool 2300. Balloon 2308 is then folded manually to obtain a folded balloon with a low profile.

Similarly, other folding tools comprising one or more folding channels, folding grooves, folding cavities, folding slits, etc. may be used for folding one or more balloons of the balloon catheters disclosed herein.

Figure 24:
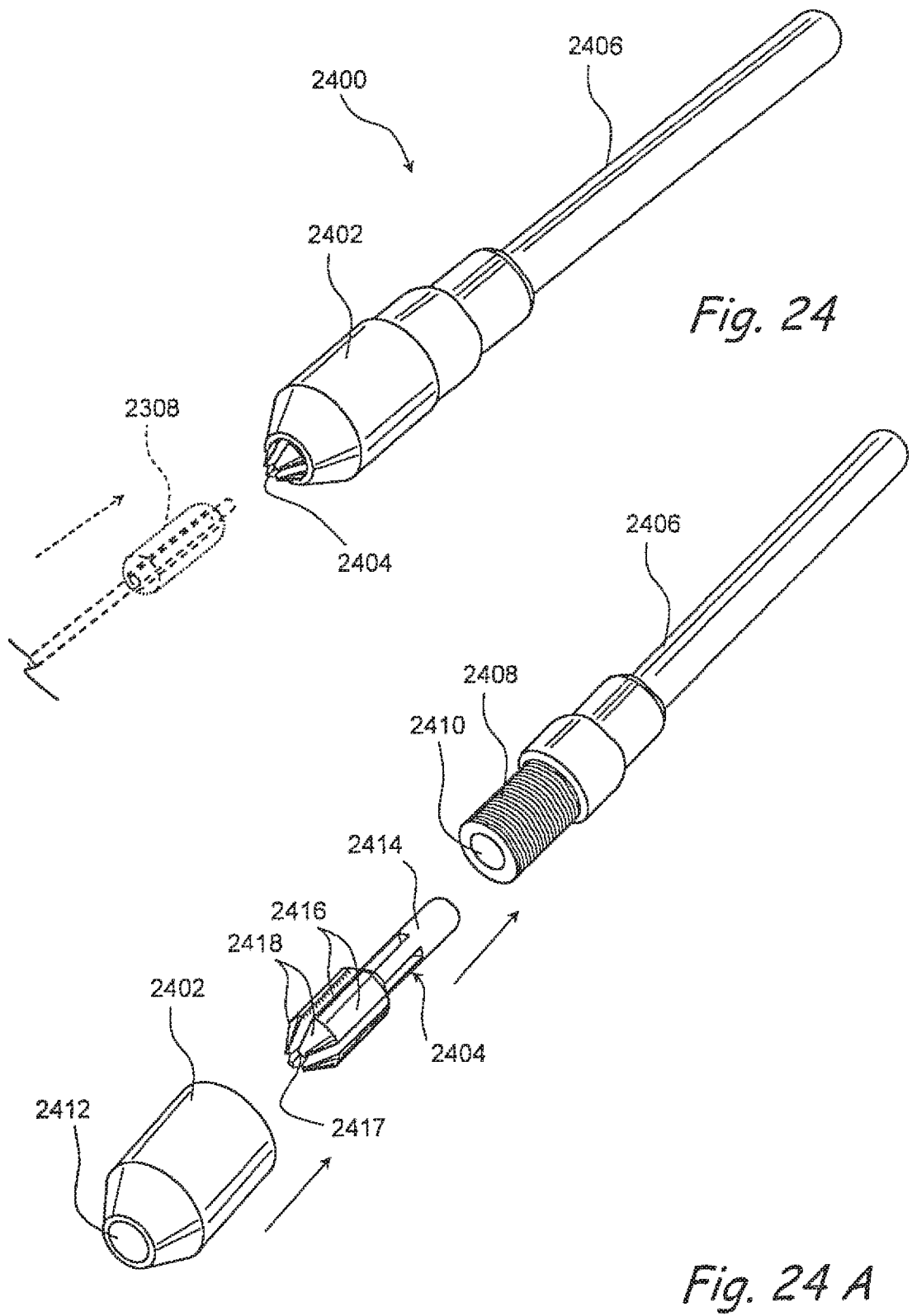
FIG. 24 is a front perspective view of a balloon compressing apparatus of the present invention.

FIG. 24 shows a balloon compressing apparatus 2400 that is useable to facilitate folding of a balloon 2308 mounted on a catheter. This balloon compressing apparatus 2400 generally comprises a clamping element 2404 having a plurality of compression members 2416 disposed radially about a central cavity 2417. The compression members 2416 are spaced apart from each other such that gaps exist between adjacent compression members 2416. The compression members 2416 are moveable from non-compressing positions where the central cavity had a first diameter to compressing positions where the central cavity has a second diameter that is smaller than the first diameter. The balloon 2308 is insertable into the central cavity 2417 while the compression members are in their non-compressing positions and, thereafter, the compression members are moveable to their compressing positions, thereby compressing portions of the balloon 2308 and causing any inflation fluid to be forced out of the balloon and causing portions of the balloon to protrude outwardly into the gaps between the compression members. Such protrusion into the gaps between compression members 2416 forms a plurality of wings on the deflated balloon 2308. The wings are thereafter foldable (e.g., to a creased, wrapped or furled state) to provide a collapsed balloon shape. The number of gaps and the resultant number of wings formed in the deflated balloon 2306 may vary depending of the size of the balloon 2308 and the manner in which it is intended to fold or furl the balloon. In some embodiments, about 2-6 side gaps will be used, providing about 2-6 wings on the deflated balloon 2308.

In the particular example shown in the figures, folding tool 2400 comprises a screw cap 2402 that encloses a clamping element 2404. The distal end of clamping element 2404 and the distal end of screw cap 2402 are in contact with a distal handle 2406. Clamping element 2404, screw cap 2402 and distal handle 2406 may be made of suitable biocompatible materials including, but not limited to metals e.g. stainless steel, titanium, etc.; polymers e.g. PVC, Polycarbonate, Delrin®, Nylon, ABS, etc. FIG. 24A shows an exploded view of the various components of the balloon folding tool of FIG. 24. Distal handle 2406 comprises an elongate body comprising screw threads 2408 located on the proximal end of the elongate body. Distal handle 2406 may comprise a lumen 2410. The outer surface of distal handle 2406 may be roughened to increase the grip of a user on distal handle 2406. In one embodiment, outer surface of distal handle 2406 is roughened by knurling. Screw cap 2402 comprises a lumen 2412. The inner surface of screw cap 2402 comprises screw threads that screw over screw threads 2408 of distal handle 2406. The outer surface of screw cap 2402 may be roughened to increase the grip of a user on screw cap 2402. In one embodiment, outer surface of screw cap 2402 is roughened by knurling. Clamping element 2404 is enclosed by screw cap 2402 and distal handle 2406. Clamping element 2404 comprises a distal body 2414. The proximal end of distal body is connected to two or more clamping arms 2416. One or more gaps are located between two or more clamping arms 2416. Clamping arms 2416 enclose a central cavity 2417 that is substantially collinear with lumen 2412 of screw cap 2402. The proximal ends of clamping arms 2416 comprise a tapered region 2418. Tightening screw cap 2402 over distal handle 2406 causes a region of screw cap 2402 to slide over tapered region 2418. This in turn displaces the proximal regions of clamping arms 2416 in a radially inward direction. Thus, clamping arms 2416 can clamp on a device located in the hollow region that is enclosed by clamping arms 2416. Similarly, loosening screw cap 2402 over distal handle 2406 causes clamping arms 2416 to release a device located in the hollow region that is enclosed by clamping arms 2416. In one embodiment of a method of folding a balloon of a balloon catheter, an uninflated balloon is inserted in the hollow region that is enclosed by clamping arms 2416. Thereafter, the balloon is partially inflated such that portions of the balloon enter one or more gaps located between two or more clamping arms 2416. Thereafter, screw cap 2402 is tightened over distal handle 2406. Thereafter, the balloon is deflated. Simultaneously, folding tool 2400 is rotated to create one or more folds in the balloon.

Folding tool 2300 and folding tool 2400 may comprise a centering element to align the shaft of a balloon catheter with the central axis of the folding tools. In one embodiment, the centering element comprises a centering wire attached to the folding tool. The shaft of the balloon catheter slides over the centering wire. This aligns the shaft of the balloon catheter with the central axis of the folding tool.

Figure 25:
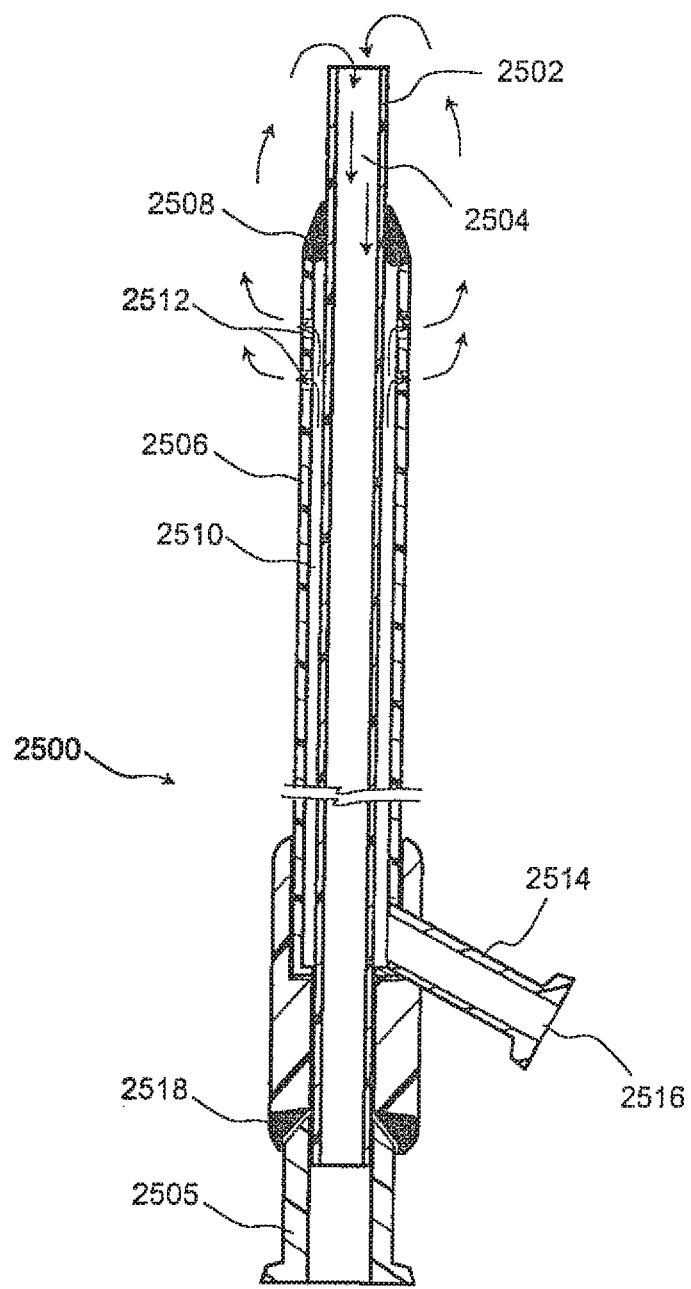
FIG. 25 shows a longitudinal sectional view of an embodiment of a catheter for simultaneous aspiration and irrigation of an anatomical region.

FIG. 25 shows a catheter 2500 that is useable for simultaneous irrigation and aspiration. This catheter 2500 comprises an inner tube 2502 enclosing an inner lumen 2504. Inner tube 2502 may be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. The proximal end of inner tube 2502 comprises a suitable hub such as a female luer lock 2505. Inner tube 2502 is surrounded by an outer tube 2506. Outer tube 2506 may be made of suitable biocompatible materials including, but not limited to metals e.g. stainless steel, titanium, Nickel-titanium alloy (e.g., Nitinol), etc.; polymers e.g. Nylon, Pebax, PEEK, polyethylene, etc. In one embodiment, inner tube 2502 has an inner diameter of 0.040 inches and an outer diameter of 0.050 inches and outer tube 2506 has an inner diameter of 0.080 inches and an outer diameter of 0.092 inches. The distal end of outer tube 2506 is attached to inner tube 2502 to create a fluid-tight distal seal 2508. The region between outer tube 2506 and inner tube 2502 encloses an outer lumen 2510. The distal region of outer tube 2506 comprises one or more openings or perforations 2512 that are in fluid communication with outer lumen 2510. The proximal end of outer tube 2506 is enclosed by a Y-connector 2514 as shown in FIG. 25. A side arm of Y-connector 2514 is in fluid communication with outer lumen 2510. The proximal end of the side arm comprises a hub 2516 such as a luer lock. Y-connector 2514 is attached to female luer lock 2505 to create a fluid-tight proximal seal 2518. In one embodiment, catheter 2500 further comprises a hypotube surrounding outer tube 2506. Catheter 2500 may be used to simultaneously introduce fluids into and suction fluids out of a target anatomy such as a paranasal sinus, openings or passageways leading to a paranasal sinus, etc. In one method embodiment, outer lumen 2510 is used to introduce one or more fluids into the target anatomy. Inner lumen 2504 is used to suction out one or more fluids from the target anatomy. In another embodiment, inner lumen 2504 is used to introduce one or more fluids into the target anatomy. Outer lumen 2510 is used to suction out one or more fluids from the target anatomy. In this embodiment, one or more openings or perforations 2512 may be made larger to prevent blockage by materials being suctioned into outer lumen 2510.

Figure 26:
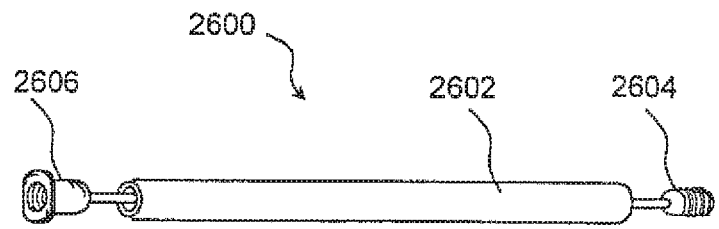
FIG. 26 is a perspective view of a navigation adapter device that is attachable to a variety of other devices to facilitate use of those other devices in image guided surgical or interventional procedures.
Figure 26:
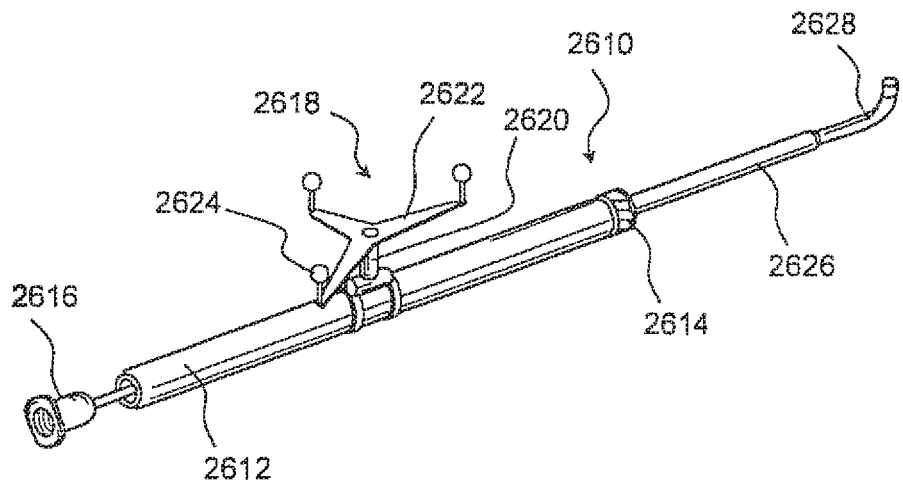
Figure 26:
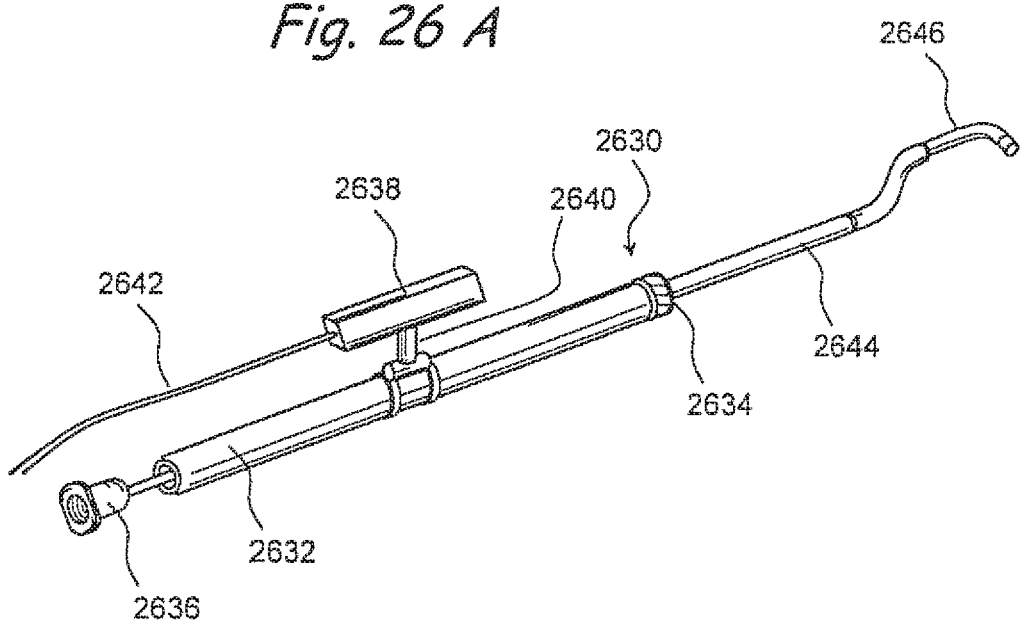

Image guided surgery (IGS) procedures (sometimes referred to as "computer assisted surgery") were first developed for use in neurosurgery and have now been adapted for use in certain ENT surgeries, including sinus surgeries. See, Kingdom T. T., Orlandi R. R., *Image-Guided Surgery of the Sinuses: Current Technology and Applications*, Otolaryngol. Clin. North Am. 37(2): 381-400 (April 2004). Generally speaking, in a typical IGS procedure, a digital tomographic scan (e.g., a CT or MRI scan) of the operative field (e.g., the nasal cavities and paranasal sinuses) is obtained prior to surgery. A specially programmed computer is then used to convert the digital tomographic scan data into a digital map. During surgery, sensors mounted on the surgical instruments send data to the computer indicating the position of each surgical instrument. The computer correlates the data received from the instrument-mounted sensors with the digital map that was created from the preoperative tomographic scan. One or more image(s) is/are then displayed on a monitor showing the tomographic scan along with an indicator (e.g., cross hairs or an illuminated dot) of the real time position of each surgical instrument. In this manner, the surgeon is able to view the precise position of each sensor-equipped instrument relative to the surrounding anatomical structures shown on the tomographic scan. Various embodiments of adapter devices comprising image guidance sensors are disclosed herein. Such adapter devices are adapted to be fitted to one or more devices that are being introduced in the anatomy. This enables a user to view the real time position of the one or more devices that are being introduced in the anatomy. For example, FIGS. 26-26B show a navigation adapter adapter that may be attached to the proximal end of a catheter, seeker, cannula, or any other device to facilitate mounting of navigation unit (e.g., a navigation module, localizer or other apparatus such as sensor(s), emitter(s), transmitter(s), reflector(s), etc. that are useable in conjunction with a navigation system. The particular navigation apparatus may be selected from the various navigation apparatus disclosed herein or in one of the patent applications incorporated herein by reference. In the example of FIG. 26, the navigation adapter 2600 comprises an elongate body 2602 comprising a lumen. Elongate body 2602 may be made of suitable biocompatible materials including, but not limited to metals e.g. stainless steel, titanium, etc.; polymers e.g. Nylon, Pebax, PEEK, polyethylene, etc. The outer surface of elongate body 2602 may be roughened. The distal end of elongate body 2602 comprises a first hub 2604. In one embodiment, first hub 2604 is a male luer lock. The proximal end of elongate body 2602 comprises a second hub 2606. In one embodiment, second hub 2606 is a female luer lock. Navigation adapter 2600 further comprises a tracking system for image guided surgery. Navigation adapter 2600 is adapted to be fixed to a device being introduced in the anatomy. The position of the device can then be tracked using the tracking system located on navigation adapter 2600. Thus, suitable rigid catheters or guide devices may be tracked using existing tracking systems. Similarly, suitable devices with malleable regions may also be tracked using existing tracking systems. The outer surface of elongate body 2602 may be roughened to increase the grip of a user on navigation adapter 2600. In one embodiment, outer surface of elongate body 2602 is roughened by knurling.

FIG. 26A shows a perspective view of an embodiment of a navigation adapter comprising an optical navigation unit. Navigation adapter 2610 comprises an elongate body 2612 comprising a lumen. Elongate body 2612 may be made of suitable biocompatible materials including, but not limited to metals e.g. stainless steel, titanium, nickel-titanium alloys such as Nitinol, etc.; polymers e.g. Pebax, PEEK polyimide, etc.; composites, etc. The distal end of elongate body 2612 comprises a first hub 2614. In one embodiment, first hub 2614 is a male luer lock. The proximal end of elongate body 2612 comprises a second hub 2616. In one embodiment, second hub 2616 is a female luer lock. Navigation adapter 2610 further comprises a navigation unit 2618 for image guided surgery. In one embodiment, navigation unit 2618 is an optical navigation unit. One example of such an optical navigation unit is a BrainLAB surgical instrument adapter. Navigation unit 2618 comprises an attachment region 2620. One end of attachment region 2620 is connected to a series of arms 2622 that extend radially outward from the axis of attachment region 2620. The outer ends of arms 2622 comprise one or more optical energy emitters 2624 that emit optical energy. In one embodiment, optical energy emitters 2624 comprise infrared light emitting LEDs. In another embodiment, optical energy emitters 2624 comprise a reflecting surface that reflects externally generated optical energy reaching the surface of optical energy emitters 2624. A camera is positioned such that it receives the optical energy emitted from optical energy emitters 2624. The camera is then used to track the position and orientation of navigation adapter 2610. Other examples of navigation unit 2618 include, but are not limited to navigation units comprising reflective passive elements, light emitting diodes, transmitters or receivers of energy (e.g. optical energy, radiofrequency energy, etc.), a combination of tow or more of the abovementioned navigation technologies, etc. Navigation adapter 2610 is adapted to be fixed to a diagnostic, therapeutic or access device 2626 being introduced in the anatomy. Device 2626 may comprise a curved, angled or bent distal end 2628. The position of the device can then be tracked using the navigation unit 2618 located on navigation adapter 2610. Thus, suitable rigid catheters or guide devices may be tracked using existing image guidance systems. One example of an optical image guidance system that is useable in ENT and sinus surgery is the LandmarX Evolution® ENT II Image Guidance System available from Medtronic Xomed Surgical Products, Inc., Jacksonville, Fla. The outer surface of elongate body 2612 may be roughened to increase the grip of a user on navigation adapter 2610. In one embodiment, outer surface of elongate body 2612 is roughened by knurling. In one method embodiment, a surgical navigation modality is attached to a rigid device disclosed herein, and the position and orientation of the distal tip of the rigid device is calibrated to the position and orientation of the imaging modality. Thereafter, the rigid device is used to perform a diagnostic, therapeutic or access procedure. If the position or orientation of the rigid device changes with respect to the position or orientation of the surgical navigation modality, the position and orientation of the distal tip of the rigid device may be re-calibrated to the position and orientation of the imaging modality. Such a re-calibration may be necessary for example when a user bends or shapes the distal tip of a rigid device comprising a malleable or shapeable distal tip.

FIG. 26B shows a perspective view of an embodiment of a navigation adapter comprising an electromagnetic navigation unit. In image guidance systems that employ electromagnetic sensors/tracking systems, radiofrequency electromagnetic sensors (e.g., electromagnetic coils) are placed on the surgical instruments and on a localizer frame worn by the patient. A transmitter is positioned near the operative field. The transmitter transmits signals that are received by the instrument-mounted sensors. The tracking system detects variations in the electromagnetic field caused by the movement of the instrument-mounted sensors relative to the transmitter. Examples of commercially available electromagnetic IGS systems that have been used in ENT and sinus surgery include the ENTrak Plus™ and InstaTrak ENT™ systems available from GE Medical Systems, Salt Lake City, Utah. Other examples of electromagnetic image guidance systems that may be modified for use in accordance with the present invention include but are not limited to those available from Surgical Navigation Technologies, Inc., Louiville, Colo., Biosense-Webster, Inc., Diamond Bar, Calif. and Calypso Medical Technologies, Inc., Seattle, Wash. Navigation adapter 2630 comprises an elongate body 2632 comprising a lumen. Elongate body 2632 may be made of suitable biocompatible materials including, but not limited to metals e.g. stainless steel, titanium, etc.; polymers e.g. Nylon, Pebax, PEEK, polyethylene, etc. The distal end of elongate body 2632 comprises a first hub 2634. In one embodiment, first hub 2634 is a male luer lock. The proximal end of elongate body 2632 comprises a second hub 2636. In one embodiment, second hub 2636 is a female luer lock. Navigation adapter 2630 further comprises a radiofrequency electromagnetic sensor 2638 for image guided surgery. Radiofrequency electromagnetic sensor 2638 is attached to elongate body 2632 by an attachment region 2640. In one embodiment, radiofrequency electromagnetic sensor 2638 is attached to an electrical cord 2642 to transmit data from radiofrequency electromagnetic sensor 2638 to an electromagnetic image guidance system. Navigation adapter 2630 is adapted to be fixed to a diagnostic, therapeutic or access device 2644 being introduced in the anatomy. Device 2644 may comprise a shapeable or malleable distal tip 2646. The position of the device can then be tracked using radiofrequency electromagnetic sensor 2638 located on navigation adapter 2630. Thus, suitable rigid catheters or guide devices may be tracked using existing image guidance systems. The outer surface of elongate body 2632 may be roughened to increase the grip of a user on navigation adapter 2630. In one embodiment, outer surface of elongate body 2632 is roughened by knurling.

Similar navigation adapters can be designed wherein electromagnetic sensor 2638 is replaced by other surgical navigation units. Examples of such surgical navigation units include, but are not limited to navigation units comprising reflective passive elements, light emitting diodes, transmitters or receivers of energy (e.g. optical energy, radiofrequency energy, etc.), a combination of tow or more of the abovementioned navigation technologies, etc.

One or more of the devices disclosed herein may comprise a magnetic navigation element located at the distal region of the devices. Such a magnetic navigation element may comprise a permanent magnet or an electromagnet. The distal region of the devices can then be navigated through the anatomy by providing a magnetic field of specified direction and magnitude, positioned externally to the patient.

FIGS. 27A and 27B show top and side views respectively of a surgical hand tool comprising a balloon catheter. FIG. 27A shows a surgical hand tool 2700 comprising a hollow proximal body 2702 made of biocompatible materials including, but not limited to ABS, nylon, polyurethane, polyethylene, etc. Proximal body 2702 encloses a balloon catheter 2704. Balloon catheter 2704 comprises a balloon inflation port 2706 to inflate a balloon on balloon catheter 2704. Balloon inflation port 2706 emerges out of proximal body 2702 through a longitudinal slit 2708 through proximal body 2702 such that balloon catheter 2704 can slide along the axis of proximal body 2702. Balloon inflation port 2706 is connected to a suitable inflating device to inflate the balloon of balloon catheter 2704. In this embodiment, balloon catheter 2704 is introduced into a desired region of the anatomy over a guidewire 2710. The proximal region of guidewire 2710 may comprise a torquing device 2712. A user can use torquing device 2712 to rotate, advance, retract, or torque guidewire 2710. The distal region of proximal body 2702 comprises a suitable hub that allows a guide catheter 2714 to attach to proximal body 2702. In an alternate embodiment, guide catheter 2714 is permanently attached to proximal body 2702. In this embodiment, guide catheter 2714 comprises an elongate tubular element 2716 made of suitable biocompatible materials including, but not limited to PEEK, Pebax, Nylon, Polyimide, ABS, PVC, polyethylene, etc. The proximal region of tubular element 2716 may be covered by a hypotube 2718 made of suitable biocompatible metals or polymers. The proximal end of tubular element 2716 is attached to a suitable hub 2720. Hub 2720 allows the reversible attachment of guide catheter 2714 to proximal body 2702. In one embodiment, hub 2720 is a female luer lock that attached to a suitable hub on proximal body 2702. Thus, various guide catheters can be attached to the distal region of proximal body 2702 to provide access to various anatomical regions. The distal end of tubular element 2716 may comprise an atraumatic tip 2722. The distal end of tubular element 2716 may comprise a curved, bent or angled region. FIG. 27B shows the side view of surgical hand tool 2700 showing a handle 2724 attached to proximal body 2702.

Figures 27C, 27D:
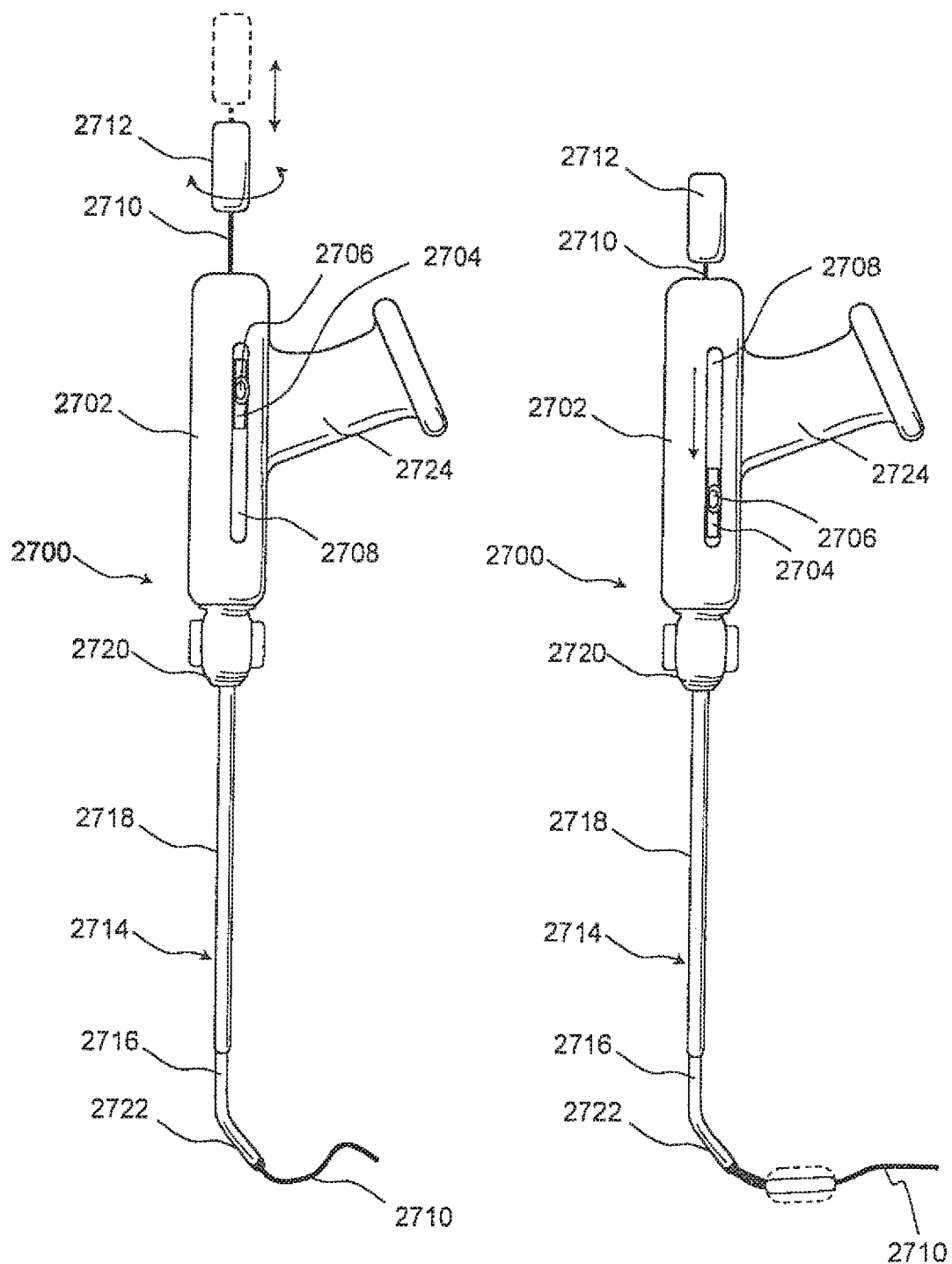
FIGS. 27C-27D show steps in a method for using the dilation device of FIGS. 27A-27B.

FIGS. 27C through 27D show various steps of a method of dilating an anatomical region using the surgical hand tool shown in FIGS. 27A and 27B. In FIG. 27C, surgical hand tool 2700 is introduced in the anatomy. Surgical hand tool 2700 is positioned such that the distal tip of surgical hand tool 2700 is located near an anatomical region to be accessed. Thereafter, a guidewire 2710 is introduced through surgical hand tool 2700 such that the distal tip of guidewire 2710 is located near an anatomical region to be accessed. During this step, guidewire 2710 may be navigated through the anatomy using torquing device 2712. In one embodiment, guidewire 2710 is positioned across a paranasal sinus ostium to be dilated. Thereafter, in FIG. 27D, balloon catheter 2704 is advanced over guidewire 2710 into the anatomy. This is done by pushing balloon inflation port 2706 in the distal direction. Thereafter, balloon catheter 2704 is used to perform a diagnostic or therapeutic procedure. In one embodiment, balloon catheter 2704 is used to dilate an opening leading to a paranasal sinus such as a paranasal sinus ostium.

Figure 27E:
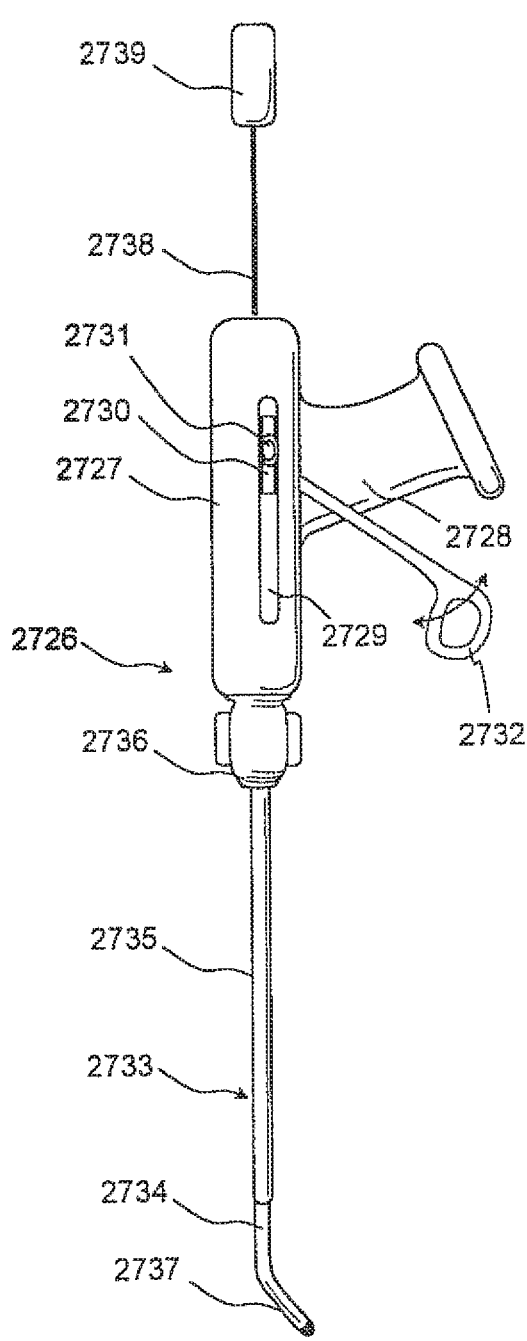
FIG. 27E is a side view of another dilation device useable to dilate openings of paranasal sinuses and other anatomical passages within the ear, nose and throat.

FIG. 27E shows a side view of a first alternate embodiment of a surgical hand tool comprising a balloon catheter. The design of surgical hand tool 2726 is similar to the design of surgical hand tool 2700. Surgical hand tool 2726 comprises a hollow elongate body 2727 made of biocompatible materials including, but not limited to ABS, nylon, polyurethane, polyethylene, etc. Elongate body 2727 is attached to a handle 2728 to allow a user to grasp surgical hand tool 2726. Elongate body 2727 comprises a longitudinal slit 2729. Elongate body 2727 encloses a balloon catheter 2730. Balloon catheter 2730 comprises a balloon inflation port 2731 to inflate a balloon on balloon catheter 2730. Balloon inflation port 2731 emerges out of elongate body 2727 through longitudinal slit 2729 such that balloon catheter 2730 can slide along the axis of elongate body 2727. Balloon catheter 2730 is further connected to a trigger 2732. Trigger 2732 is pivoted on elongate body 2727 such that pulling trigger 2732 in the proximal direction causes balloon catheter 2730 to move in the distal direction. Similarly, pushing trigger 2732 in the distal direction causes balloon catheter 2730 to move in the proximal direction Thus balloon catheter 2730 can be moved by moving trigger 2732. The distal region of elongate body 2727 comprises a suitable hub that allows a guide catheter 2733 to attach to elongate body 2727. In this embodiment, guide catheter 2733 comprises an elongate tubular element 2734 made of suitable biocompatible materials including, but not limited to PEEK, Pebax, Nylon, polyethylene, etc. The proximal region of tubular element 2734 may be covered by a hypotube 2735 made of suitable biocompatible metals or polymers. The proximal end of tubular element 2734 is attached to a suitable hub 2736. Hub 2736 allows the reversible attachment of guide catheter 2733 to elongate body 2727. In one embodiment, hub 2736 is a female luer lock that attached to a suitable hub on elongate body 2727. Thus, various guide catheters can be attached to the distal region of elongate body 2727 to provide access to various anatomical regions. The distal end of tubular element 2734 may comprise an atraumatic tip 2737. The distal end of tubular element 2734 may comprise a curved, bent or angled region. In this embodiment, balloon catheter 2730 is introduced into a desired region of the anatomy over a guidewire 2738. The proximal region of guidewire 2738 may comprise a torquing device 2739. A user can use torquing device 2739 to rotate, advance, retract, or torque guidewire 2738. Surgical hand tool 2726 can be used to introduce balloon catheter 2730 into a desired anatomical region to perform a diagnostic or therapeutic procedure in the anatomical region.

Figure 27F:
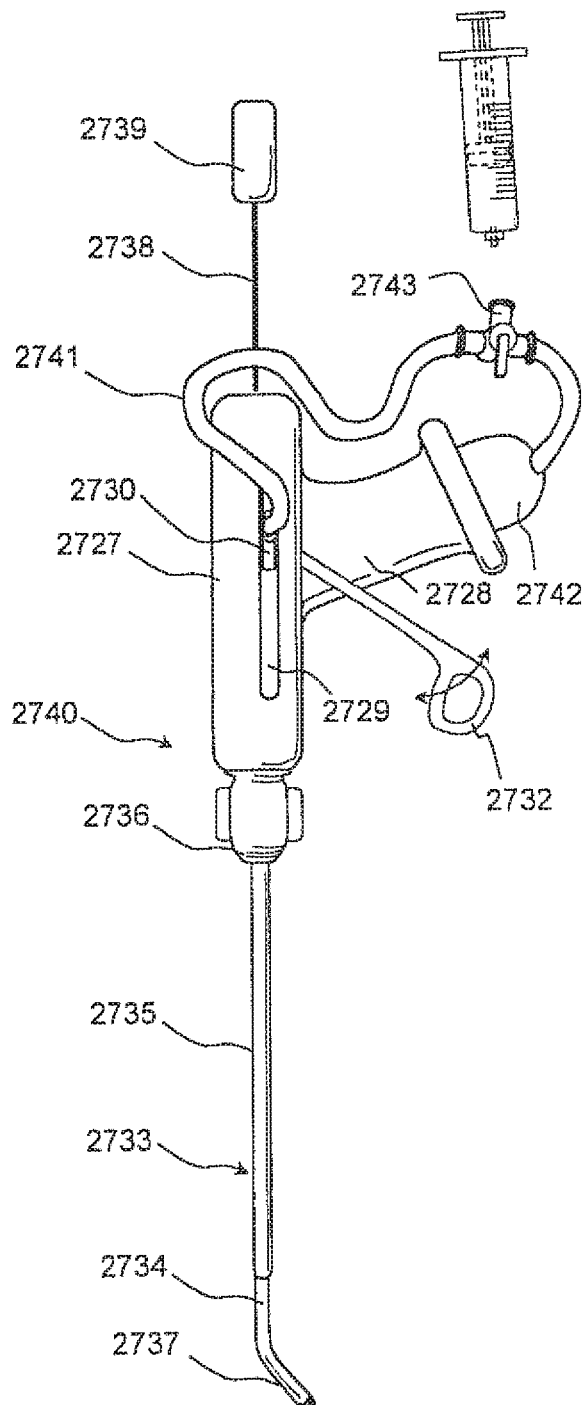
FIG. 27F is a side view of another dilation device which uses compressed inflation fluid to inflate a dilator balloon to dilate openings of paranasal sinuses and other anatomical passages within the ear, nose and throat.

FIG. 27F shows a side view of a second alternate embodiment of a surgical hand tool comprising a balloon catheter. The design of surgical hand tool 2740 is similar to the design of surgical hand tool 2726. Surgical hand tool 2740 further comprises a fluid delivery mechanism to deliver inflating fluid for inflating the balloon of balloon catheter 2730. The fluid delivery mechanism comprises an elongate tube 2741 connected to balloon inflation port 2731. Elongate tube 2741 is further connected to a fluid reservoir 2742. In one embodiment, fluid reservoir 2742 comprises a pressurized gas such as air, nitrogen, carbon dioxide, etc. The delivery of fluid from fluid reservoir 2742 to balloon catheter 2730 is controlled by a valve 2743.

Figure 27G:
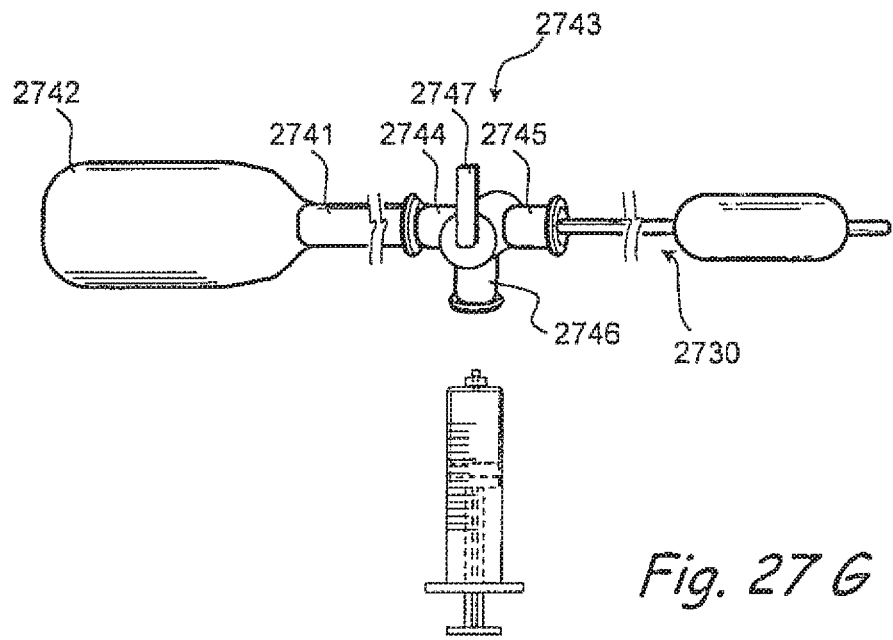
FIG. 27G is a schematic diagram of the valving arrangement of the device shown in FIG. 27F.
Figure 27H:
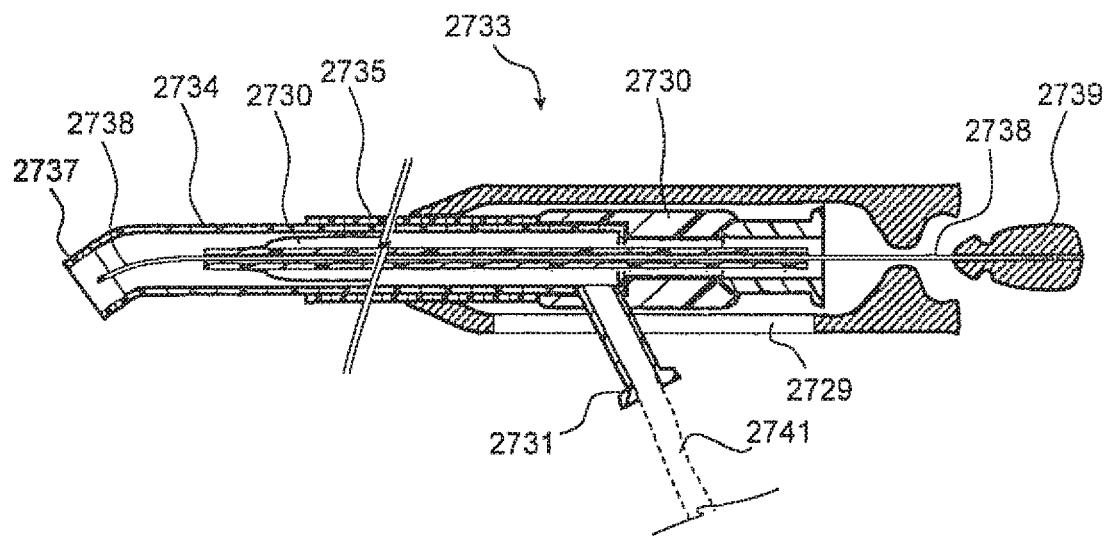
FIG. 27H is a partial sectional view through a portion of the device of FIG. 27A-B.

FIG. 27H shows partial sectional view of the surgical hand tool shown in FIG. 27F. The proximal region of elongate body 2727 comprises longitudinal slit 2729. Elongate body 2727 encloses balloon catheter 2730. The proximal end of balloon catheter 2730 comprises a Y shaped hub. The Y-shaped hub comprises balloon inflation port 2731. Balloon inflation port 2731 in turn is connected to elongate tube 2741. Guidewire 2738 enters elongate body 2727 through an opening in the proximal end of elongate body 2727.

FIG. 27G shows a perspective view of an embodiment of the valve arrangement of the device shown in FIG. 27F. The valve arrangement comprises a three way valve 2743. In one embodiment, three way valve 2743 is a three way luer valve. A first arm 2744 of three way valve 2743 is connected by elongate tube 2741 to fluid reservoir 2742. A second arm 2745 of three way valve 2743 is in fluid communication with the balloon of balloon catheter 2730. A third arm 2746 of three way valve 2743 is connected to a drain or is open to the atmosphere. Third arm 2746 may be connected to a syringe or a source of vacuum to deflate balloon of balloon catheter 2730. Such an arrangement comprising a syringe or a source of vacuum connected to third arm 2746 is especially useful to deflate a non-compliant balloon. Three way valve 2743 further comprises a control knob 2747. In a first position of control knob 2747, a fluid communication is created between first arm 2744 and second arm 2745. In a second position of control knob 2747, a fluid communication is created between second arm 2745 and third arm 2746. A user can turn control knob 2747 in the first position to inflate the balloon of balloon catheter 2730. The user can then turn control knob 2747 in the second position to deflate the balloon of balloon catheter 2730. Other suitable valve arrangements may also be used instead of a three way valve for controllably inflating or deflating the balloon of balloon catheter 2730.

Figure 28:
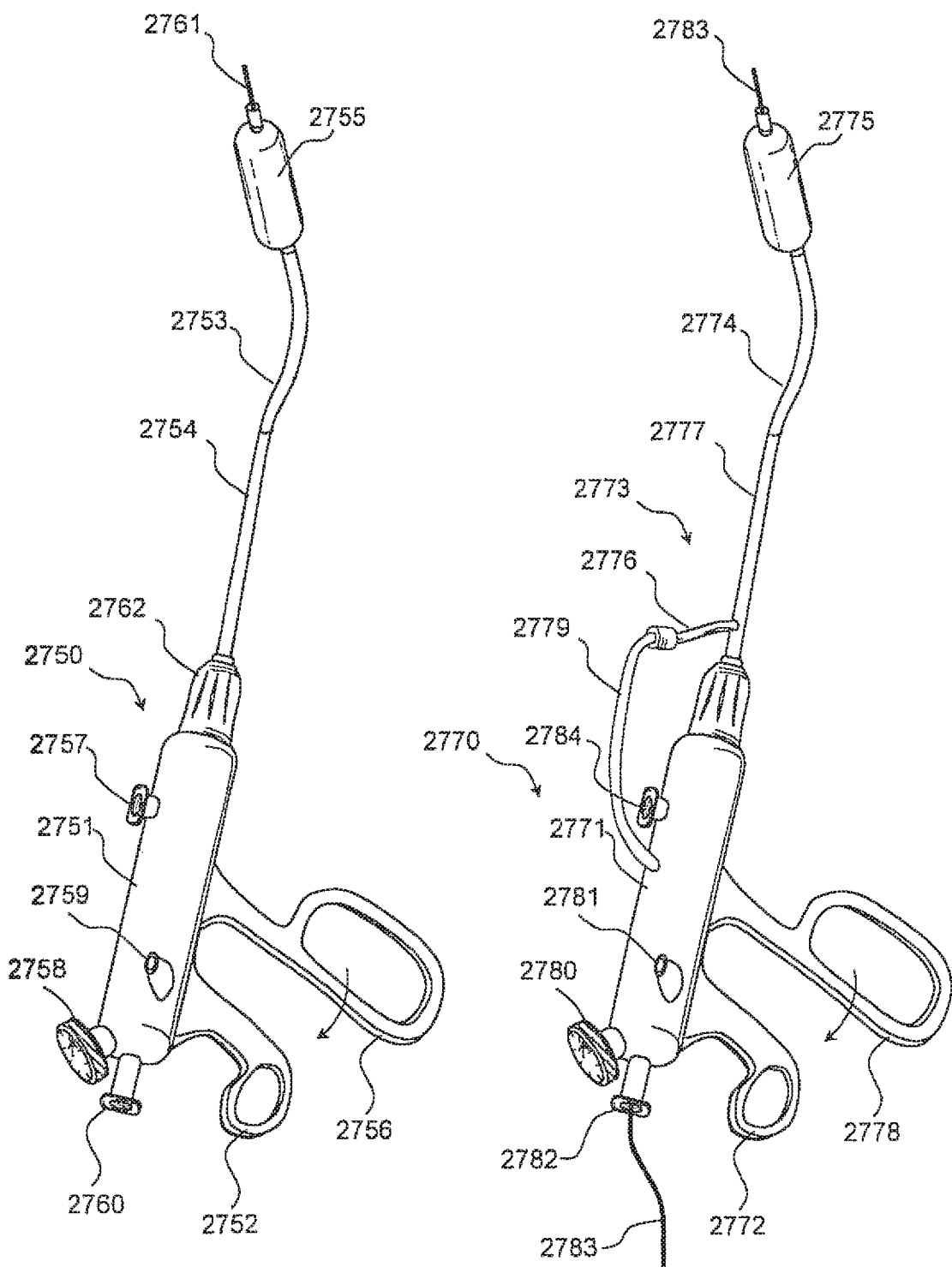
FIG. 28A is a perspective view of a hand grip inflator device attached to a baloon catheter.
FIG. 28B is a perspective view of a balloon dilation device having a hand grip inflator.

FIG. 28A shows a perspective view of an embodiment of a handheld balloon catheter tool. Balloon catheter tool 2750 comprises a proximal region 2751. Proximal region 2751 comprises a handle 2752 to enable a user to hold balloon catheter tool 2750. Balloon catheter tool 2750 further comprises a balloon catheter shaft 2753. In one embodiment, balloon catheter shaft 2753 extends distally from the distal region of proximal region 2751. In another embodiment, balloon catheter shaft 2753 extends till the proximal end of proximal region 2751. Balloon catheter shaft 2753 may further comprise a hypotube 2754 surrounding a region of balloon catheter shaft 2753. The distal region of balloon catheter shaft 2753 comprises an inflatable balloon 2755 that can be used to dilate one or more regions of the anatomy. Balloon 2755 is inflated by a trigger 2756 located adjacent to handle 2752. Trigger 2756 is connected to a plunger that is further connected to an inflating fluid reservoir. Pulling trigger 2756 causes the inflating fluid stored in an inflating fluid reservoir to be delivered to balloon 2755 under pressure. Balloon catheter tool 2750 may further comprise a flushing port 2757 to flush a lumen of balloon catheter shaft 2753. During a procedure, a user inflates balloon 2755 to a desired pressure using the inflating fluid stored in the inflating fluid reservoir. The pressure in balloon 2755 can be measured by a pressure sensor or gauge 2758 that is in fluid communication with the inflating fluid within balloon 2755. Balloon catheter tool 2750 may further comprise a ratcheting mechanism 2759 to allow a user to pull trigger 2756 in incremental steps. This allows the user to inflate balloon 2755 in incremental steps. Similarly, balloon catheter tool 2750 may comprise a ratcheting mechanism to allow a user to release trigger 2756 in incremental steps after inflating balloon 2755. This allows the user to deflate balloon 2755 in incremental steps. In one embodiment, balloon catheter tool 2750 can be advanced over a guidewire to a desired target location in the anatomy. In this embodiment, balloon catheter tool 2750 may further comprise a proximal guidewire port 2760 that is in fluid communication with a guidewire lumen in balloon catheter shaft 2753. This enables balloon catheter tool 2750 to be introduced over a guidewire into the anatomy. In another embodiment, balloon catheter tool 2750 comprises a fixed guidewire 2761 at the distal tip of balloon catheter tool 2750 to navigate balloon catheter tool 2750 through the anatomy. In one embodiment, balloon catheter tool 2750 comprises a rotation knob 2662. Rotation knob 2762 allows a user to rotate balloon catheter shaft 2753. Balloon catheter tool 2750 may further comprise one or more navigational modalities including, but not limited to radio opaque markers, electromagnetic navigational sensors, etc. The distal region of balloon catheter tool 2750 may be introduced in the anatomy through a variety of introducing devices disclosed herein including, but not limited to guide catheter 620 of FIG. 6C.

FIG. 28B shows a perspective view of an embodiment of a detachable handheld balloon catheter inflation tool. Detachable inflation tool 2770 comprises a body 2771 comprising a handle 2772 to enable a user to hold inflation tool 2770. Detachable inflation tool 2770 attaches to a balloon catheter 2773. In one embodiment, a user is provided with a kit comprising a detachable inflation tool 2770 and multiple balloon catheters. In the embodiment shown in FIG. 28B, balloon catheter 2773 comprises an elongate balloon catheter shaft 2774. The distal region of balloon catheter shaft 2774 comprises an inflatable balloon 2775 that can be used to dilate one or more regions of the anatomy. The proximal region of balloon catheter shaft 2774 is connected to a suitable hub 2776 comprising a side port for inflating balloon 2775. In one embodiment, balloon catheter shaft 2774 comprises a hypotube 2777 surrounding a region of balloon catheter shaft 2775. Balloon 2775 is inflated by a trigger 2778 located adjacent to handle 2772. Trigger 2778 is connected to a plunger that is further connected to an inflating fluid reservoir. Pulling trigger 2778 causes an inflating fluid stored in the inflating fluid reservoir to be delivered to balloon 2755 under pressure. The inflating fluid is delivered through a fluid delivery port 2779 that attaches to the side port of hub 2776. During a procedure, a user inflates balloon 2775 to a desired pressure using the inflating fluid stored in the inflating fluid reservoir. The pressure in balloon 2775 can be measured by a pressure sensor or gauge 2780 that is in fluid communication with the inflating fluid within balloon 2775. Detachable inflation tool 2770 may further comprise a ratcheting mechanism 2781 to allow a user to pull trigger 2778 in incremental steps. This allows the user to inflate balloon 2775 in incremental steps. Similarly, detachable inflation tool 2770 may comprise a ratcheting mechanism to allow a user to release trigger 2778 in incremental steps after inflating balloon 2775. This allows the user to deflate balloon 2775 in incremental steps. In one embodiment, the combination of balloon catheter 2773 and balloon catheter tool 2770 can be advanced over a guidewire to a desired target location in the anatomy. In this embodiment, balloon catheter tool 2770 may further comprise a proximal guidewire port 2782 that is in fluid communication with a guidewire lumen in balloon catheter shaft 2774. This enables balloon catheter tool 2770 to be introduced over a guidewire 2783 into the anatomy. In another embodiment, balloon catheter 2773 comprises a fixed guidewire at the distal tip of balloon catheter 2773 to navigate balloon catheter 2773 through the anatomy. In another embodiment, balloon catheter 2773 comprises a rapid exchange lumen.

The rapid exchange lumen enables balloon catheter 2773 to be introduced over a suitable guidewire. Balloon catheter tool 2770 may further comprise a flushing port 2784 to flush a lumen of balloon catheter 2773. Balloon catheter tool 2770 may further comprises one or more navigational modalities including, but not limited to radio opaque markers, electromagnetic navigational sensors, etc. The distal region of balloon catheter 2773 may be introduced in the anatomy through a variety of introducing devices disclosed herein including, but not limited to guide catheter 620 of FIG. 6C.

The balloon catheter tool of FIG. 28A or the detachable handheld balloon catheter inflation tool of FIG. 28B may be designed to inflate a balloon to a fixed pressure. Alternatively, they may be designed to deliver a fixed volume of inflating fluid to inflate a balloon.

Any of the handle assemblies of the tools described herein and in the patent applications incorporated herein by reference may comprise a rotatable handle. Such a rotatable handle may be designed to convert a part of a rotational force exerted by a user to a rectilinear force to draw components of the handle assembly towards each other. One embodiment of a rotatable handle is disclosed in U.S. Pat. No. 5,697,159 (Linden) titled 'Pivoted hand tool', the entire disclosure of which is expressly incorporated herein by reference. Such designs of rotatable handles may be used for handle assemblies including, but not limited to a) handle 2752 and trigger 2756 in FIG. 28A, b) handle 2772 and trigger 2778 in FIG. 28B, etc.

Figure 29:
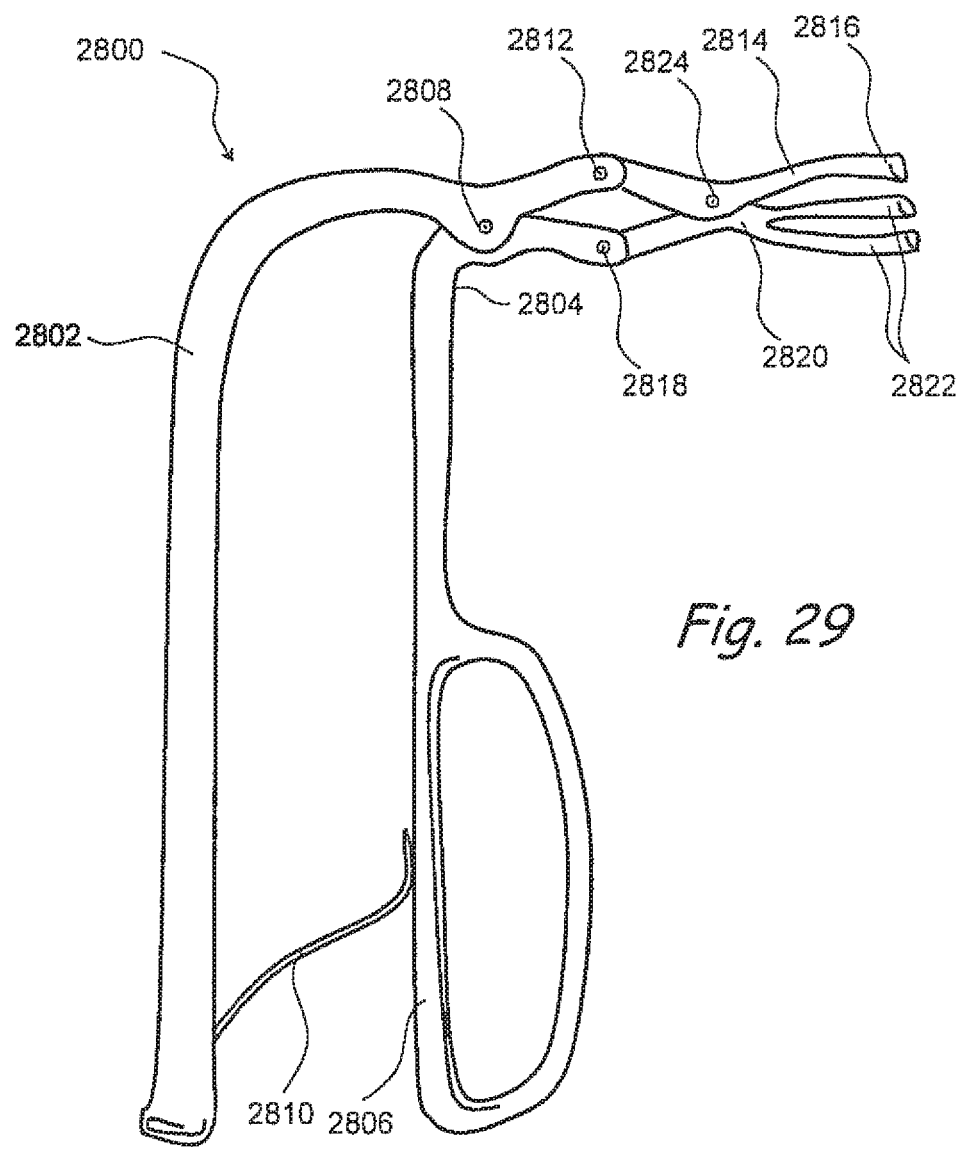
FIG. 29 shows a perspective view of a hand-held squeezing device useable to break or deform anatomical structures such a nasal turbinates.
Figure 29A:
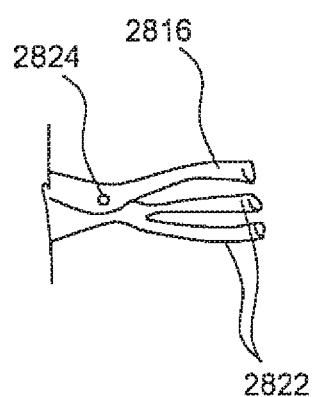
FIG. 29A shows a distal portion of the device of FIG. 29 in an open position.
Figure 29B:
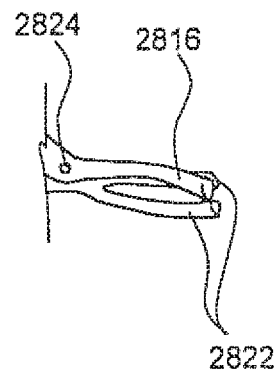
FIG. 29B shows a distal portion of the device of FIG. 29 in a closed position.

FIG. 29 shows a perspective view of a hand-held squeezing device to break or deform one or more anatomical structures such a nasal turbinates. Squeezing device 2800 comprises a two or more of distal squeezing elements that are used by a user to squeeze tissue located between the distal squeezing elements. Squeezing device 2800 can be used to temporarily or permanently deform tissue, break tissue, etc. In the embodiment shown in FIG. 29, squeezing device 2800 comprises a proximal handle element 2802 and a distal handle element 2804. Distal handle element 2804 may comprise an opening 2806 to enable a user to insert one or more fingers through opening 2806 to pull distal handle element 2804. Proximal handle element 2802 and distal handle element 2804 are hinged together by a first hinge 2808. A spring device 2810 is used to bias proximal handle element 2802 and distal handle element 2804 such that the proximal regions of proximal handle element 2802 and distal handle element 2804 are spaced apart. In this embodiment, spring device 2810 comprises a bent, elastic metal strip as shown. One end of the strip is fixed to proximal handle element 2802 and the other end of the strip slides over a surface of distal handle element 2804. The distal region of proximal handle element 2802 is connected by a second hinge 2812 to the proximal region of an elongate first distal element 2814. The distal region of first distal element 2814 may comprise one or more compression arms 2816 to compress tissue. Compression arms 2816 may be substantially straight or may comprise one or more bent, curved or angled regions. In this embodiment, the distal region of first distal element 2814 comprises a single compression arm 2816. The distal region of distal handle element 2804 is connected by a third hinge 2818 to the proximal region of an elongate second distal element 2820. The distal region of second distal element 2820 may comprise one or more compression arms 2822 to compress tissue. Compression arms 2822 may be substantially straight or may comprise one or more bent, curved or angled regions. In this embodiment, the distal region of second distal element 2820 comprises a two compression arm 2822. The curved middle regions of first distal element 2814 and second distal element 2820 are connected to each other by a fourth hinge 2824. In one embodiment of a method of using squeezing device 2800, a user squeezes proximal handle element 2802 and distal handle element 2804 towards each other. This causes the distal ends of proximal handle element 2802 and distal handle element 2804 move away from each other. This in turn causes the proximal ends of first distal element 2814 and second distal element 2820 to move apart from each other. This in turn causes compression arm 2816 and compression arms 2822 to move closer to each other. This squeezes tissue located between compression arm 2816 and compression arms 2822. In one method embodiment, squeezing device 2800 is used to crush or break a region of a nasal turbinate to gain access to a paranasal sinus ostium. The various components of squeezing device 2800 may be made using suitable biocompatible materials including, but not limited to stainless steel, titanium, etc. FIGS. 29A and 29B show enlarged views of the distal region of the squeezing device of FIG. 29. FIG. 29A shows the orientation of compression arm 2816 and compression arms 2822 when squeezing device 2800 is in an undeployed configuration. FIG. 29B shows the orientation of compression arm 2816 and compression arms 2822 when squeezing device 2800 is being used to squeeze tissue.

FIGS. 29C and 29D show a coronal section through a region of a human head showing the steps of temporarily or permanently breaking or deforming a nasal turbinate NT using the squeezing device of FIG. 29. In FIG. 29C, squeezing device 2800 is introduced in the nasal cavity. Thereafter, squeezing devices 2800 is positioned such that compression arm 2816 is located on one side of the nasal turbinate NT and compression arms 2822 are located on the other side of the nasal turbinate. In FIG. 29D, a user deploys squeezing device 2800. This causes compression arm 2816 and compression arms 2822 to squeeze the region of the nasal turbinate NT located between compression arm 2816 and compression arms 2822.

FIG. 29E shows a perspective view of a hand-held device to twist one or more anatomical structures such a nasal turbinates. Twisting device 2830 comprises two or more distal arms that are placed around an anatomical structure. Thereafter, the two or more arms are twisted to temporarily or permanently deform or break the anatomical structure. In the embodiment shown in FIG. 29E, twisting device 2830 comprises a proximal handle 2832, a middle region 2834 and two distal arms 2836. Proximal handle 2832 may have a substantially larger outer diameter than the maximum width of the distal region of twisting device 2830 to enable a user to easily twist the anatomical structure. The various components of squeezing device 2800 may be made using suitable biocompatible materials including, but not limited to stainless steel, titanium, etc. In one method embodiment, twisting device 2830 is used to deform or break a region of a nasal turbinate to gain access to a paranasal sinus ostium.

FIGS. 29G and 29G show a coronal section through a region of a human head showing the steps of temporarily or permanently breaking or deforming a nasal turbinate NT using the squeezing device of FIG. 29. In FIG. 29G, twisting device 2830 is introduced in the nasal cavity. Thereafter, twisting device 2830 is positioned such that one of arms 2836 is located on one side of the nasal turbinate NT and the other of arms 2836 is located on the other side of the nasal turbinate. In FIG. 29G, a user twists twisting device 2830. This causes arms 2836 to twist the region of the nasal turbinate NT located between arms 2836 to temporarily or permanently break or deform the nasal turbinate NT.

The devices disclosed in FIGS. 29B through 29G are especially useful to treat patients with narrow noses to controllably fracture a nasal turbinate to allow access to a paranasal sinus ostium.

The rigid or flexible endoscopes disclosed herein may have a range of view ranging from 0 degrees to 145 degrees. The embodiments of endoscopes comprising a curved, bent or angled region may be manufactured by curving or bending the optical fibers before fusing the optical fibers. The optical fibers may be fused for example by heating them to a temperature ranging from 500 to 700 degrees Celsius or by using suitable epoxy adhesives to attach the optical fibers to each other. The endoscopes may be made using reduced cladding thickness optical fibers to allow curved, bent or angled regions with a large angle or curvature but a small radius of curvature. The endoscopes may also be made using glass/glass/polymer (GGP) multimode fiber such as the ones made by 3M to allow curved, bent or angled regions with a large angle or curvature but a small radius of curvature. For example, in embodiments of endoscopes that have a bent, curved or angled region enclosing an angle of 90 degrees or more, the radius of curvature of the bent, curved or angled region may preferably be less than or equal to 1.5 cm. Such endoscopes comprising curved, bent or angled regions with a large angle or curvature but a small radius of curvature are especially useful to enable a user to access the maxillary sinuses.

The embodiments herein have been described primarily in conjunction with minimally invasive procedures, but they can also be used advantageously with existing open surgery or laparoscopic surgery techniques. For example, the methods and devices disclosed herein may be combined with one or more techniques of Functional Endoscopic Sinus Surgery (FESS). In FESS, a surgeon may remove diseased or hypertrophic tissue or bone and may enlarge the ostia of paranasal sinuses to restore normal drainage of the sinuses. It is typically performed with the patient under general anesthesia using endoscopic visualization.

Although FESS continues to be the gold standard therapy for severe sinuses, it has several shortfalls such as post-operative pain and bleeding associated with the procedure, failure to relieve symptoms in a significant subset of patients, risk of orbital, intracranial and sinonasal injuries, etc. Replacing one or more steps of FESS may reduce the shortfalls associated with the traditional FESS. The following are some examples of procedures involving a combination of FESS and the procedures disclosed in this patent application and the patent applications incorporated herein by reference.

1. In one combination procedure, a maxillary sinus is treated by balloon dilation with or without total or partial removal of the uncinate. Total or partial removal of the uncinate may make it easier or faster for some physicians to visualize and access the maxillary sinus.

2. In another combination procedure, a maxillary sinus is treated by balloon dilation in conjunction with removal of a nasal turbinate. During this combination procedure, a part or the entire nasal turbinate e.g. the middle turbinate may be removed. Removing a part or the entire middle turbinate provides additional working space in the region medial to the uncinate for instruments. This may potentially make the combination procedure easier or faster.

3. In another combination procedure, a sphenoid sinus ostium is treated by balloon dilation in conjunction with ethmoidectomy. The step of ethmoidectomy may enable a physician to introduce a guide catheter through the middle meatus to the sphenoid sinus ostium. This may potentially enable easy access to the sphenoid sinus ostium.

4. In another combination procedure, a frontal sinus is treated by balloon dilation in conjunction with middle turbinate resection and/or ethmoidectomy. This combination procedure may make easier for a physician to find, visualize or access the frontal sinus once anatomical structures like Ethmoid bulla, turbinate, etc. are removed or reduced.

5. In another type of combination procedures, multiple sinuses are treated by balloon dilation with no or minimal tissue or bone removal. This is then followed by standard techniques to treat sinus disease. Examples of such combination procedures include:

5A. Frontal, maxillary, or sphenoid sinuses are treated by balloon dilation. Also, ethmoidectomy is performed while preserving the uncinate. The presence of the uncinate may preserve the natural function of the uncinate. This in turn may lead to lower incidence of complications like infection, etc. in the sinuses.

5B. Any paranasal sinus may be treated by balloon dilation combined with a second procedure including, but not limited to ethmoidectomy, septoplasty, reduction of a turbinate (e.g. inferior turbinate, middle turbinate, etc.), etc.

6. Any of the procedures disclosed herein may be performed in conjunction with irrigation and suction of one or more paranasal sinuses with a flexible catheter or rigid instrument. A flexible catheter is particularly useful to reach regions that are difficult to access by rigid instruments. Such regions may be located in lateral aspects of the frontal sinuses, the inferior or medial aspects of the maxillary sinuses, etc.

7. Any of the procedures disclosed herein may further include removal of one or more polyps. Polyp removal by standard techniques such as using shavers can be combined with balloon dilation of various paranasal sinus ostia. Once one or more polyps are removed, one or more ostia of paranasal sinuses may be dilated by balloon dilation.

8. In another type of combination procedures, balloon dilation of one or more paranasal sinus ostia may be performed to revise a previously performed surgery or in conjunction with standard endoscopic sinus surgery techniques. Examples of such procedures include:

8A. Treating scar formation over frontal recess: In this combination procedure, an attempt is made to access frontal recess with a guidewire. A balloon catheter is then passed over the guidewire. If the guidewire is unable to access the frontal sinus ostia because of scarring or because the frontal sinus ostia are too small, a surgical instrument e.g. curette or seeker may be used to open or puncture scar tissue or adhesions or the frontal sinus ostia. Such scar tissue or adhesions may be caused for example due to infection, prior surgery, etc. Thereafter, the frontal sinus ostia may be dilated by balloon dilation.

8B. Combination procedures similar to the abovementioned combination procedure may be performed to treat scarring near sphenoid sinuses and maxillary sinuses.

9. In another type of combination procedures, one or more paranasal sinuses e.g. a maxillary sinus may be accessed by an artificially created opening leading to the sinuses. Thereafter, a diagnostic or therapeutic procedure disclosed herein or in the patent documents incorporated herein by reference may be performed. The artificially created opening may be used to endoscopically visualize the placement of devices such as balloon catheters, guidewires, or other devices through a natural ostium of the paranasal sinus. The artificially created opening may also be used to introduce one or more diagnostic, therapeutic or access devices. The artificially created opening may be used to introduce liquids including, but not limited to solutions of antibiotics, solutions of anti-inflammatory agents, etc. The artificially created opening may be made by using suitable devices including, but not limited to drilling devices, chopping devices, puncturing devices, etc.

Some specific examples of hybrid procedures of the present invention are shown in the flow diagrams of FIGS. 30-33.

Figure 30:
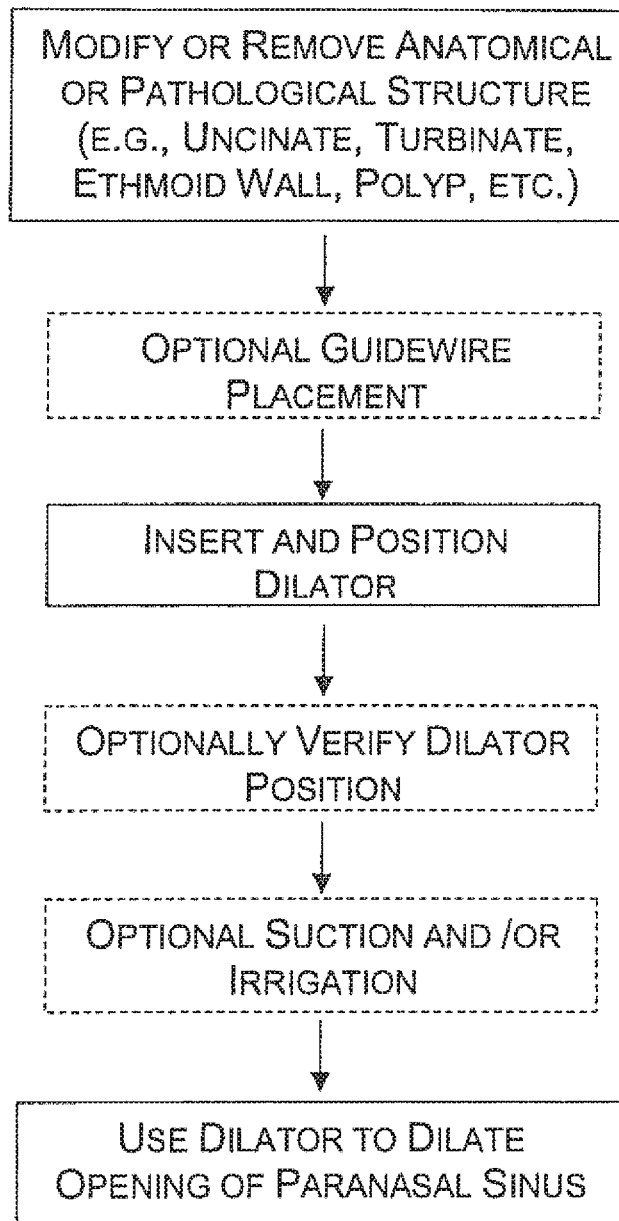
FIG. 30 is a flow diagram of a method useable for treating sinus disorders by removal or modification of an anatomical or pathological structure in combination with dilation of an opening of a paranasal sinus.

FIG. 30 shows steps in a method wherein an anatomical or pathological structure, such as the uncinate process, a turbinate, the wall of an ethmoid air cell, a polyp, etc. is removed or substantially modified and a dilator (e.g., the balloon of a balloon catheter) is positioned within an opening of a paranasal sinus and used to dilate that opening. Removal or modification of the anatomical or pathological structure may provide clearer access to and/or visibility of certain anatomical structures during the procedure or during post-operative examinations and follow-up.

Figure 31:
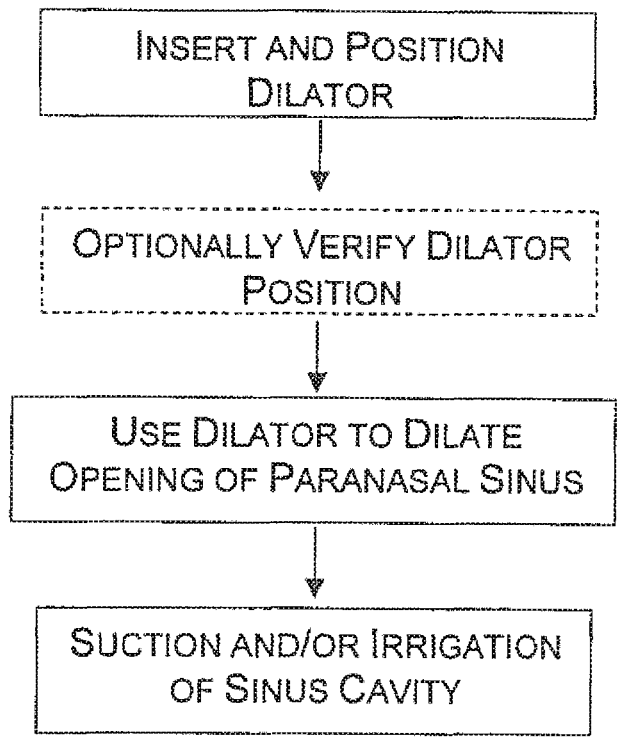
FIG. 31 is a flow diagram of a method useable for treating sinus disorders by dilation of an opening of a paranasal sinus in combination with suction and/or irrigation of a sinus cavity.

FIG. 31 shows steps in a method where a dilator such as the balloon of a balloon catheter is positioned in the opening of a paranasal sinus and used to dilate that opening and, either before or after such dilation, the cavity of the paranasal sinus is suctioned or irrigated. In cases where a balloon catheter or other dilator device having a through lumen is used to accomplish the dilation step, the irrigation and/or suction step may be carried out by passing fluid or negative pressure through the through lumen of the dilation catheter. Or, a guidewire may be advanced into or near the sinus cavity during the dilation step and, thereafter, a suction and/or irrigation device may be advanced over such guidewire and used to carry out the suction and/or irrigation step.

Figure 32:
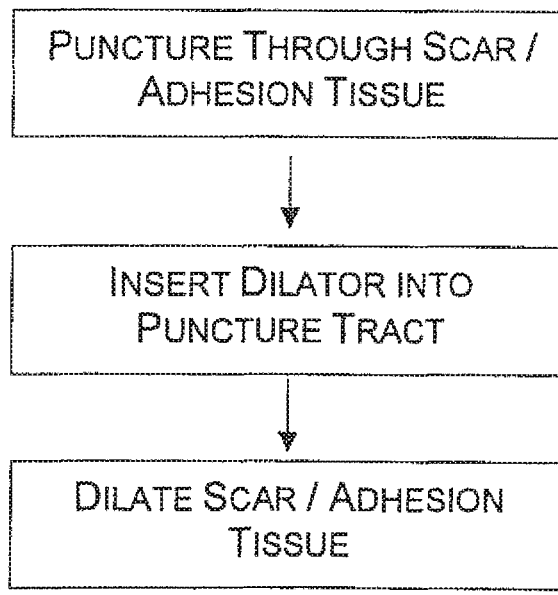
FIG. 32 is a flow diagram f a method useable for treating conditions where unwanted scar or adhesion tissue has formed by forming a puncture tract in the scar or adhesion tissue, inserting a dilator into the puncture tract and dilating the puncture tract.

FIG. 32 shows steps in a method where scar or adhesion tissue has formed in a location that obstructs a lumen, orifice, or passageway (e.g., scar tissue obstruction the opening of a paranasal sinus) and a puncture tract is initially formed in the scar or adhesion tissue. This may be accomplished by pushing a needle, seeker, probe, guidewire or other penetrator through the tissue. Therafter, a dilator (e.g., a balloon catheter) is advanced into the puncture tract and is used to dilate the puncture tract, thereby relieving the obstruction caused by the aberrant scar or adhesion tissue.

Figure 33:
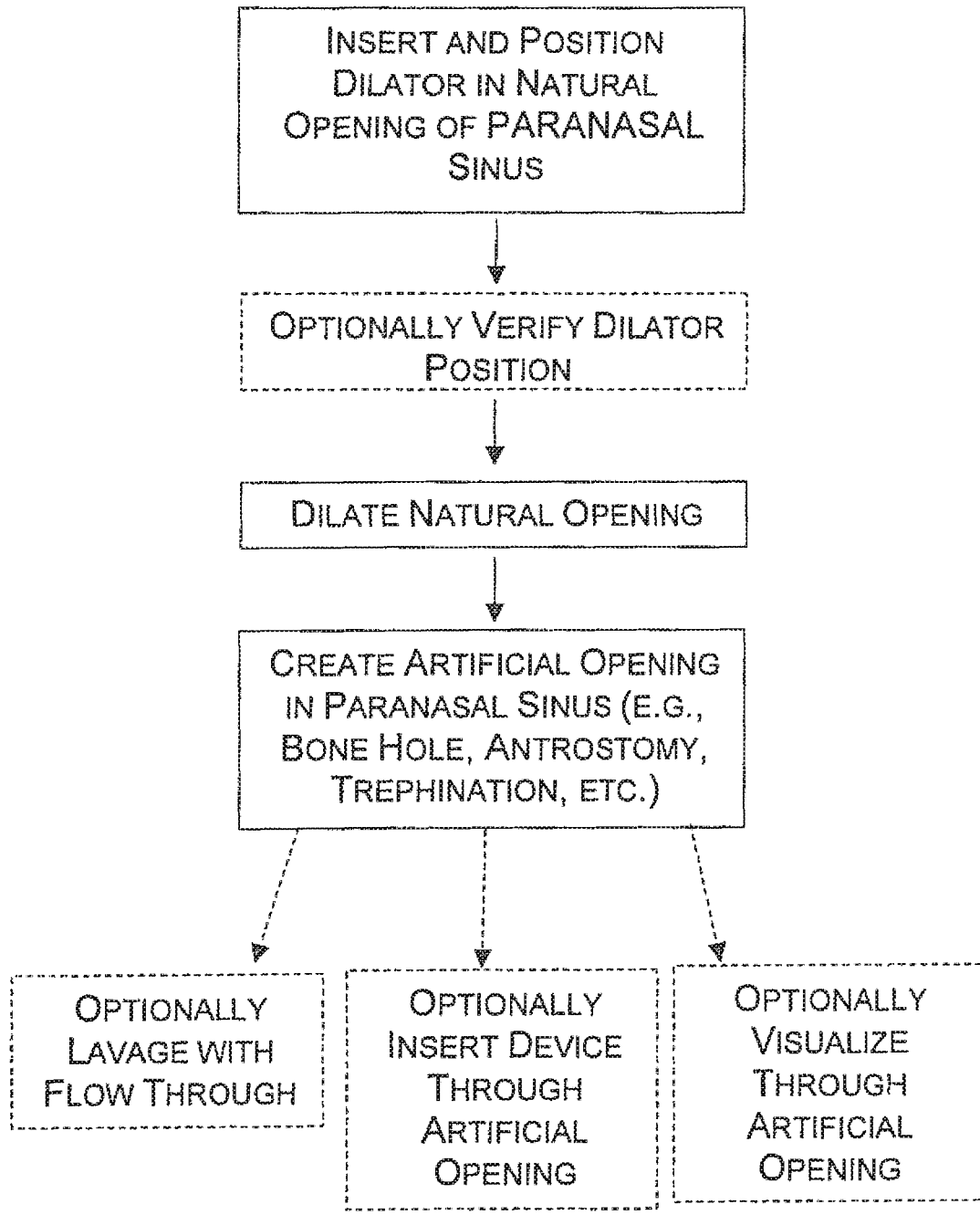
FIG. 33 a flow diagram of a method useable for treating sinus disorders by dilation of a natural opening of a paranasal sinus in combination with the creation of a new opening in the paranasal sinus.

FIG. 33 shows steps in a method wherein a dilator (e.g., the balloon of a balloon catheter) is placed in a pre-existing opening of a paranasal sinus, such as the natural ostium of the sinus (or a previously surgically altered ostium) and is used to dilate that opening. Also, a separate opening is created in that paranasal sinus, either from the nasal cavity or through the exterior of the face (e.g., a bore hole, antrostomy or trephination). This may provide improved ventilation and/or drainage of the sinus cavity. Optionally, the two openings may then be used to perform other procedures. For example, a "flow through" lavage may be carried out by passing lavage solution through one of the openings and out of the other. Or, a device may be inserted through one of the openings, leaving the other opening unobstructed. Or, the physician may visualize (e.g., through an endoscope) through the newly created opening while treated the pre-existing opening or performing other diagnosis or treatment of the sinus cavity.

It is to be appreciated that the devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

It is to be appreciated that the invention has been described hereabove with reference to certain examples or embodiments of the invention but that various additions, deletions, alterations and modifications may be made to these examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method of using an instrument, the method comprising:
    (a) coupling the instrument with a navigation adapter, wherein the navigation adapter includes an opening configured to receive a portion of the instrument therethrough, wherein the navigation adapter further includes a navigation element configured for detection by a navigation system;
    (b) inserting the instrument in a patient, such that the navigation element is positioned external to the patient and a distal portion of the instrument is positioned in a passageway in an ear, nose, or throat of the patient;
    (c) operating a navigation system to determine a position of the navigation element, wherein the position of the navigation element is indicative of a position of the instrument in the patient; and
    (d) tracking movement of the instrument in the patient based on the position of the navigation element as determined by the navigation system.

2. The method of claim 1, wherein the instrument includes a dilation instrument with an expandable member.

3. The method of claim 2, wherein the dilation instrument comprises a balloon catheter, wherein the expandable member comprises a balloon.

4. The method of claim 2, further comprising expanding the expandable element of the instrument.

5. The method of claim 4, wherein expansion of the expandable element results in dilation of the passageway in the ear, nose, or throat of the patient.

6. The method of claim 5, wherein the dilated passageway comprises a sinus ostium.

7. The method of claim 1, wherein the navigation system is configured to optically detect the navigation element.

8. The method of claim 1, wherein the navigation element is configured to emit electromagnetic energy.

9. The method of claim 8, wherein the navigation element is configured to emit radiofrequency energy.

10. The method of claim 1, wherein the navigation element comprises a radiopaque marker.

11. The method of claim 1, wherein the navigation element includes an electromagnetic sensor.

12. The method of claim 11, wherein the electromagnetic sensor includes an electromagnetic coil.

13. The method of claim 1, wherein the passageway in the patient comprises an opening of a paranasal sinus in the patient.

14. The method of claim 1, wherein the instrument defines a suction lumen, the method further comprising applying suction in the ear, nose, or throat of the patient via the suction lumen.

15. The method of claim 1, wherein the instrument includes a cannula, wherein coupling the instrument with the navigation adapter includes coupling the instrument with a proximal portion of the cannula.

16. The method of claim 15, wherein the cannula includes a region that is curved, angled, or bent, such that the cannula is not straight.

17. A method of using an instrument, the method comprising:
    (a) coupling an instrument with a navigation adapter, wherein the navigation adapter includes a coupling feature configured to receive a portion of the instrument, wherein the navigation adapter includes a navigation element configured for detection by an electromagnetic navigation system;
    (b) inserting a distal portion of the instrument into the patient, wherein the instrument further includes a proximal portion located external to the patient after the distal portion is inserted in the patient;
    (c) operating the electromagnetic navigation system to observe the navigation element located on the proximal portion of the instrument that is located external to the patient, wherein a position of the navigation element is indicative of a position of the distal portion in the patient; and
    (d) operating the distal portion of the instrument such that the distal portion is positioned in a targeted anatomical passageway.

18. The method of claim 17, wherein the proximal portion comprises a plurality of navigation elements.

19. The method of claim 17, wherein the navigation element includes an electromagnetic coil, wherein the electromagnetic navigation system is configured to detect a movement of the electromagnetic coil.

20. A method comprising:
    (a) coupling an instrument with a navigation adapter, wherein the navigation adapter is configured to removably couple with a portion of the instrument, wherein the navigation adapter is configured to receive a portion of the instrument therethrough, wherein the navigation adapter includes a navigation element configured for detection by an electromagnetic navigation system;
    (b) inserting a distal portion of the dilation instrument into the patient such that a navigation element of the dilation instrument is positioned external to the patient;
    (c) activating the electromagnetic navigation system to locate a position of the navigation element external of the patient and a position of the distal portion in an anatomical structure;
    (d) moving the expandable member within the patient toward the anatomical structure; and
    (e) observing the movement of the distal portion in the patient with the electromagnetic navigation system based on the position of the navigation element relative to the distal portion.

* * * * *